US010702568B2

(12) United States Patent
Pipkin et al.

(10) Patent No.: US 10,702,568 B2
(45) Date of Patent: Jul. 7, 2020

(54) COMPOSITIONS CONTAINING SILYMARIN AND SULFOALKYL ETHER CYCLODEXTRIN AND METHODS OF USING THE SAME

(71) Applicants: UNIVERSITY OF KANSAS, Lawrence, KS (US); CYDEX PHARMACEUTICALS, INC., San Diego, CA (US)

(72) Inventors: James D. Pipkin, Lawrence, KS (US); Roger A. Rajewski, Lawrence, KS (US); Beau Mainous, Duluth, GA (US)

(73) Assignees: CyDex Pharmaceuticals, Inc., San Diego, CA (US); University of Kansas, Lawrence, KS (US)

( * ) Notice: Subject to any disclaimer, the term of this patent is extended or adjusted under 35 U.S.C. 154(b) by 304 days.

(21) Appl. No.: 15/559,005

(22) PCT Filed: Mar. 18, 2016

(86) PCT No.: PCT/US2016/023309
§ 371 (c)(1),
(2) Date: Sep. 15, 2017

(87) PCT Pub. No.: WO2016/149685
PCT Pub. Date: Sep. 22, 2016

(65) Prior Publication Data

US 2018/0133274 A1 May 17, 2018

Related U.S. Application Data

(60) Provisional application No. 62/135,625, filed on Mar. 19, 2015.

(51) Int. Cl.

| | |
|---|---|
| ***A61K 36/28*** | (2006.01) |
| ***A61Q 19/08*** | (2006.01) |
| ***A61K 47/40*** | (2006.01) |
| ***A61K 9/00*** | (2006.01) |
| ***A61K 8/49*** | (2006.01) |
| ***A61K 8/73*** | (2006.01) |
| ***A61K 31/353*** | (2006.01) |
| ***A61K 31/357*** | (2006.01) |
| ***A61K 9/06*** | (2006.01) |
| ***A61P 17/06*** | (2006.01) |
| ***A61P 1/16*** | (2006.01) |
| ***A61K 8/96*** | (2006.01) |
| ***A61Q 17/04*** | (2006.01) |

(52) U.S. Cl.
CPC .............. *A61K 36/28* (2013.01); *A61K 8/498* (2013.01); *A61K 8/738* (2013.01); *A61K 8/96* (2013.01); *A61K 9/0014* (2013.01); *A61K 9/06* (2013.01); *A61K 31/353* (2013.01); *A61K 31/357* (2013.01); *A61K 47/40* (2013.01); *A61P 1/16* (2018.01); *A61P 17/06* (2018.01); *A61Q 19/08* (2013.01); *A61K 2300/00* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 3,426,011 | A | 2/1969 | Parmerter et al. |
| 5,087,445 | A | 2/1992 | Haffey et al. |
| 5,100,660 | A | 3/1992 | Hawe et al. |
| 5,134,127 | A | 7/1992 | Stella et al. |
| 5,198,430 | A | 3/1993 | Valcavi et al. |
| 5,241,059 | A | 8/1993 | Yoshinaga |
| 5,376,645 | A | 12/1994 | Stella et al. |
| 5,714,473 | A | 2/1998 | Lentzen et al. |
| 5,874,418 | A | 2/1999 | Stella et al. |
| 5,972,993 | A | 10/1999 | Ptchelintsev |
| 6,153,746 | A | 11/2000 | Shah et al. |
| 6,187,822 | B1 | 2/2001 | Leibovich |
| 8,022,038 | B2 | 9/2011 | Miyata et al. |
| 8,426,459 | B2 | 4/2013 | Stuchlik et al. |
| 2005/0250738 | A1 | 10/2005 | Mosher et al. |
| 2006/0172005 | A1 | 8/2006 | Hara et al. |
| 2008/0033037 | A1 | 2/2008 | Bernard et al. |
| 2009/0269291 | A1 | 10/2009 | Gupta |
| 2011/0212169 | A1 | 9/2011 | Bae et al. |

(Continued)

FOREIGN PATENT DOCUMENTS

| | | |
|---|---|---|
| CN | 1391894 | 1/2003 |
| CN | 1593591 A | 3/2005 |

(Continued)

OTHER PUBLICATIONS

Valentová, et al., Food and Chemical Toxicology, 56:178. (Year: 2013).*
Liu, et al., Journal of Chromatography B, 877:4159. (Year: 2009).*
CN1424112A (English translation retrieved from Google Patents). (Year: 2003).*
Adam et al., 2002, Cyclodextrin-derived host molecules as reversal agents for the neuromuscular blocker rocuronium bromide: synthesis and structure-activity relationships, J. Med. Chem. 45:1806-1816.
Ajazuddin, 2010, Application of novel drug delivery system for herbal formulations, Fitoterapia, 81:680-689.

(Continued)

*Primary Examiner* — Michael Barker
(74) *Attorney, Agent, or Firm* — Knobbe, Martens, Olson & Bear LLP

(57) ABSTRACT

Cosmetic and dietary supplement compositions containing silymarin and sulfoalkyl ether cyclodextrin, particularly sulfobutyl ether cyclodextrin, are described. The compositions and methods are useful in reducing appearance of facial redness in rosacea-prone skin, rejuvenating skin, preventing skin aging, inhibiting oxidative stress in epidermal and dermal cells, increasing collagen production, reducing the likelihood of skin cancer, treating or reducing liver damage from a toxin, or treating a liver disease.

13 Claims, 29 Drawing Sheets

(56) References Cited

U.S. PATENT DOCUMENTS

| | | | |
|---|---|---|---|
| 2012/0108825 | A1 | 5/2012 | Rovati et al. |
| 2013/0209504 | A1 | 8/2013 | Florence et al. |

FOREIGN PATENT DOCUMENTS

| | | | |
|---|---|---|---|
| CN | 1679542 | | 10/2005 |
| CN | 101810660 | B | 6/2011 |
| CN | 102106819 | | 6/2011 |
| DE | 4101122 | A | 7/1992 |
| EP | 0 422 497 | | 3/1996 |
| EP | 3 243 512 | | 11/2017 |
| JP | 05-286864 | | 11/1993 |
| JP | 2008-179618 | | 8/2008 |
| JP | 2008-530062 | | 8/2008 |
| KR | 10-2010-067257 | | 6/2010 |
| WO | WO 87/05297 | | 9/1987 |
| WO | WO 01/40316 | | 6/2001 |
| WO | WO 03/043602 | | 5/2003 |
| WO | WO 05/042584 | | 5/2005 |
| WO | WO 09/018326 | | 2/2009 |
| WO | WO 11/044638 | | 4/2011 |

OTHER PUBLICATIONS

Alam et al., Oct. 2013, Commercially bioavailable proprietary technologies and their marketed products, Drug Discovery Today, 18(19-20):936-949.

Arcari et al., May 1992, A new inclusion complex of silibinin and beta-cyclodextrins: in vitro dissolution kinetics and in vivo absorption in comparison with traditional formulations, Boll Chim Farm, 131(5):205-209 (abstract).

Biswas et al., Preparation and evluation of silymarin β-cyclodextrin molecular inclusion complexes, Journal of Young Pharmacists, 3(3):205-210.

Deep et al., 2014, Silibinin inhibits fibronectin induced motility, invasiveness and survival in human prostate carcinoma PC3 cells via targeting integrin signaling, Mutation Research/Fundamentla and Molecular Mechanisms of Mutagenesis, 768:35-46.

Fenyvesi et al., Jan. 2011, Solubility increasing experiments of sylimarin with cyclodextrins, Jurnal Medical Aradean, xiv(2):13-17.

Gazak et al., 2007, Silybin and silymarin—new and emerging applications in medicine, Current Medicinal Chemistry, 14:315-338.

Gonzalez et al., 2010, Photoprotection: update in uv-filter molecules, the "new wave" of sunscreens, G. Ital. Dermatol. Venereol., 145(4):515-523.

Gu et al., 2007, Silibinin inhibits inflammatory and angiogenic attributes in photocarcinogenesis in SKH-1 hairless mice, Cancer Research 67(7):3483-3491.

Hasanloo et al., 2005, Analysis of flavonolignans in dried fruits of *Silyburm marianum* (L.) Gaertn from Iran, Pakistan Journal of Biological Sciences, 8(12):1778-1782.

Indena, Oct. 2008, Silymarin Phytosome®, product brochure, 2 pp.

Javed et al., 2011, Reassessing bioavailablity of silymarin, Altermative Medicine Review, 16(3):239-249.

Jayaraj et al., 2007, Hepatoprotective efficacy of certain flavonoids against microcystin induced toxicity in mice, Environmental Toxicology, pp. 472-479.

Jung et al., 1996, Comparison of γ-cyclodextrin sulfobutyl ether and unmodified γ-cyclodextrin as chiral selectors in capillary electrophoresis, J Chromat. 755:81-88.

Kara et al., Dec. 2008, Effects of silymarin and pentoxifylline on matrix metalloproteinase-1 and -2 expression and apoptosis in experimental hepatic fibrosis, Current Therapeutic Research, 69(6):488-502.

Kwon et al., 2010, Enhancement of solubility and antioxidant activity of some flavonoids based on the inclusion complexation with sulfobutylether β-cyclodextrin, Bulletin of the Korean Chemical Society, 31(10):3035-3037.

Lammers et al., 1971, Properties of cyclodextrins: Part VI. Water-soluble cyclodextrin-derivatives. Preparation and Analysis, Die Starke, 23(5):167-171.

Lammers et al., 1972, Properties of cyclodextrins, Part VIII Determination of the composition of inclusion complexes of hexane and 2,3-dimethylbutane with cyclodextrin derivatives in aqueous solution, Recl. Trav. Chim. Pays-Bas, 91(6):733-753.

Linder, Apr. 2014, Cosmeceuticals Series, Part 2: Antioxidants, Practical Dermatology, pp. 51-54.

Lirussi et al., 2002, Silybin-beta-cyclodextrin in the treatment of patients with diabetes mellitus and alcoholic liver disease. Efficacy study of a new preparation of an anti-oxidant agent, Diabetes, Nutrition & Metabolism, 15(4):222-231.

Liu et al., Jul. 10, 2013, Inclusion complexes of quercetin with three [beta]-cyclodextrins derivatives at physiological pH: spectroscopic study and antioxidant activity, Spectrochimica Acta. Part A: Molecular and Biomolecular Spectroscopy, 115:854-860.

Loftsson, Dec. 1999, Pharmaceutical applications of β-cyclodextrin, Pharmaceutical Technology, 12:41-50.

Luna et al., 1997, Fractionation and characterization of 4-sulfobutyl ether derivatives of cyclomaltoheptaose (β-cyclodextrin), Carbohydrate Research, 299:103-110.

Ma, 1999, Thermal properties and processing of (sulfobutylether)$_{7m}$-β-cyclodextrin as a freeze-drying excipient in pharmaceutical formulation, S.T.P. Pharma Sciences, 9(3):261-266.

Milic et al., 2013, New therapeutic potentials of milk thistle (*Silybum marianum*), Natual Product Communications, 8(12):1801-1810.

Miyata, 2007, Preventino of skin aging by topical and oral applications of silybin, which was isolated from the seeds of milk thistle, Bio Industry, 24(8):19-25.

MUP Kazakhstan, 2011, Hepaticum: the comprehensive liver support, Silybin-β-cyclodextrin complex, 5 pp.

Neuman et al., 1999, Inducers of cytochrome P450 2E1 enhance methotrexate-induced hepatocytotoxicity, Clinical Biochemistry, 32(7):519-536.

Omar et al., 2012, First detailed quantification of silymarin components in the leaves of Silybum marianum cultivated in Egypt during different growth stages, Acta Chromatographica, 24(3):463-474.

Qu et al., 2002, Sulfoalkyl ether β-cyclodextrin derivatives: synthesis and characterizations, J. Inclusion Phenom. Macro. Chem, 43:213-221.

Rendon et al., Jul. 2005, Review of skin-lightening agents, Dermatol. Surg., 31(7 Part 2):886-889.

Shafik et al., 2011, Improved antifibrotic effect of a combination of verapamil and silymarin in rat-induced liver fibrosis, Arab Journal of Gastroenterology, 12:143-149.

Sidhu et al., 2012, Silybum marianum: a plant of high medicinal importance—a review, World Journal of Pharmaceutical Research, 1(2):72-86.

Spada et al.,2013, Evaluation of the effect of hydroxypropyl-β-cyclodextrin on topical administration of milk thistle extract, Carbohydrate Polymers, 92(1):40-47.

Stella et al., Jan. 2008, Cyclodextrins, Toxicologic Pathology, 36(1):30-42.

Tarver et al., 2002, 2-O-substituted cyclodextrins as reversal agents for the neuromuscular blocker rocuronium bromide, Bioorganic & Medicinal Chemistry, 10:1819-1827.

Taxifolin, Wikipedia, https://en.wikipedia.org/w/index.php?title=Taxifolin&oldid=643087533>, Published Jan. 18, 2015 according to Wikipedia, Retrieved May 6, 2016.

Trappoliere et al., 2009, Silybin, a component of sylimarin, exerts anti-inflammatory and anti-fibrogenic effects on human hepatic stellate cells, Journal of Hepatology, 50:1102-1111.

Voinovich et al., 2009, Solid state mechanochemical activation of silybum marianum dry extract with betacyclodextrins: characterization and bioavailability of the coground systems, J. Pharm. Sci., 98:4119-4129.

Zhu et al., 2008, The use of botanical extracts as topical skin-lightening agents for the improvement of skin pigmentation disorders, Journal of Investigative Dermatology, Symposium Proceedings, 13(1):20-24.

(56) References Cited

OTHER PUBLICATIONS

International Search Report and Written Opinion dated May 24, 2016 in application No. PCT/US2016/023309.

Notice of Reason for Rejection dated Jan. 7, 2020 in Japanese patent application No. 2018-500282.

* cited by examiner

1. Unknown, 2. Silychristin A, 3. Silydianin, 4. Silychristin B, 5. Silybin A, 6. Silybin B, 7. 2,3-cis-Silybin A, 8. 2,3-cis-Silybin B, 9. Isosilybin A, 10. Isosilybin B, 11. 2,3-cis-isosilybin isomer

COMPOSITIONS CONTAINING SILYMARIN AND SULFOALKYL ETHER CYCLODEXTRIN AND METHODS OF USING THE SAME

BACKGROUND

Field

This invention relates to the fields of medicine, dietary supplements, and cosmetics. Some embodiments include a composition containing silymarin or components of silymarin and sulfoalkyl ether cyclodextrin and methods of using the same.

Description of the Related Art

Changes that occur in the skin due to aging, such as wrinkles and sagging, are known to be accelerated by physical and psychological stress, exposure to sunlight, and so on. As the skin ages, epidermal cells and fibroblast cells that comprise the skin tissues will decrease and the blood vessels that supply substances needed to support the activity of these cells will also decrease. In addition, the extracellular matrix that retains the skin structure will also change.

In order to prevent the visible signs of skin aging as described above, various formulations have been developed. For example, natural plant extracts that promote collagen and elastin production have been included in topical compositions.

Silymarin, a flavonolignan derived from *Silybum marianum*, commonly known as milk thistle in the family Asteraceae, possesses diverse pharmacological activities, including hepatoprotective, antioxidant, anti-inflammatory, anticancer, and cardioprotective effects. *Silybum marianum* has been used for the treatment of liver and gallbladder disorders, including hepatitis, cirrhosis, jaundice, and provide protection against *Amanita phalloides* mushroom and other toxin poisonings. Silymarin, the active component of this plant, is a standardized extract consisting of approximately 70-80 percent silymarin flavonolignans (silybin A & B, isosilybin A & B, silydianin, and silychristin) and favonoids (taxifolin and quercetin), and the remaining 20-30 percent consisting of a chemically undefined fraction comprised of polymeric and oxidized polyphenolic compounds.

The reported biological and pharmacological effects of silymarin include antioxidant activity, stimulation of protein synthesis and cell regeneration. However, silymarin has a low solubility (0.04 mg/ml) in water. Silymarin possesses no lipophilic properties, even though its water solubility is poor. In addition, the bioavailability of silymarin is also low.

SUMMARY

One aspect of the disclosed technology relates to compositions containing silymarin and sulfoalkyl ether cyclodextrin. In some embodiments, the composition includes silymarin or one or more components selected from taxifolin, silychristin A, silydianin, silychristin B, silybin A, silybin B, 2,3-cis-silybin A, 2,3-cis-silybin B, isosilybin A, isosilybin B, or 2,3-cis-isosilybin isomer; and sulfoalkyl ether cyclodextrin.

Another aspect of the disclosed technology relates to a cosmetic composition for topical application, such as where the composition is in the form of a cream, ointment, gel, lotion, balm, liniment, paste, wash, shampoo, soap, spray or an emulsion.

Another aspect of the disclosed technology relates to a dietary supplement composition, such as where the composition is in the form of a pill, capsule, pellet, tablet, lozenge or pharmaceutical pastille, soft gel, liquid suspension, solution, syrup, granule or powder.

Another aspect of the disclosed technology relates to a method of reducing appearance of facial redness in rosacea-prone skin, wherein the method includes administering to a subject in need thereof an effective amount of the composition described herein.

Another aspect of the disclosed technology relates to a method of rejuvenating skin, wherein the method includes administering to a subject in need thereof an effective amount of the composition described herein.

Another of the disclosed technology relates to a method of preventing skin aging, wherein the method includes administering to a subject in need thereof an effective amount of the composition described herein.

Another aspect of the disclosed technology relates to a method of inhibiting oxidative stress in epidermal and dermal cells, wherein the method includes administering to a subject in need thereof an effective amount of the composition described herein. In some embodiments, the oxidative stress is induced by UV light, radiation, inflammation, exposure to cigarette smoke, pollution, or any combination thereof. In some embodiments, the oxidative stress is induced by UV light.

An additional aspect of the disclosed technology relates to a method of reducing or inhibiting procollagen production, wherein the method includes administering to a subject in need thereof an effective amount of the composition described herein.

An additional aspect of the disclosed technology relates to a method of reducing or inhibiting fibronectin production, wherein the method includes administering to a subject in need thereof an effective amount of the composition described herein.

Another aspect of the disclosed technology relates to a method of reducing or inhibiting scar formation, wherein the method includes administering to a subject in need thereof an effective amount of the composition described herein.

Another aspect of the disclosed technology relates to a method of accelerating wound healing, wheein the method includes administering to a subject in need thereof an effective amount of the composition described herein.

Another aspect of the disclosed technology relates to a method of treating or inhibiting progression a skin inflammation condition, wherein the method includes administering to a subject in need thereof an effective amount of the composition described herein.

Another aspect of the disclosed technology relates to a method of protecting skin from oxidation, wherein the method includes administering to a subject in need thereof an effective amount of the composition described herein. In some embodiments, the administration can reduce a concentration of reactive nitrogen species. In some embodiments, the administration can reduce a concentration of reactive oxygen species.

One aspect of the disclosed technology relates to a method of reducing the likelihood of skin cancer occurring in a subject, wherein the method includes administering to a subject in need thereof an effective amount of the composition described herein.

Another aspect of the disclosed technology relates to a method of treating or reducing liver damage from a toxin, wherein the method includes administering to a subject in need thereof an effective amount of the composition described herein.

One more aspect of the disclosed technology relates to a method of treating a liver disease, wherein the method includes administering to a subject in need thereof an effective amount of the composition described herein.

DETAILED DESCRIPTION OF THE PREFERRED EMBODIMENT

Figure 1:
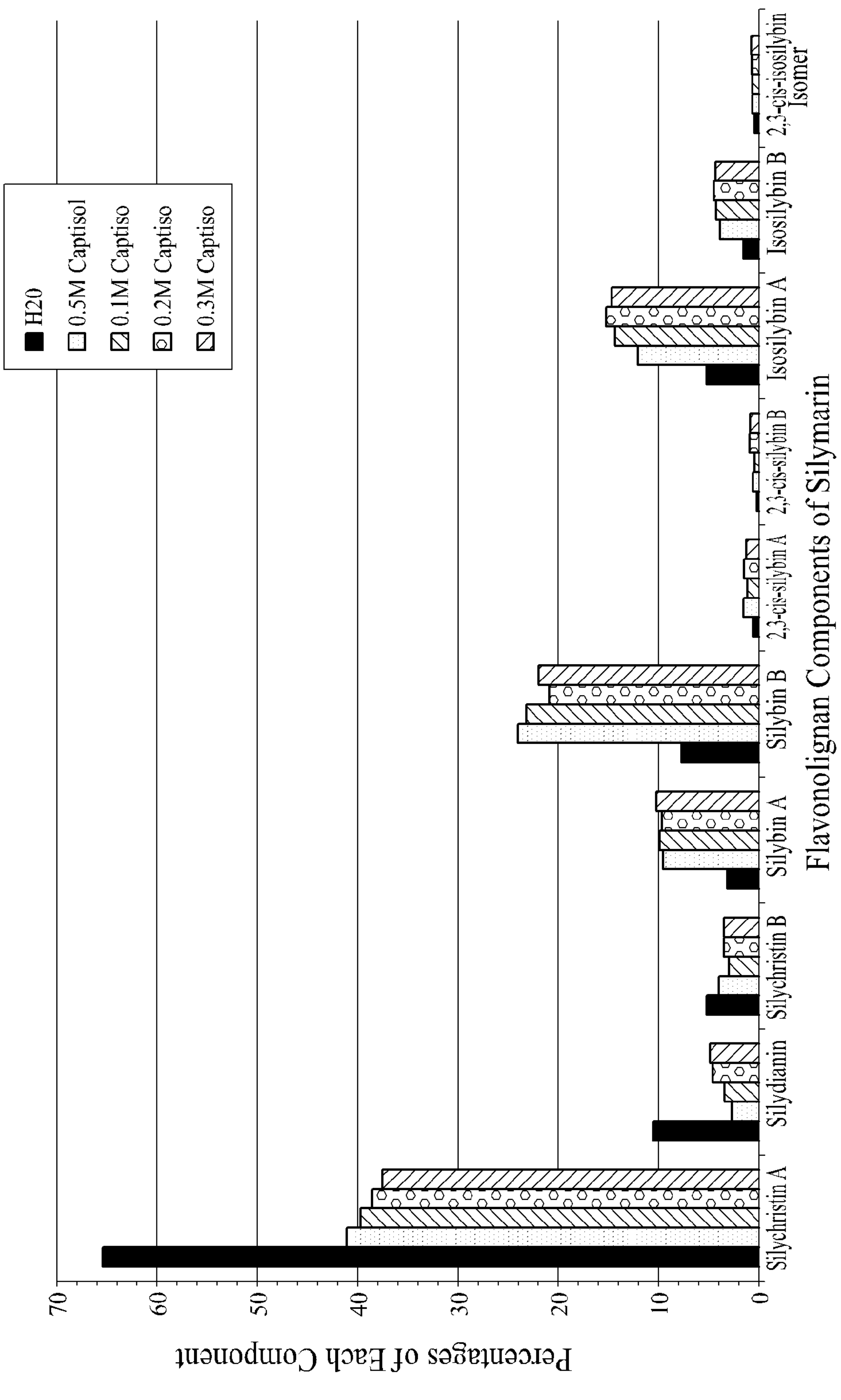
FIG. 1 shows the percentages of various components of silymarin in methanol standard (i.e. completely dissolved to 0.1 mg/ml), and upon saturated solubility in water, and 0.05M, 0.1M, 0.2M, and 0.3M solutions of sulfobutylether-β-cyclodextrin.

The term "silymarin" as used herein refers to the extract of the plant milk thistle and includes a mixture of chemicals isolated from the milk thistle. In some embodiments, silymarin includes silybin, isosilybin, silydianin, and silychristin. In some embodiments, silymarin includes approximately 70-80 percent silymarin flavonolignans such as silybin A, silybin B, isosilybin A, isosilybin B, silydianin, silychristin A, silychristin B, 2,3-cis-silybin A, 2,3-cis-silybin B, 2,3-cis-isosilybin isomer; and favonoids including taxifolin and quercetin, and the remaining 20-30 percent consisting of a chemically undefined fraction comprised of polymeric and oxidized polyphenolic compounds. Silybin is one of the active components of silymarin. In some embodiments, silybin includes silybin A, silybin B, 2,3-cis-silybin A, and 2,3-cis-silybin B. In some embodiments, silybin includes isosilybin A, isosilybin B, and 2,3-cis-isosilybin isomer.

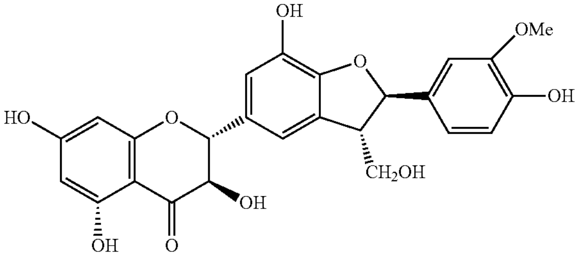

silychristin A

-continued

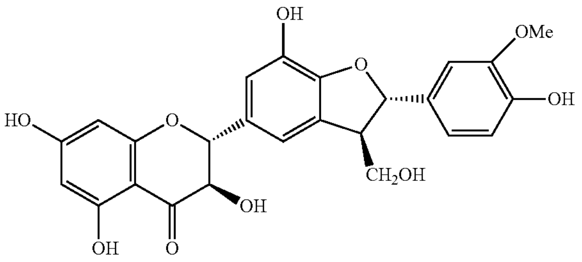

silychristin B

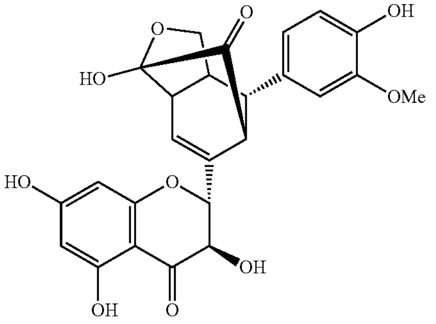

silydianin

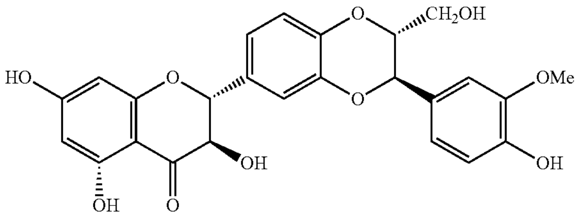

silybin A

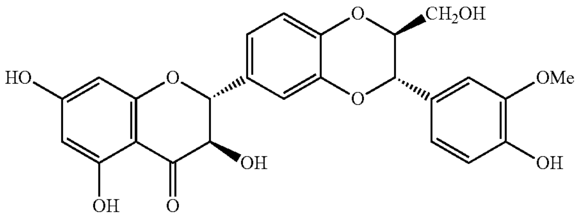

silybin B

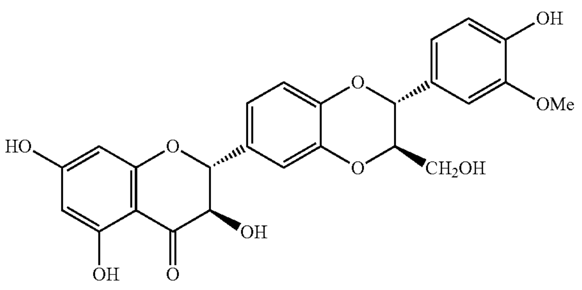

isosilybin A

-continued

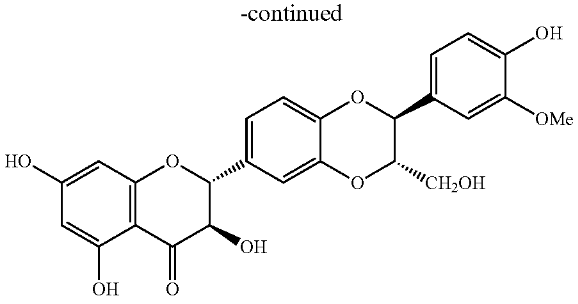

isosilybin B

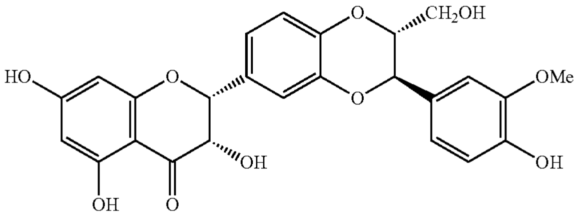

2,3-cis-silybin A

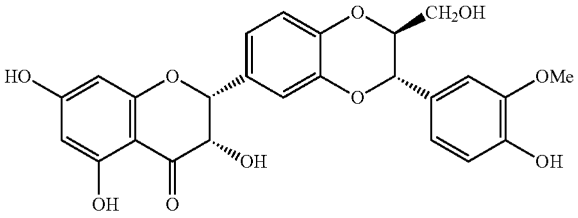

2,3-cis-silybin B

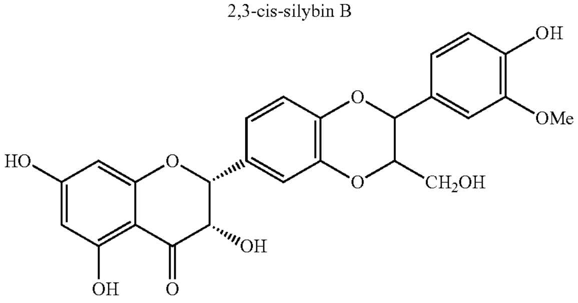

2,3-Cis-isosilybin isomer

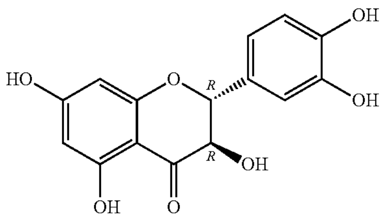

Taxifolin

The term "cosmetically acceptable," as used herein, means that the described or referenced compositions or components thereof are suitable for use in contact with mammalian skin tissue without undue toxicity, incompatibility, instability, allergic response, and the like.

The terms "smoothing" and "softening" as used herein mean altering the surface of the skin and/or keratinous tissue such that its tactile feel is improved. "Signs of skin aging" include, but are not limited to, all outwardly visible or tactilely perceptible manifestations as well as any other macro or micro effects due to skin aging. Such signs can be induced or caused by intrinsic factors or extrinsic factors, e.g., chronological aging and/or environmental damage.

These signs can result from processes that include, but are not limited to, the development of textural discontinuities such as wrinkles and coarse deep wrinkles, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including under eye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

The term "rejuvenating skin" includes increasing the health of skin, improving the appearance of skin, decreasing signs of skin aging, for example, decreasing the presence or appearance of wrinkles, fine lines or age spots or increasing the viability of skin cells. Typically the increase or decrease in the foregoing parameters will be at least: 5%, 10%, 20%, 50%, 100% or 150% compared to untreated skin which does not experience the present methods and compositions that rejuvenate skin.

"The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in World Patent Publication 87/05297, Johnston et al., published Sep. 11, 1987 (incorporated by reference herein).

The term "pharmaceutically acceptable cation" refers to cations that retain the biological effectiveness and properties of a compound and, which are not biologically or otherwise undesirable for use in a pharmaceutical. Examples of cation include but are not limited to sodium, potassium, lithium, ammonium, calcium, magnesium, iron, zinc, copper, manganese, aluminum, and the like; particularly preferred are the ammonium, potassium, sodium, calcium and magnesium cations. Other types of cations can include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such cations are known in the art, as described in WO 87/05297, Johnston et al., published Sep. 11, 1987 (incorporated by reference herein in its entirety).

Sulfoalkyl Ether Cyclodextrin

The terms "sulfoalkyl ether cyclodextrin" and "SAE-CD" as used herein refers to a cyclodextrin derivative containing a sulfoalkyl ether substituent, such as a ($C_{2-6}$ alkylene)-$SO_3^-$. The sulfoalkyl derivative of cyclodextrin can be a single derivative or a mixture of derivatives. Since the cyclodextrin derivatives contain sulfonyl groups, they can be charged species. The sulfoalkyl ether cyclodextrin can be either substituted at least at one of the primary hydroxyl groups of cyclodextrin or they are substituted at both the primary hydroxyl groups and at the 3-positioned hydroxyl group. Substitution at the 2-position is also possible. Examples of sulfoalkyl ether cyclodextrin include sulfobutyl ether β cyclodextrin.

In some embodiments, the sulfoalkyl ether cyclodextrin is a compound of Formula 1:

Formula 1

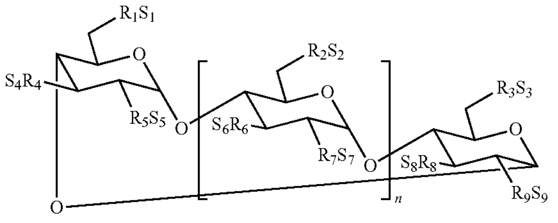

wherein n is 4, 5, or 6;

$R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group, wherein at least one of $R_1$ to $R_9$ is independently a —O—($C_2$-$C_6$ alkylene)-$SO_3^-$ group, a —O—$(CH_2)mSO_3^-$ group wherein m is 2 to 6, preferably 2 to 4, —$OCH_2CH_2CH_2SO_3^-$, or —$OCH_2CH_2CH_2CH_2$ $SO_3^-$; and $S_1$, $S_2$, $S_3$, $S_4$, $S_5$, $S_6$, $S_7$, $S_8$, and $S_9$, are each, independently, a pharmaceutically acceptable cation.

The terms "alkylene" and "alkyl," as used herein (e.g., as in the —O—($C_2$-$C_6$-alkylene)$SO_3^-$ group), include linear, cyclic, or branched, and saturated or unsaturated (i.e., containing one or more double bonds) divalent hydrocarbon groups.

Some embodiments provide compositions containing a single type of cyclodextrin derivative having the structure set out in formula (I), where the composition overall contains on the average at least 1 and up to 3n+6 alkylsulfonic acid moieties per cyclodextrin molecule. The compositions described herein also includes compositions containing cyclodextrin derivatives having a narrow or wide range for degree of substitution and high or low degree of substitution. These combinations can be optimized as needed to provide cyclodextrins having particular properties.

In some embodiments, the sulfobutyl ether cyclodextrin is a compound of Formula II:

Formula (II)

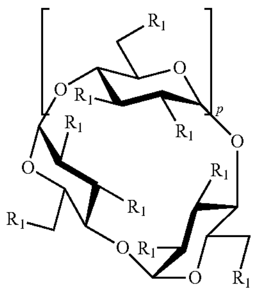

or a pharmaceutically acceptable salt thereof, wherein:

p is 4, 5, or 6, and each $R_1$ is independently —O—($C_1$-$C_8$ alkylene)-$SO_3T$ or —OH, and;

each T is independently hydrogen or pharmaceutically acceptable cation, provided that at least one $R_1$ is —OH.

In some embodiments of Formula (II), each $R_1$ is independently —OH or —O—($C_1$-$C_8$ alkylene)-$SO_3T$, provided that at least one $R_1$ is OH and at least one $R_1$ is —O—($C_1$-$C_8$ alkylene)-$SO_3T$, wherein T is a hydrogen or pharmaceutically acceptable cation. In some embodiments, at least one $R_1$ is independently —OH or —O—($C_4$ alkylene)-$SO_3T$. In some embodiments, at least one $R_1$ is independently a —O—$(CH_2)_gSO_3T$ group, wherein g is 2 to 6, or 2 to 4. In some embodiments, at least one $R_1$ is independently —$OCH_2CH_2CH_2SO_3T$ or —$OCH_2CH_2CH_2CH_2SO_3T$. In some embodiments, T is H. In some embodiments, T is $Na^+$. In some embodiments, each T is independently selected from an alkali metal, an alkaline earth metals, ammonium ions, and amine cations such as the, and combinations thereof. In some embodiments, each T is independently selected from $Li^+$, $Na^+$, $K^+$, $Ca^{+2}$, $Mg^{+2}$, amine, and any combination thereof. In some embodiments, each T is independently an amine cation selected from ($C_1$-$C_6$)-alkylamines, piperidine, pyrazine, ($C_1$-$C_6$)-alkanolamine, ethylenediamine and ($C_4$-$C_8$)-cycloalkanolamine.

In some embodiments, a sulfoalkyl ether cyclodextrin can have an average degree of substitution (ADS) of 2 to 9, 4 to 8, 4 to 7.5, 4 to 7, 4 to 6.5, 4.5 to 8, 4.5 to 7.5, 4.5 to 7, 5 to 8, 5 to 7.5, 5 to 7, 5.5 to 8, 5.5 to 7.5, 5.5 to 7, 5.5 to 6.5, 6 to 8, 6 to 7.5, 6 to 7.1, 6.5 to 7.1, 6.2 to 6.9, or 6.5 per cyclodextrin, and the remaining substituents are —H.

Exemplary SAE-CD derivatives include SBE4-β-CD, SBE7-β-CD, SBE11-β-CD, SBE7-γ-CD and SBE5-γ-CD which correspond to SAE-CD derivatives of the formula II wherein p=5, 5, 5, 6 and 6, respectively; and there are on average 4, 7, 11, 7 and 5 sulfoalkyl ether substituents present, respectively. Other exemplary SAE-CD derivatives include those of the formula SAEx-R-CD, wherein SAE is sulfomethyl ether (SME), sulfoethyl ether (SEE), sulfopropyl ether (SPE), sulfobutyl ether (SBE), sulfopentyl ether (SPtE), or sulfohexyl ether (SHE); x (average or specific degree of substitution) is 1-18, 1-21, or 1-24; R (ring structure of parent cyclodextrin) is α, β or γ, respectively; and CD is cyclodextrin. The SAE functional group includes a cationic counterion as disclosed herein or generally as used in the pharmaceutical industry for the counterion of any acidic group. Since SAE-CD is a poly-anionic cyclodextrin, it can be provided in different salt forms. Suitable counterions for the SAE functional group(s) include cationic organic atoms or molecules and cationic inorganic atoms or molecules. The SAE-CD can include a single type of counterion or a mixture of different counterions. The properties of the SAE-CD can be modified by changing the identity of the counterion present. For example, a first salt form of SAE-CD can have a greater electrostatic charge than a different second salt form of SAE-CD. The calcium salt form has been found to be more electronegative than the sodium salt form. Likewise, a SAE-CD having a first degree of substitution can have a greater electrostatic charge than a second SAE-CD having a different degree of substitution.

A sulfobutyl ether derivative of beta cyclodextrin (SBE-β-CD), in particular the derivative with an average of about 7 substituents per cyclodextrin molecule (SBE7-β-CD), has been commercialized by CyDex, Inc. as CAPTISOL®. CAPTISOL® has the following structure.

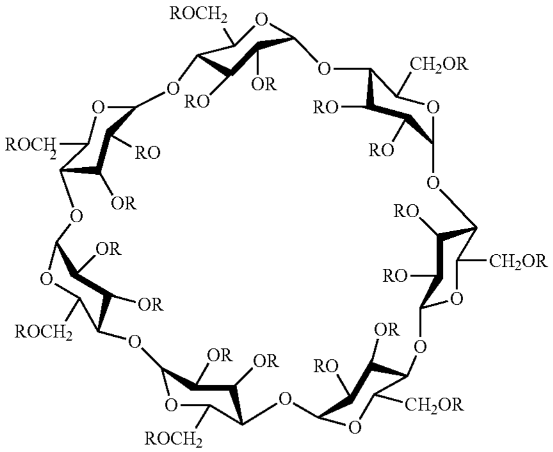

Sulfobutyl Ether-β-Cyclodextrin (CAPTISOL®)

R = (——$H)_{21-n}$ or (——$(CH_2)_4$—$SO_3Na)_n$ where n = 6.0-7.1

Exemplary SAE-CD derivatives include SBE4-β-CD, SBE7-β-CD, SBE11-β-CD, SBE7-γ-CD and SBE5-γ-CD which correspond to SAE-CD derivatives of the formula I wherein n=5, 5, 5, 6 and 6, respectively; m is 4; and there are on average 4, 7, 11, 7 and 5 sulfoalkyl ether substituents present, respectively. Other exemplary SAE-CD derivatives include those of the formula SAEx-R-CD (Formula 2), wherein SAE is sulfomethyl ether (SME), sulfoethyl ether (SEE), sulfopropyl ether (SPE), sulfobutyl ether (SBE), sulfopentyl ether (SPtE), or sulfohexyl ether (SHE); x (average or specific degree of substitution) is 1-18, 1-21, or 1-24; R (ring structure of parent cyclodextrin) is α, β or γ, respectively; and CD is cyclodextrin. The SAE functional group includes a cationic counterion as disclosed herein or generally as used in the pharmaceutical industry for the counterion of any acidic group. Since SAE-CD is a polyanionic cyclodextrin, it can be provided in different salt forms. Suitable counterions for the SAE functional group(s) include cationic organic atoms or molecules and cationic inorganic atoms or molecules. The SAE-CD can include a single type of counterion or a mixture of different counterions. The properties of the SAE-CD can be modified by changing the identity of the counterion present. For example, a first salt form of SAE-CD can have a greater electrostatic charge than a different second salt form of SAE-CD. The calcium salt form has been found to be more electronegative than the sodium salt form. Likewise, a SAE-CD having a first degree of substitution can have a greater electrostatic charge than a second SAE-CD having a different degree of substitution.

Methods of preparing SAE-CD derivatives are varied but generally include the general steps of sulfoalkylation followed by isolation. The chemical property profile of the SAE-CD is established during the sulfoalkylation step. For example, altering reaction conditions during sulfoalkylation can vary the average degree of substitution for and the average regiochemical distribution of sulfoalkyl groups in the SAE-CD. The alkyl chain length of the sulfoalkyl functional group is determined according the sulfoalkylating agent used. And use of a particular alkalizing agent during alkylation would result in formation of a particular SAE-CD salt, unless an ion exchange step were performed subsequent to sulfoalkylation.

In general, known processes for the sulfoalkylation step include, for example: 1) exposure of underivatized parent cyclodextrin under alkaline conditions to an alkylating agent, e.g. alkyl sultone or a haloalkylsulfonate; 2) optional addition of further alkalizing agent to the reaction milieu to consume excess alkylating agent; and 3) neutralization of the reaction medium with acidifying agent. The vast majority of literature processes conduct the sulfoalkylation step in aqueous media; however, some references disclose the use of pyridine, dioxane, or DMSO as the reaction solvent for sulfoalkylation. Literature discloses the use of an alkalizing agent in order to accelerate the sulfoalkylation reaction.

Upon completion of the sulfoalkylation step, isolation and purification of the SAE-CD is conducted.

Several different isolation processes for SAE-CD following sulfoalkylation and neutralization are described. In general, an aqueous liquid containing SAE-CD is dried to remove water to form a solid. The literature suggests various methods for removal of water from an aqueous solution containing SAE-CD. Such methods include conventional freeze-drying, spray drying, oven drying, vacuum oven drying, roto-evaporation under reduced pressure, vacuum drying or vacuum drum drying. See, for example, Ma (S.T.P. Pharma. Sciences (1999), 9(3), 261-266), CAPTISOL® (sulfobutyl ether beta-cyclodextrin sodium; Pharmaceutical Excipients 2004; Eds. R. C. Rowe, P. J. Sheskey, S. C. Owen; Pharmaceutical Press and American Pharmaceutical Association, 2004) and other references regarding the preparation of SAE-CD derivatives.

Suitable methods for preparing a SAE-CD-raw material for use in preparing the SAE-CD composition for use as described herein are disclosed in U.S. Pat. No. 5,376,645, 5,874,418, and 5,134,127 to Stella et al.; U.S. Pat. No. 3,426,011 to Parmerter et al.; Lammers et al. (Reel. Tray. CMm. Pays-Bas (1972), 91(6), 733-742); Staerke (1971), 23(5), 167-171); Qu et al. (J Inclusion Phenom. Macro. Chem., (2002), 43, 213-221); U.S. Pat. No. 5,241,059 to Yoshinaga; U.S. Pat. No. 6,153,746 to Shah; PCT International Publication No. WO 2005/042584 to Stella et al; Adam et al. (J. Med. Chem. (2002), 45, 1806-1816); PCT International Publication No. WO 01/40316 to Zhang et al.; Tarver et al. (Bioorganic & Medicinal Chemistry (2002), 10, 1819-1827); Ma (S.T.P. Pharma. Sciences (1999), 9(3), 261-266); Jung et al. (J Chromat. 1996, 755, 81-88); and Luna et al. (Carbohydr. Res. 1997, 299, 103-110), the entire disclosures of which are hereby incorporated by reference.

The SAE-CD raw material can be included in the liquid feed used in the fluidized bed spray drying process as described in U.S. Pat. No. 8,049,003, which is incorporated by reference for the purpose of preparing the SAE-CD composition through the fluidized bed spray drying process. Other methods for removal of water from an aqueous solution containing SAE-CD can include conventional freeze-drying, spray drying, oven drying, vacuum oven drying, roto-evaporation under reduced pressure, vacuum drying or vacuum drum drying. See, for example, Ma (*S.T.P. Pharma. Sciences* (1999), 9(3), 261-266), CAPTISOL® (sulfobutyl ether beta-cyclodextrin sodium; *Pharmaceutical Excipients* 2004; Eds. R. C. Rowe, P. J. Sheskey, S. C. Owen; Pharmaceutical Press and American Pharmaceutical Association, 2004), which is incorporated herein by reference in its entirety, and other references regarding the preparation of SAE-CD derivatives.

The SAE-CD composition described herein can also include a combination of derivatized cyclodextrin (SAE-CD) and underivatized cyclodextrin. For example, a SAE-CD composition can be made to include underivatized cyclodextrin in the amount of 0 to less than 50% by wt. of the total cyclodextrin present. Exemplary embodiments of the SAE-CD composition include those comprising 0-5% by wt., 5-50% by wt., less than 5%, less than 10%, less than 20%, less than 30%, less than 40%, or less than 50% underivatized cyclodextrin.

Compositions Containing Silymarin and Sulfoalkyl Ether Cyclodextrin

In some embodiments, sulfoalkyl ether cyclodextrin is used to increase the solubility and bioavailability of silymarin by forming inclusion complexes with one or more components of silymarin. To improve the solubility and bioavailability of silymarin and certain components of silymarin in an aqueous solution, a composition can be prepared to include silymarin or one or more components selected from silychristin A, silydianin, silychristin B, silybin A, silybin B, 2,3-cis-silybin A, 2,3-cis-silybin B, isosilybin A, isosilybin B, or 2,3-cis-isosilybin isomer; and sulfoalkyl ether cyclodextrin.

The composition can include silymarin or one or more selected components of silymarin. In some embodiments, the composition can include one or more component selected from taxifolin, silychristin A, silydianin, silychristin B, silybin A, silybin B, 2,3-cis-silybin A, 2,3-cis-silybin B, isosilybin A, isosilybin B, or 2,3-cis-isosilybin isomer. In some embodiments, the composition can include isosilybin B. In some embodiments, the composition includes isosilybin A. In some embodiments, the composition can include silybin A. In some embodiments, the composition can include silybin B. In some embodiments, the composition can include taxifolin.

The amount of silymarin or selected components of silymarin in the composition can vary depending on the use of the composition and the amount of other ingredients used in the composition. In some embodiments, the amount of silymarin or selected components of silymarin in the composition can be in the range of about 0.01% to about 2% by weight, about 0.01% to about 5%, 0.05% to about 10%, or about 0.1% to about 15%, based on the total weight of composition. In some embodiments, the amount of silymarin or selected components of silymarin in the composition can be in the range of about 0.1% to about 1.5% by weight, about 0.1% to about 1%, 0.1% to about 0.5%, or about 0.1% to about 0.4%, based on the total weight of composition. In some embodiments, the amount of silymarin can be in the range of about 0.1% to about 1%, about 0.1% to about 0.5%, about 0.3% to about 0.5% by weight based on the total weight of the composition. In some embodiments, the amount of silymarin can be about 0.1%, 0.2%, 0.3%, 0.4%, or 0.5% by weight of the total weight of the composition. In some embodiments, the amount of silymarin can be about 0.4% by weight of the total weight of the composition.

The amount of sulfoalkyl ether cyclodextrin in the composition can vary depending on the amount of silymarin or selected silymarin components and the use of other ingredients in the composition. In some embodiments, the amount of sulfoalkyl ether cyclodextrin in the composition can be in the range of 1% to about 20% by weight, about 1% to about 30%, 1% to about 40%, or about 1% to about 50%, based on the total weight of composition. In some embodiments, the amount of sulfoalkyl ether cyclodextrin in the composition can be in the range of about 1% to about 15% by weight, about 5% to about 15%, 10% to about 15%, or about 10% to about 14%, based on the total weight of composition. In some embodiments, the amount of sulfoalkyl ether cyclodextrin in the composition can be in the range of about 1% to about 20%, about 1% to about 18%, about 5% to about 16%, about 5% to about 15%, about 10% to about 14%, about 10% to about 13.5% by weight, based on the total weight of the composition. In some embodiments, the amount of sulfoalkyl ether cyclodextrin in the composition can be about 10%, 11%, 12%, 13%, 14%, 15%, 16%, or 20% by weight, based on the total weight of the composition. In some embodiments, the amount of sulfoalkyl ether cyclodextrin in the composition can be about 13% by weight, based on the total weight of the composition.

The mass ratio of silymarin to sulfoalkyl ether cyclodextrin can vary based on other components added to the composition. In some embodiments, the mass ratio of silymarin to sulfoalkyl ether cyclodextrin can be in the range of about 1:100 to about 10:1, about 1:50 to about 10:1, about 1:40 to about 10:1, or about 1:30 to about 10:1. In some embodiments, the mass ratio of silymarin to sulfoalkyl ether cyclodextrin can be about 2:100 to about 5:1, about 2:90 to about 5:1, about 2:80 to about 5:1, about 2:75 to about 5:1, or about 2:70 to about 5:1. In some embodiments, the mass ratio of silymarin to sulfoalkyl ether cyclodextrin can be about 1:45 to about 1:25, about 1:40 to about 1:30, or about 1:40 to about 1:35. In some embodiments, the mass ratio of silymarin to sulfoalkyl ether cyclodextrin can be about 1:40, 1:39, 1:38, 1:37, 1:36, 1:35, or 2:75. In some embodiments, the mass ratio of silymarin to sulfoalkyl ether cyclodextrin can be about 2:75.

The sulfoalkyl ether cyclodextrin silymarin composition described herein can be in the form of a gel. In some embodiments, the gel formulation may further comprise a solvent. In some embodiments, the solvent may be selected from dimethyl isosorbide (e.g. Arlasolve®), benzyl alcohol, deionized water, dimethicone, ethanol, glycerol, isopropyl alcohol, isopropyl palmitate, In some embodiments, the gel may further comprise a color, a fragrance, a pearling agent, an antioxidant, a surfactant, a preservative, a solubilizer, an emulsion stabilizer, a pH adjuster, a chelating agent, a viscosity modifier, an emollient, an opacifying agent, a skin conditioning agent, a buffer system or combinations thereof.

In some embodiments, the gel composition may comprise an antimicrobial preservative agent. In embodiments, the preservative agent may be alcohol, benzalkonium chloride, benzoic acid, centrimide, chlorocresol, chlorobutanol, glycerin, phenylmercuric acetate, phenylmercuric nitrate, propylene glycol, sodium benzoate, sorbic acid, thimersol, phenoxyethanol, methylparaben, ethylparaben, butylparaben, propylparaben, potassium sorbate, benzyl alcohol or a combination thereof.

In some embodiments, the gel composition may comprise a gelling agent. In embodiments, the gelling agent may be a carbomer or a carbomer copolymer. In embodiments, the gelling agent may be carbopol; hydropropyl methylcellulose, polycarbophil, hydroxyethyl cellulose, hydroxypropyl cellulose, or a combination thereof.

In some embodiments, the gel may include an emulsifying agent, or emulsifier. The emulsifier can be provided to adjust the properties of the gel, such as density, viscosity, the melting point, and/or droplet size; and in some embodiments, the emulsifier may increase the stability of the gel. Various emulsions suitable for embodiments described herein and methods for preparing such emulsions are well known in the art and are described in, for example, Remington's Pharmaceutical Sciences, Mack Publishing Co., Easton, Pa., USA, which is hereby incorporated by reference in its entirety. In some embodiments, the gel may include an emulsifier in an amount from about 0.1% to about 30%, from about 0.1% to about 25%, from about 0.1% to about 20%, or from about 0.5% to about 12% emulsifier. In some embodiments, the gel may include emulsifier in an amount less than 20%. In other embodiments, the gel may include from about 0.5% to about 10% emulsifier. In still other embodiments, the gel may include from about 0.5% to less than about 20% emulsifier. If more than one emulsifier is used, the gel may include from about 0.1% to about 20% of each emulsifier.

In an embodiment, the gel formulation may be emulsified. In some embodiment, the gel may be non-emulsified. The gels of various embodiments may include an emulsifier or combination of emulsifiers. In some embodiments, the gel may include one or more emulsifiers selected from fatty alcohols such as, without limitation, stearyl alcohol; nonionic emulsifiers such as, without limitation, glyceryl monostearate, or polyoxyethylene castor oil derivatives; PEG-400, PEG-80 sorbitan laurate, steareth, PEG-100 stearate, laureth-23, polysorbate 20 NF, polysorbate 20, isoceteth, ceteth, steareth-21, steareth-20, oleth-20, ceteareth-20, PEG-20 methyl clucose sesquistearate, polysorbate 80, PEG-60 almond glycerides, isosteareth-20, polysorbate 80, polysorbate 60, polysorbate 60 NF, cocamide MEA, PEG-8 laurate, ceteth-10, oleth-10/polyoxyl 10 oleyl ether, oleth-10, polyglyceryl-3 methyglucose distearate, PEG-8 oleate, cetearyl glucoside, PEG-7 olivate, polysorbate 85, glyceryl stearate, PEG-100 stearate, stearamide MEA, PEG-25 hydrogenated castor oil, glyceryl laurate, ceteth-2, PEG-30 dipolyhydroxystearate, glyceryl stearate SE, sorbitan stearate, sucrose cocoate, PEG-4 dilaurate, methyl glucose sesquistearate, lecithin, PEG-8 dioleate, sorbitan laurate, PEG-40 sorbitan peroleate, laureth-4, PEG-7 glyceryl cocoate, PEG-20 almond glycerides, or any combination thereof. In embodiments, the gel may include one or more emulsifiers, such as, for example, poloxamer 407, sesquioleates such as sorbitan sesquioleate or polyglyceryl-2-sesquioleate, ethoxylated esters of derivatives of natural oils such as the polyethoxylated ester of hydrogenated castor oil, silicone emulsifiers such as silicone polyols, anionic emulsifiers, fatty acid soaps such as potassium stearate and fatty acid sulphates like sodium cetostearyl sulphate, ethoxylated fatty alcohols, sorbitan esters, ethoxylated sorbitan esters, ethoxylated fatty acid esters such as ethoxylated stearates, ethoxylated mono, di-, and triglycerides, non-ionic self-emulsifying waxes, ethoxylated fatty acids, methylglucose esters such as polyglycerol-3 methyl glucose distearate, or a combination thereof. In particular embodiments, the emulsifier may be polyaxmer 407, which may be marketed under the trademark Lutrol® F127.

The gels of various embodiments may include any number of additional components such as, for example, silicones, preservatives, emulsion stabilizers, pH adjusters, chelating agents, viscosity modifiers, antioxidants, surfactants, emollients, opacifying agents, skin conditioners, buffers, and combinations thereof. In some embodiments, such additional components may provide a dual purpose. For example, certain surfactants may also act as emulsifiers, certain emollients may also act as opacifying agents, and certain buffering agents may also act as chelating agents.

In some embodiments, the composition described herein can include phenoxyethanol, ethanol, PEG 400, and hydroxypropyl cellulose. In some embodiments, the composition described herein can include phenoxyethanol, ethanol, PEG 400, hydroxypropyl cellulose, and deionized water.

The amount of phenoxyethanol or other preservative agent in the composition can vary depending on the amount of silymarin or selected silymarin components and the use of other ingredients in the composition. In some embodiments, the amount of phenoxyethanol or other preservative agent in the composition can be in the range of 0.001% to about 20%, about 0.01% to about 10%, 0.1% to about 10%, or about 0.5% to about 5%, by weight, based on the total weight of composition. In some embodiments, the amount of phenoxyethanol or other preservative agent in the composition can be about 0.1%, 0.2%, 0.5%, 0.7%, 1%, 1.2%, 1.5%, 1.7%, 2%, 2.5%, or 5% by weight, based on the total weight of composition. In some embodiments, the amount of phenoxyethanol or other preservative agent in the composition can be about 1% by weight, based on the total weight of composition.

The amount of ethanol or other organic solvent in the composition can vary depending on the amount of silymarin or selected silymarin components and the use of other ingredients in the composition. In some embodiments, the amount of ethanol or other organic solvent in the composition can be in the range of 1% to about 50%, about 1% to about 30%, 1% to about 20%, about 1% to about 15%, or about 5% to about 15%, by weight, based on the total weight of composition. In some embodiments, the amount of ethanol or organic other solvent in the composition can be about 1%, 2%, 5%, 7%, 10%, 12%, 15%, 17%, 20%, 25%, or 30% by weight, based on the total weight of composition. In some embodiments, the amount of ethanol or other organic solvent in the composition can be about 10% by weight, based on the total weight of composition.

The amount of PEG 400 or other emulsifier in the composition can vary depending on the amount of silymarin or selected silymarin components and the use of other ingredients in the composition. In some embodiments, the amount of PEG 400 or other emulsifier in the composition can be in the range of 1% to about 60%, about 1% to about 50%, 1% to about 40%, about 1% to about 30%, about 5% to about 30%, or about 5% to about 25% by weight, based on the total weight of composition. In some embodiments, the amount of PEG 400 or other emulsifier in the composition can be about 5%, 7%, 10%, 12%, 15%, 17%, 20%, 25%, 28%, 30%, 35% or 40% by weight, based on the total weight of composition. In some embodiments, the amount of PEG 400 or other emulsifier in the composition can be about 20% by weight, based on the total weight of composition.

The amount of water in the composition can vary depending on the amount of silymarin or selected silymarin components and the use of other ingredients in the composition. In some embodiments, the amount of water in the composition can be in the range of 1% to about 95%, about 1% to about 90%, 1% to about 85%, about 1% to about 80%, about 5% to about 80%, or about 50% to about 75% by weight, based on the total weight of composition. In some embodiments, the amount of water in the composition can be about 10%, 20%, 25%, 30%, 35%, 40%, 45%, 50%, 51%, 52%, 53%, 54%, 55%, 56%, 57%, 60%, 64%, 65%, 66%, 67%, 68%, 69%, 70%, 75%, 80%, or 85% by weight, based on the total weight of composition. In some embodiments, the amount of water in the composition can be about 54% by weight, based on the total weight of composition.

The amount of gelling agent (e.g., hydroxypropyl cellulose or hydroxyethyl cellulose) in the composition can vary depending on the amount of silymarin or selected silymarin components and the use of other ingredients in the composition. In some embodiments, the amount of hydroxypropyl cellulose or other gelling agent in the composition can be in the range of 0.001% to about 20%, about 0.01% to about 10%, 0.1% to about 10%, or about 0.5% to about 5% by weight, based on the total weight of composition. In some embodiments, the amount of hydroxypropyl cellulose or other gelling agent in the composition can be about 0.1%, 0.2%, 0.5%, 0.7%, 1%, 1.2%, 1.5%, 1.7%, 2%, 2.5%, or 5% by weight, based on the total weight of composition. In some embodiments, the amount of hydroxypropyl cellulose or other gelling agent in the composition can be 1% by weight, based on the total weight of composition.

The molar ratio of the isosilybin B and sulfoalkyl ether cyclodextrin can be adjusted based on the use of the composition and the amount of other components added. In some embodiments, the molar ratio of the isosilybin B and sulfoalkyl ether cyclodextrin can be in the range of about 0.00001:1 to about 100:1, about 0.00005:1 to about 50:1; about 0.0001:1 to about 10:1; about 0.005:1 to about 5:1; about 0.001:1 to about 1:1. In some embodiments, the molar ratio of the isosilybin B and sulfoalkyl ether cyclodextrin can be in the range of about 0.00001:1 to about 100:1. In some embodiments, the molar ratio of the isosilybin B and sulfoalkyl ether cyclodextrin can be in the range of about 0.00001:1 to about 100:1. In some embodiments, the molar ratio of the isosilybin B and sulfoalkyl ether cyclodextrin can be in the range of about 0.00005:1 to about 50:1. In some embodiments, the molar ratio of the isosilybin B and sulfoalkyl ether cyclodextrin can be in the range of about 0.0001:1 to about 10:1. In some embodiments, the molar ratio of the isosilybin B and sulfoalkyl ether cyclodextrin can be in the range of about 0.005:1 to about 5:1. In some embodiments, the molar ratio of the isosilybin B and sulfoalkyl ether cyclodextrin can be in the range of about 0.001:1 to about 1:1. In some embodiments, the molar ratio of the isosilybin B and sulfoalkyl ether cyclodextrin can be no more than about 100, no more than about 10, no more than about 5, no more than about 2, no more than about 1, no more than about 0.5, no more than about 0.25, no more than about 0.1, no more than about 0.05, no more than about 0.01, no more than about 0.005, or no more than about 0.001. In some embodiments, the molar ratio of the isosilybin B and sulfoalkyl ether cyclodextrin can be no less than about 1, no less than about 0.5, no less than about 0.25, no less than about 0.1, no less than about 0.05, no less than about 0.01, no less than about 0.005, or no less than about 0.001.

The molar ratio of the isosilybin A and sulfoalkyl ether cyclodextrin can be adjusted based on the use of the composition and the amount of other components added. In some embodiments, the molar ratio of the isosilybin A and sulfoalkyl ether cyclodextrin can be in the range of about 0.00001:1 to about 100:1, about 0.00005:1 to about 50:1; about 0.0001:1 to about 10:1; about 0.005:1 to about 5:1; about 0.001:1 to about 1:1. In some embodiments, the molar ratio of the isosilybin A and sulfoalkyl ether cyclodextrin can be in the range of about 0.00001:1 to about 100:1. In some embodiments, the molar ratio of the isosilybin A and sulfoalkyl ether cyclodextrin can be in the range of about 0.00001:1 to about 100:1. In some embodiments, the molar ratio of the isosilybin A and sulfoalkyl ether cyclodextrin can be in the range of about 0.00005:1 to about 50:1. In some embodiments, the molar ratio of the isosilybin A and sulfoalkyl ether cyclodextrin can be in the range of about 0.0001:1 to about 10:1. In some embodiments, the molar ratio of the isosilybin A and sulfoalkyl ether cyclodextrin can be in the range of about 0.005:1 to about 5:1. In some embodiments, the molar ratio of the isosilybin A and sulfoalkyl ether cyclodextrin can be in the range of about 0.001:1 to about 1:1. In some embodiments, the molar ratio of the isosilybin A and sulfoalkyl ether cyclodextrin can be no more than about 100, no more than about 10, no more than about 5, no more than about 2, no more than about 1, no more than about 0.5, no more than about 0.25, no more than about 0.1, no more than about 0.05, no more than about 0.01, no more than about 0.005, or no more than about 0.001. In some embodiments, the molar ratio of the isosilybin A and sulfoalkyl ether cyclodextrin can be no less than about 1, no less than about 0.5, no less than about 0.25, no less than about 0.1, no less than about 0.05, no less than about 0.01, no less than about 0.005, or no less than about 0.001.

The molar ratio of the silybin A and sulfoalkyl ether cyclodextrin can be adjusted based on the use of the composition and the amount of other components added. In some embodiments, the molar ratio of the silybin A and sulfoalkyl ether cyclodextrin can be in the range of about 0.00001:1 to about 100:1, about 0.00005:1 to about 50:1; about 0.0001:1 to about 10:1; about 0.005:1 to about 5:1; about 0.001:1 to about 1:1. In some embodiments, the molar ratio of the silybin A and sulfoalkyl ether cyclodextrin can be in the range of about 0.00001:1 to about 100:1. In some embodiments, the molar ratio of the silybin A and sulfoalkyl ether cyclodextrin can be in the range of about 0.00001:1 to about 100:1. In some embodiments, the molar ratio of the silybin A and sulfoalkyl ether cyclodextrin can be in the range of about 0.00005:1 to about 50:1. In some embodiments, the molar ratio of the silybin A and sulfoalkyl ether cyclodextrin can be in the range of about 0.0001:1 to about 10:1. In some embodiments, the molar ratio of the silybin A and sulfoalkyl ether cyclodextrin can be in the range of about 0.005:1 to about 5:1. In some embodiments, the molar ratio of the silybin A and sulfoalkyl ether cyclodextrin can be in the range of about 0.001:1 to about 1:1. In some embodiments, the molar ratio of the silybin A and sulfoalkyl ether cyclodextrin can be no more than about 100, no more than about 10, no more than about 5, no more than about 2, no more than about 1, no more than about 0.5, no more than about 0.25, no more than about 0.1, no more than about 0.05, no more than about 0.01, no more than about 0.005, or no more than about 0.001. In some embodiments, the molar ratio of the silybin A and sulfoalkyl ether cyclodextrin can be no less than about 1, no less than about 0.5, no less than about 0.25, no less than about 0.1, no less than about 0.05, no less than about 0.01, no less than about 0.005, or no less than about 0.001.

The molar ratio of the silybin B and sulfoalkyl ether cyclodextrin can be adjusted based on the use of the composition and the amount of other components added. In some embodiments, the molar ratio of the silybin B and sulfoalkyl ether cyclodextrin can be in the range of about 0.00001:1 to about 100:1, about 0.00005:1 to about 50:1; about 0.0001:1 to about 10:1; about 0.005:1 to about 5:1; about 0.001:1 to about 1:1. In some embodiments, the molar ratio of the silybin B and sulfoalkyl ether cyclodextrin can be in the range of about 0.00001:1 to about 100:1. In some embodiments, the molar ratio of the silybin B and sulfoalkyl ether cyclodextrin can be in the range of about 0.00001:1 to about 100:1. In some embodiments, the molar ratio of the silybin B and sulfoalkyl ether cyclodextrin can be in the range of about 0.00005:1 to about 50:1. In some embodiments, the molar ratio of the silybin B and sulfoalkyl ether cyclodextrin can be in the range of about 0.0001:1 to about 10:1. In some embodiments, the molar ratio of the silybin B and sulfoalkyl ether cyclodextrin can be in the range of about 0.005:1 to about 5:1. In some embodiments, the molar ratio of the silybin B and sulfoalkyl ether cyclodextrin can be in the range of about 0.001:1 to about 1:1. In some embodiments, the molar ratio of the silybin B and sulfoalkyl ether cyclodextrin can be no more than about 100, no more than about 10, no more than about 5, no more than about 2, no more than about 1, no more than about 0.5, no more than about 0.25, no more than about 0.1, no more than about 0.05, no more than about 0.01, no more than about 0.005, or no more than about 0.001. In some embodiments, the molar ratio of the silybin B and sulfoalkyl ether cyclodextrin can be no less than about 1, no less than about 0.5, no less than about 0.25, no less than about 0.1, no less than about 0.05, no less than about 0.01, no less than about 0.005, or no less than about 0.001.

In some embodiments, the molar ratio of the taxifolin and sulfoalkyl ether cyclodextrin can be in the range of about 0.0001:1 to about 100:1, about 0.0005:1 to about 50:1; about 0.001:1 to about 10:1; about 0.002:1 to about 5:1; about 0.005:1 to about 1:1; about 0.001:1 to about 1:1. In some embodiments, the molar ratio of the taxifolin to sulfoalkyl ether cyclodextrin can be no more than about no more than about 5, no more than about 2, no more than about 1, no more than about 0.5, no more than about 0.25, no more than about 0.1, no more than about 0.05, no more than about 0.01, no more than about 0.005, no more than 0.0025, or no more than about 0.001. In some embodiments, the molar ratio of the taxifolin and sulfoalkyl ether cyclodextrin can be about 1, about 0.5, about 0.25, about 0.1, about 0.05, about 0.01, about 0.005, about 0.0025, or about 0.001.

In some embodiments, the mass ratio of the taxifolin and all flavonolignan components can be in the range of about 0.001:1 to about 100:1, about 0.005:1 to about 50:1; about 0.01:1 to about 10:1; about 0.05:1 to about 5:1; or about 0.1:1 to about 1:1. In some embodiments, the mass ratio of the taxifolin and all flavonolignan components can be no more than about 100, no more than about 10, no more than about 5, no more than about 2, no more than about 1, no more than about 0.5, no more than about 0.25, no more than about 0.1, no more than about 0.05, no more than about 0.01, no more than about 0.005, or no more than about 0.001. In some embodiments, the mass ratio of the taxifolin and all flavonolignan components can be no less than about 1, no less than about 0.5, no less than about 0.25, no less than about 0.1, no less than about 0.05, no less than about 0.01, no less than about 0.005, or no less than about 0.001.

In some embodiments, the molar ratio of the taxifolin and all flavonolignan components can be in the range of about 1:1 to about 100:1, about 1 to about 50:1; about 1:1 to about 20:1; about 5:1 to about 17:1; or about 5:1 to about 15:1. In some embodiments, the molar ratio of the taxifolin and all flavonolignan components can be no more than about 5, no more than about 2, no more than about 1, no more than about 0.5, no more than about 0.25, no more than about 0.1, no more than about 0.05, no more than about 0.01, no more than about 0.005, or no more than about 0.001. In some embodiments, the molar ratio of the taxifolin and all flavonolignan components can be about 0.01, 0.02, 0.04, 0.05, 0.06, or 0.07.

In some embodiments, the mass ratio of the taxifolin and all flavonolignan components can be in the range of about 1:1 to about 100:1, about 1 to about 50:1; about 1:1 to about 20:1; about 5:1 to about 17:1; or about 5:1 to about 15:1. In some embodiments, the mass ratio of the taxifolin and all flavonolignan components can be no more than about 5, no more than about 2, no more than about 1, no more than about 0.5, no more than about 0.25, no more than about 0.1, no more than about 0.05, no more than about 0.01, no more than about 0.005, or no more than about 0.001. In some embodiments, the mass ratio of the taxifolin and all flavonolignan components can be about 0.01, 0.02, 0.04, 0.05, 0.06, or 0.07.

The concentration of silymarin in the composition can vary depending on the amount of sulfoalkyl ether cyclodextrin, the process used to prepare the silymarin extract, the preparation temperature, and other components used in the composition. In some embodiments, the concentration of silymarin in the composition can be in the range of about 1 mg/ml to about 150 mg/ml, about 1 mg/ml to about 120 mg/ml, about 1 mg/ml to about 100 mg/ml, about 1 mg/ml to about 80 mg/ml, about 1 mg/ml to about 60 mg/ml, about 1 mg/ml to about 50 mg/ml, about 1 mg/ml to about 40 mg/ml, about 1 mg/ml to about 30 mg/ml, about 1 mg/ml to about 20 mg/ml, about 1 mg/ml to about 15 mg/ml, about 1 mg/ml to about 10 mg/ml, about 1 mg/ml to about 5 mg/ml, about 1 mg/ml to about 2.5 mg/ml, or about 1 mg/ml to about 1.5 mg/ml. In some embodiments, the concentration of silymarin in the composition can be in the range of about 10 mg/ml to about 100 mg/ml, about 10 mg/ml to about 90 mg/ml, about 10 mg/ml to about 80 mg/ml, about 10 mg/ml to about 70 mg/ml, about 10 mg/ml to about 60 mg/ml, about 10 mg/ml to about 50 mg/ml, about 10 mg/ml to about 40 mg/ml, about 10 mg/ml to about 30 mg/ml, or about 10 mg/ml to about 25 mg/ml. In some embodiments, the concentration of silymarin in the composition can be in the range of about 20 mg/ml to about 150 mg/ml, 20 mg/ml to about 100 mg/ml, about 20 mg/ml to about 90 mg/ml, about 20 mg/ml to about 80 mg/ml, about 20 mg/ml to about 70 mg/ml, about 20 mg/ml to about 60 mg/ml, about 20 mg/ml to about 50 mg/ml, about 20 mg/ml to about 40 mg/ml, about 20 mg/ml to about 30 mg/ml, or about 20 mg/ml to about 25 mg/ml. In some embodiments, the concentration of silymarin in the composition can be more than 1 mg/ml, 5 mg/ml, 8 mg/ml, 10 mg/ml, 15 mg/ml, 20 mg/ml, 25 mg/ml, 30 mg/ml, 40 mg/ml, 50 mg/ml, 60 mg/ml, or 70 mg/ml. In some embodiments, the concentration of silymarin in the composition can be less than 200 mg/ml, 150 mg/ml, 100 mg/ml, 80 mg/ml, 70 mg/ml, or 50 mg/ml. In some embodiments, the concentration of silymarin in the composition can be about 24 mg/ml, about 37 mg/ml, about 65 mg/ml, or about 72 mg/ml.

The concentration of sulfoalkyl ether cyclodextrin in the composition can vary depending on the amount of silymarin or the amount of one or more component of silymarin used in the composition. In some embodiments, the concentration of sulfoalkyl ether cyclodextrin in the composition can be in the range of about 0.001 mol/L to about 50 mol/L, about 0.001 mol/L to about 25 mol/L, about 0.001 mol/L to about 10 mol/L, about 0.001 mol/L to about 5 mol/L, about 0.001 mol/L to about 1 mol/L, about 0.001 mol/L to about 0.8 mol/L, about 0.001 mol/L to about 0.5 mol/L, about 0.001 mol/L to about 0.4 mol/L, about 0.001 mol/L to about 0.3 mol/L, about 0.001 mol/L to about 0.2 mol/L, or about 0.001 mol/L to about 0.1 mol/L. In some embodiments, the concentration of sulfoalkyl ether cyclodextrin in the composition can be in the range of about 0.001 mol/L to about 2 mol/L, about 0.002 mol/L to about 2 mol/L, about 0.004 mol/L to about 2 mol/L, about 0.005 mol/L to about 2 mol/L, about 0.006 mol/L to about 2 mol/L, about 0.008 mol/L to about 2 mol/L, about 0.009 mol/L to about 2 mol/L, about 0.01 mol/L to about 2 mol/L, about 0.015 mol/L to about 2 mol/L, about 0.02 mol/L to about 2 mol/L, about 0.025 mol/L to about 2 mol/L, about 0.03 mol/L to about 2 mol/L, about 0.035 mol/L to about 2 mol/L, about 0.04 mol/L to about 2 mol/L, about 0.045 mol/L to about 2 mol/L, about 0.05 mol/L to about 2 mol/L, about 0.1 mol/L to about 2 mol/L, about 0.15 mol/L to about 2 mol/L, about 0.2 mol/L to about 2 mol/L, about 0.25 mol/L to about 2 mol/L, about 0.3 mol/L to about 2 mol/L, about 0.35 mol/L to about 2 mol/L, about 0.4 mol/L to about 2 mol/L, about 0.45 mol/L to about 2 mol/L, about 0.5 mol/L to about 2 mol/L, about 0.6 mol/L to about 2 mol/L, about 0.07 mol/L to about 2 mol/L, about 0.9 mol/L to about 2 mol/L, or about 1.0 mol/L to about 2 mol/L. In some embodiments, the concentration of sulfoalkyl ether cyclodextrin in the composition can be in the range of about 0.002 mol/L to about 1 mol/L, about 0.004 mol/L to about 1 mol/L, about 0.005 mol/L to about 1 mol/L, about 0.006 mol/L to about 1 mol/L, about 0.008 mol/L to about 1 mol/L, about 0.009 mol/L to about 1 mol/L, about 0.01 mol/L to about 1 mol/L, about 0.015 mol/L to about 1 mol/L, about 0.02 mol/L to about 1 mol/L, about 0.025 mol/L to about 1 mol/L, about 0.03 mol/L to about 1 mol/L, about 0.035 mol/L to about 1 mol/L, about 0.04 mol/L to about 1 mol/L, about 0.045 mol/L to about 1 mol/L, about 0.05 mol/L to about 1 mol/L, about 0.1 mol/L to about 1 mol/L, about 0.15 mol/L to about 1 mol/L, about 0.2 mol/L to about 1 mol/L, about 0.25 mol/L to about 1 mol/L, about 0.3 mol/L to about 1 mol/L, about 0.35 mol/L to about 1 mol/L, about 0.4 mol/L to about 1 mol/L, about 0.45 mol/L to about 1 mol/L, about 0.5 mol/L to about 1 mol/L, about 0.6 mol/L to about 1 mol/L, about 0.07 mol/L to about 1 mol/L, or about 0.9 mol/L to about 1 mol/L. In some embodiments, the concentration of sulfoalkyl ether cyclodextrin in the composition can be in the range of about 0.01 mol/L to about 0.5 mol/L, about 0.01 mol/L to about 0.4 mol/L, about 0.01 mol/L to about 0.3 mol/L, or about 0.01 mol/L to about 0.2 mol/L.

The presence of sulfoalkyl ether cyclodextrin can help selectively enrich a component of silymarin and increase the weight percentage of the component in silymarin mixture. For example, the presence of sulfoalkyl ether cyclodextrin can help selectively increase the percentage of silybin. More particularly, the presence of sulfoalkyl ether cyclodextrin can help selectively increase the percentages of taxifolin, silybin A, silybin B, isosilybin A, isosilybin B, or other silybin isomers in the silymarin mixture.

In some embodiments, the amount of taxifolin can be in the range of about 0.5% to about 10%, about 1% to about 8%, about 2% to about 6%, about 2.5% to about 5%, about 2.5% to about 4%, about 3% to about 4% of the total weight of all silymarin components or the combined weight of taxifolin and the ten flavonolignan components (silybin A, silybin B, isosilybin A, isosilybin B, silydianin, silychristin A, silychristin B, 2,3-cis-silybin A, 2,3-cis-silybin B, 2,3-cis-isosilybin isomer) described herein. In some embodiments, the amount of taxifolin can be about 1%, 2%, 3%, 3.5%, 4%, 5%, or 6% of the total weight of all silymarin components or the combined weight of taxifolin and the ten flavonolignan components described herein.

In some embodiments, the presence of sulfoalkyl ether cyclodextrin can selectively increase the percentage of silybin A in silymarin by about more than 1%, 2%, 3%, 4%, 5%, 6%, 7%, 8%, 9%, 10%, 11%, 12%, 13%, 14%, or 15%, based on the total weight of all flavonolignan components. In some embodiments, the presence of sulfoalkyl ether cyclodextrin can selectively increase the weight percentage of silybin A in silymarin by about less than 1%, 2%, 3%, 4%, 5%, 6%, 7%, 8%, 9%, 10%, 11%, 12%, 13%, 14%, 15%, 20%, 25%, 30% or 50% by weight based on the total weight of all flavonolignan components. In some embodiments, the presence of sulfoalkyl ether cyclodextrin can selectively increase the weight percentage of silybin A in silymarin by about 0.1% to 20%, 1% to 20%, 1% to 10%, 1% to 5%, 2% to 20%, 2% to 10%, 2% to 5%, 3% to 20%, 3% to 10%, 3% to 5%, 4% to 20%, 4% to 10%, or 4% to 5%, by weight based on the total weight of all flavonolignan components. In some embodiments, the presence of sulfoalkyl ether cyclodextrin can selectively increase the weight percentage of silybin A in silymarin by about 2% to 9%, 2% to 8%, 2% to 7%, 2% to 6%, 3% to 9%, 3% to 8%, 3% to 7%, 3% to 6%, 3% to 5%, 4% to 9%, 4% to 8%, 4% to 7%, 4% to 6%, 5% to 9%, 5% to 8%, 5% to 7%, 5% to 6%, 6% to 9%, 6% to 8%, or 6% to 7%, by weight based on the total weight of all flavonolignan components.

In some embodiments, the presence of sulfoalkyl ether cyclodextrin can selectively increase the molar percentage of silybin A in silymarin by about more than 1%, 2%, 3%, 4%, 5%, 6%, 7%, 8%, 9%, 10%, 11%, 12%, 13%, 14%, or 15%, based on the moles of all flavonolignan components. In some embodiments, the presence of sulfoalkyl ether cyclodextrin can selectively increase the molar percentage of silybin A in silymarin by about less than 1%, 2%, 3%, 4%, 5%, 6%, 7%, 8%, 9%, 10%, 11%, 12%, 13%, 14%, 15%, 20%, 25%, 30% or 50% based on the total moles of all flavonolignan components. In some embodiments, the presence of sulfoalkyl ether cyclodextrin can selectively increase the molar percentage of silybin A in silymarin by about 0.1% to 20%, 1% to 20%, 1% to 10%, 1% to 5%, 2% to 20%, 2% to 10%, 2% to 5%, 3% to 20%, 3% to 10%, 3% to 5%, 4% to 20%, 4% to 10%, or 4% to 5%, based on the total moles of all flavonolignan components. In some embodiments, the presence of sulfoalkyl ether cyclodextrin can selectively increase the molar percentage of silybin A in silymarin by about 2% to 9%, 2% to 8%, 2% to 7%, 2% to 6%, 3% to 9%, 3% to 8%, 3% to 7%, 3% to 6%, 3% to 5%, 4% to 9%, 4% to 8%, 4% to 7%, 4% to 6%, 5% to 9%, 5% to 8%, 5% to 7%, 5% to 6%, 6% to 9%, 6% to 8%, or 6% to 7%, by weight based on the total moles of all flavonolignan components.

In some embodiments, the weight percentage of silybin A can be greater than about 1%, 2%, 3%, 4%, 5%, 6%, 7%, 8%, 9%, 10%, 11%, 12%, 13%, 14%, or 15%, based on the total weight of all flavonolignan components. In some embodiments, the weight percentage of silybin A in silymarin can be less than about 5%, 6%, 7%, 8%, 9%, 10%, 11%, 12%, 13%, 14%, 15%, 20%, 25%, 30% or 50% by weight based on the total weight of all flavonolignan components. In some embodiments, the weight percentage of silybin A can be in the range of about 0.1% to 20%, 1% to 15%, 1% to 10%, 2% to 15%, 2% to 12%, 3% to 15%, 3% to 12%, 4% to 15%, 4% to 12%, 6% to 15%, 8% to 12%, or 9% to 11%, by weight based on the total weight of all flavonolignan components.

In some embodiments, the molar percentage of silybin A can be greater than about 1%, 2%, 3%, 4%, 5%, 6%, 7%, 8%, 9%, 10%, 11%, 12%, 13%, 14%, or 15%, based on the total moles of all flavonolignan components. In some embodiments, the molar percentage of silybin A in silymarin can be less than about 5%, 6%, 7%, 8%, 9%, 10%, 11%, 12%, 13%, 14%, 15%, 20%, 25%, 30% or 50% by weight based on the total moles of all flavonolignan components. In some embodiments, the molar percentage of silybin A can be in the range of about 0.1% to 20%, 1% to 15%, 1% to 10%, 2% to 15%, 2% to 12%, 4% to 15%, 4% to 12%, 6% to 15%, 8% to 12%, or 9% to 11%, by weight based on the total moles of all flavonolignan components.

In some embodiments, the presence of sulfoalkyl ether cyclodextrin can selectively increase the weight percentage of silybin B in silymarin by about more than 5%, 6%, 7%, 8%, 9%, 10%, 11%, 12%, 13%, 14%, 15%, 16%, 17%, 18%, 19%, 20%, 25%, or 30% by weight based on the total weight of all flavonolignan components. In some embodiments, the presence of sulfoalkyl ether cyclodextrin can selectively increase the weight percentage of silybin B in silymarin by about less than 5%, 6%, 7%, 8%, 9%, 10%, 11%, 12%, 13%, 14%, 15%, 16%, 17%, 18%, 19%, 20%, 25%, 30% or 50% by weight based on the total weight of all flavonolignan components. In some embodiments, the presence of sulfoalkyl ether cyclodextrin can selectively increase the weight percentage of silybin B in silymarin by about 0.1% to 20%, 1% to 20%, 1% to 10%, 1% to 5%, 2% to 20%, 2% to 10%, 2% to 5%, 3% to 20%, 3% to 10%, 3% to 5%, 4% to 20%, 4% to 10%, or 4% to 5%, by weight based on the total weight of all flavonolignan components. In some embodiments, the presence of sulfoalkyl ether cyclodextrin can selectively increase the weight percentage of silybin A in silymarin by about 10% to 20%, 10% to 18%, 10% to 16%, 10% to 15%, 10% to 12%, 11% to 20%, 11% to 18%, 11% to 16%, 11% to 15%, 11% to 12%, 12% to 20%, 12% to 18%, 12% to 16%, 12% to 15%, 12% to 14%, 12% to 13%, 13% to 20%, 13% to 18%, 13% to 17%, 13% to 16%, 13% to 15%, or 13% to 14%, by weight based on the total weight of all flavonolignan components.

In some embodiments, the presence of sulfoalkyl ether cyclodextrin can selectively increase the molar percentage of silybin B in silymarin by about more than 5%, 6%, 7%, 8%, 9%, 10%, 11%, 12%, 13%, 14%, 15%, 16%, 17%, 18%, 19%, 20%, 25%, or 30% based on the total moles of all flavonolignan components. In some embodiments, the presence of sulfoalkyl ether cyclodextrin can selectively increase the molar percentage of silybin B in silymarin by about less than 5%, 6%, 7%, 8%, 9%, 10%, 11%, 12%, 13%, 14%, 15%, 16%, 17%, 18%, 19%, 20%, 25%, 30% or 50% based on the total moles of all flavonolignan components. In some embodiments, the presence of sulfoalkyl ether cyclodextrin can selectively increase the molar percentage of silybin B in silymarin by about 0.1% to 20%, 1% to 20%, 1% to 10%, 1% to 5%, 2% to 20%, 2% to 10%, 2% to 5%, 3% to 20%, 3% to 10%, 3% to 5%, 4% to 20%, 4% to 10%, or 4% to 5%, based on the total moles of all flavonolignan components. In some embodiments, the presence of sulfoalkyl ether cyclodextrin can selectively increase the molar percentage of silybin B in silymarin by about 10% to 20%, 10% to 18%, 10% to 16%, 10% to 15%, 10% to 12%, 11% to 20%, 11% to 18%, 11% to 16%, 11% to 15%, 11% to 12%, 12% to 20%, 12% to 18%, 12% to 16%, 12% to 15%, 12% to 14%, 12% to 13%, 13% to 20%, 13% to 18%, 13% to 17%, 13% to 16%, 13% to 15%, or 13% to 14%, based on the total moles of all flavonolignan components.

In some embodiments, the weight percentage of silybin B can be greater than about 1%, 2%, 3%, 4%, 5%, 6%, 7%, 8%, 9%, 10%, 11%, 12%, 13%, 14%, or 15%, based on the total weight of all flavonolignan components. In some embodiments, the weight percentage of silybin B in silymarin can be less than about 5%, 6%, 7%, 8%, 9%, 10%, 11%, 12%, 13%, 14%, 15%, 20%, 21%, 22%, 23%, 24%, 25%, 26%, 27%, 28%, 29%, 30%, 40% or 50% based on the total weight of all flavonolignan components. In some embodiments, the weight percentage of silybin B can be in the range of about 1% to 30%, 1% to 27%, 1% to 25%, 1% to 20%, 1% to about 15%, 5% to 30%, 5% to 27%, 5% to 25%, 5% to 20%, 10% to 30%, 10% to 27%, 10% to 25%, 10% to 20%, 15% to 30%, 15% to 27%, 15% to 25%, 15% to 20%, 20% to 30%, 20% to 27%, 20% to 25%, or 20.90% to 24.01% based on the total weight of all flavonolignan components.

In some embodiments, the molar percentage of silybin B can be greater than about 1%, 2%, 3%, 4%, 5%, 6%, 7%, 8%, 9%, 10%, 11%, 12%, 13%, 14%, or 15%, based on the total moles of all flavonolignan components. In some embodiments, the molar percentage of silybin B in silymarin can be less than about 5%, 6%, 7%, 8%, 9%, 10%, 11%, 12%, 13%, 14%, 15%, 20%, 21%, 22%, 23%, 24%, 25%, 26%, 27%, 28%, 29%, 30%, 40% or 50% based on the total moles of all flavonolignan components. In some embodiments, the molar percentage of silybin B can be in the range of about 1% to 30%, 1% to 27%, 1% to 25%, 1% to 20%, 1% to about 15%, 5% to 30%, 5% to 27%, 5% to 25%, 5% to 20%, 10% to 30%, 10% to 27%, 10% to 25%, 10% to 20%, 15% to 30%, 15% to 27%, 15% to 25%, 15% to 20%, 20% to 30%, 20% to 27%, 20% to 25%, or 20.90% to 24.01% based on the total moles of all flavonolignan components.

In some embodiments, the presence of sulfoalkyl ether cyclodextrin can selectively increase the weight percentage of isosilybin A in silymarin by about more than 5%, 6%, 7%, 8%, 9%, 10%, 11%, 12%, 13%, 14%, 15%, 16%, 17%, 18%, 19%, 20%, 25%, or 30% based on the total weight of all flavonolignan components. In some embodiments, the presence of sulfoalkyl ether cyclodextrin can selectively increase the weight percentage of isosilybin A in silymarin by about less than 5%, 6%, 7%, 8%, 9%, 10%, 11%, 12%, 13%, 14%, 15%, 16%, 17%, 18%, 19%, 20%, 25%, 30% or 50% based on the total weight of all flavonolignan components. In some embodiments, the presence of sulfoalkyl ether cyclodextrin can selectively increase the weight percentage of isosilybin A in silymarin by about 0.1% to 20%, 1% to 20%, 1% to 15%, 1% to 10%, 2% to 20%, 2% to 15%, 3% to 20%, 3% to 15%, 4% to 20%, 4% to 15%, or 10% to 15%, based on the total weight of all flavonolignan components. In some embodiments, the presence of sulfoalkyl ether cyclodextrin can selectively increase the weight percentage of isosilybin A in silymarin by about 5% to about 10%, 6% to about 10%, 7% to about 10%, or 7% to about 9%, based on the total weight of all flavonolignan components.

In some embodiments, the presence of sulfoalkyl ether cyclodextrin can selectively increase the molar percentage of isosilybin A in silymarin by about more than 5%, 6%, 7%, 8%, 9%, 10%, 11%, 12%, 13%, 14%, 15%, 16%, 17%, 18%, 19%, 20%, 25%, or 30% based on the total moles of all flavonolignan components. In some embodiments, the presence of sulfoalkyl ether cyclodextrin can selectively increase the molar percentage of isosilybin A in silymarin by about less than 5%, 6%, 7%, 8%, 9%, 10%, 11%, 12%, 13%, 14%, 15%, 16%, 17%, 18%, 19%, 20%, 25%, 30% or 50% based on the total moles of all flavonolignan components. In some embodiments, the presence of sulfoalkyl ether cyclodextrin can selectively increase the molar percentage of isosilybin A in silymarin by about 0.1% to 20%, 1% to 20%, 1% to 15%, 1% to 10%, 2% to 20%, 2% to 15%, 3% to 20%, 3% to 15%, 4% to 20%, 4% to 15%, or 10% to 15%, based on the total moles of all flavonolignan components. In some embodiments, the presence of sulfoalkyl ether cyclodextrin can selectively increase the molar percentage of isosilybin A in silymarin by about 5% to about 10%, 6% to about 10%, 7% to about 10%, or 7% to about 9%, based on the total moles of all flavonolignan components.

In some embodiments, the weight percentage of isosilybin A can be greater than about 1%, 2%, 3%, 4%, 5%, 6%, 7%, 8%, 9%, 10%, 11%, 12%, 13%, 14%, or 15%, based on the total weight of all flavonolignan components. In some embodiments, the weight percentage of isosilybin A in silymarin can be less than about 5%, 6%, 7%, 8%, 9%, 10%, 11%, 12%, 13%, 14%, 15%, 20%, 21%, 22%, 23%, 24%, 25%, 26%, 27%, 28%, 29%, 30%, 40% or 50% based on the total weight of all flavonolignan components. In some embodiments, the weight percentage of isosilybin A in silymarin can be in the range of about 5% to 20%, 5% to 18%, 5% to 16%, 5% to 15%, 10% to 20%, 10% to 18%, 10% to 16%, 10% to 15%, 11% to 20%, 11% to 18%, 11% to 16%, 11% to 15%, 11% to 14%, 12% to 20%, 12% to 18%, 12% to 16%, 12% to 15%, 12% to 14%, 13% to 20%, 13% to 18%, 13% to 17%, 13% to 16%, 13% to 15%, or 13% to 14%, based on the total weight of all flavonolignan components.

In some embodiments, the molar percentage of isosilybin A can be greater than about 1%, 2%, 3%, 4%, 5%, 6%, 7%, 8%, 9%, 10%, 11%, 12%, 13%, 14%, or 15%, based on the total moles of all flavonolignan components. In some embodiments, the molar percentage of isosilybin A in silymarin can be less than about 5%, 6%, 7%, 8%, 9%, 10%, 11%, 12%, 13%, 14%, 15%, 20%, 21%, 22%, 23%, 24%, 25%, 26%, 27%, 28%, 29%, 30%, 40% or 50% based on the total moles of all flavonolignan components. In some embodiments, the molar percentage of isosilybin A in silymarin can be in the range of about 5% to 20%, 5% to 18%, 5% to 16%, 5% to 15%, 10% to 20%, 10% to 18%, 10% to 16%, 10% to 15%, 11% to 20%, 11% to 18%, 11% to 16%, 11% to 15%, 11% to 14%, 12% to 20%, 12% to 18%, 12% to 16%, 12% to 15%, 12% to 14%, 13% to 20%, 13% to 18%, 13% to 17%, 13% to 16%, 13% to 15%, or 13% to 14%, based on the total moles of all flavonolignan components.

In some embodiments, the presence of sulfoalkyl ether cyclodextrin can selectively increase the weight percentage of isosilybin B in silymarin by about more than 0.1%, 0.5%, 1%, 1.5%, 2%, 2.5%, 3%, 3.5%, 4%, 5%, 6%, 7%, 8%, 9%, 10%, 11%, 12%, 13%, 14%, 15%, 16%, 17%, 18%, 19%, 20%, 25%, or 30% based on the total weight of all flavonolignan components. In some embodiments, the presence of sulfoalkyl ether cyclodextrin can selectively increase the weight percentage of isosilybin B in silymarin by about less than 0.1%, 0.5%, 1%, 1.5%, 2%, 2.5%, 3%, 3.5%, 4%, 5%, 6%, 7%, 8%, 9%, 10%, 11%, 12%, 13%, 14%, 15%, 16%, 17%, 18%, 19%, 20%, 25%, 30% or 50% based on the total weight of all flavonolignan components. In some embodiments, the presence of sulfoalkyl ether cyclodextrin can selectively increase the weight percentage of isosilybin B in silymarin by about 0.1% to 10%, 1% to 8%, 1% to 5%, 1% to 3%, 1.5% to 10%, 1.5% to 5%, 3% to 10%, 2% to 5%, 2% to 4%, 2% to 3.5%, or 2% to 3%, based on the total weight of all flavonolignan components.

In some embodiments, the presence of sulfoalkyl ether cyclodextrin can selectively increase the molar percentage of isosilybin B in silymarin by about more than 0.1%, 0.5%, 1%, 1.5%, 2%, 2.5%, 3%, 3.5%, 4%, 5%, 6%, 7%, 8%, 9%, 10%, 11%, 12%, 13%, 14%, 15%, 16%, 17%, 18%, 19%, 20%, 25%, or 30% based on the total moles of all flavonolignan components. In some embodiments, the presence of sulfoalkyl ether cyclodextrin can selectively increase the molar percentage of isosilybin B in silymarin by about less than 0.1%, 0.5%, 1%, 1.5%, 2%, 2.5%, 3%, 3.5%, 4%, 5%, 6%, 7%, 8%, 9%, 10%, 11%, 12%, 13%, 14%, 15%, 16%, 17%, 18%, 19%, 20%, 25%, 30% or 50% based on the total moles of all flavonolignan components. In some embodiments, the presence of sulfoalkyl ether cyclodextrin can selectively increase the molar percentage of isosilybin B in silymarin by about 0.1% to 10%, 1% to 8%, 1% to 5%, 1% to 3%, 1.5% to 10%, 1.5% to 5%, 3% to 10%, 2% to 5%, 2% to 4%, 2% to 3.5%, or 2% to 3%, based on the total moles of all flavonolignan components.

In some embodiments, the weight percentage of isosilybin B can be greater than about 1%, 2%, 3%, 4%, 5%, 6%, 7%, 8%, 9%, 10%, 11%, 12%, 13%, 14%, or 15%, based on the total weight of all flavonolignan components. In some embodiments, the weight percentage of isosilybin B in silymarin can be less than about 0.5%, 1%, 1.5%, 2%, 2.5%, 3%, 3.5%, 4%, 5%, 6%, 7%, 8%, 9%, 10%, 11%, 12%, 13%, 14%, 15%, 20%, 21%, 22%, 23%, 24%, 25%, 26%, 27%, 28%, 29%, 30%, 40% or 50% based on the total weight of all flavonolignan components. In some embodiments, the weight percentage of isosilybin B in silymarin can be in the range of about 1% to 10%, 1% to 5%, 2% to 8%, 2% to 6%, 3% to 6%, or 3% to 5%, based on the total weight of all flavonolignan components.

In some embodiments, the molar percentage of isosilybin B can be greater than about 1%, 2%, 3%, 4%, 5%, 6%, 7%, 8%, 9%, 10%, 11%, 12%, 13%, 14%, or 15%, based on the total moles of all flavonolignan components. In some embodiments, the molar percentage of isosilybin B in silymarin can be less than about 0.5%, 1%, 1.5%, 2%, 2.5%, 3%, 3.5%, 4%, 5%, 6%, 7%, 8%, 9%, 10%, 11%, 12%, 13%, 14%, 15%, 20%, 21%, 22%, 23%, 24%, 25%, 26%, 27%, 28%, 29%, 30%, 40% or 50% based on the total moles of all flavonolignan components. In some embodiments, the molar percentage of isosilybin B in silymarin can be in the range of about 1% to 10%, 1% to 5%, 2% to 8%, 2% to 6%, 3% to 6%, or 3% to 5%, based on the total moles of all flavonolignan components.

The presence of sulfoalkyl ether cyclodextrin in the composition, the preparation temperature, the type of silymarin extract used, and the process used to prepare the silymarin extract can also change the ratio between two or more components of silymarin. In some embodiments, the molar ratio of a first component to a second component can be based on any of the relative molar amounts for the first component to any of the relative molar amounts for the second component as listed in Table A below. For example, the molar ratio of silybin A to silybin B can be 6:15, 9:12, 9:24, 10:20, or any other combination in table A. In some embodiments, the molar ratio of silybin A to silybin B to isosilybin A to isosilybin B is in the range of about (6-12):(15-25):(10-20):(2-6). In some embodiments, the molar ratio of silybin A to silybin B to isosilybin A to isosilybin B is about 10:22:14:4.

TABLE A

| silymarin components and relative molar amount for each component | |
|---|---|
| Silymarin component | Relative molar amount |
| Silybin A | 6, 7, 8, 9, 10, 11, 12, 15 |
| Silybin B | 15, 20, 21, 22, 23, 24, 25, 30 |
| Isosilybin A | 10, 11, 12, 13, 14, 15, 20 |
| Isosilybin B | 2, 3, 4, 5, 6 |
| Silychristin A | 20, 30, 35, 40, 45 |
| Silydianin | 1, 2, 3, 4, 5, 6 |
| Silychristin B | 1, 2, 3, 4, 5 |
| Taxifolin | 1, 2, 3, 4, 5, 6, 7, 8, 9, 10 |

The presence of sulfoalkyl ether cyclodextrin can help selectively decrease the weight percentage of silychristin A in silymarin by about more than 1%, 2%, 3%, 4%, 5%, 6%, 7%, 8%, 9%, 10%, 11%, 12%, 13%, 14%, or 15%, by weight based on the total weight of all flavonolignan components. In some embodiments, the presence of sulfoalkyl ether cyclodextrin can selectively decrease the weight percentage of silychristin A in silymarin by about less than 1%, 2%, 3%, 4%, 5%, 6%, 7%, 8%, 9%, 10%, 11%, 12%, 13%, 14%, 15%, 20%, 25%, 30% or 50% by weight based on the total weight of all flavonolignan components. In some embodiments, the presence of sulfoalkyl ether cyclodextrin can selectively decrease the weight percentage of silychristin A in silymarin by about 0.1% to 20%, 1% to 20%, 1% to 10%, 1% to 5%, 2% to 20%, 2% to 10%, 2% to 5%, 3% to 20%, 3% to 10%, 3% to 5%, 4% to 20%, 4% to 10%, or 4% to 5%, by weight based on the total weight of all flavonolignan components. In some embodiments, the presence of sulfoalkyl ether cyclodextrin can selectively decrease the weight percentage of silychristin A in silymarin by about 2% to 9%, 2% to 8%, 2% to 7%, 2% to 6%, 3% to 9%, 3% to 8%, 3% to 7%, 3% to 6%, 3% to 5%, 4% to 9%, 4% to 8%, 4% to 7%, 4% to 6%, 5% to 9%, 5% to 8%, 5% to 7%, 5% to 6%, 6% to 9%, 6% to 8%, or 6% to 7%, by weight based on the total weight of all flavonolignan components.

Some embodiments relate to a composition comprising sulfoalkyl ether cyclodextrin and one or more of taxifolin, silychristin, silydianin, silybin A, silybin B, isosilybin A, and isosilybin B. In some embodiments, the molar ratio of taxifolin to sulfoalkyl ether cyclodextrin in the composition is in the range of about 0.01 to 0.5, about 0.02 to 0.4, about 0.02 to 0.25, or about 0.03 to 0.22. In some embodiments, the molar ratio of silychristin to sulfoalkyl ether cyclodextrin is in the range of about 0.02 to 0.5, about 0.02 to 0.4, about 0.06 to 0.3, about 0.06 to 0.25, or about 0.09 to 0.20. In some embodiments, the molar ratio of silydianin to sulfoalkyl ether cyclodextrin is in the range of about 0.04 to 0.5, about 0.05 to 0.5, about 0.05 to 0.30, about 0.08 to 0.25, or about 0.1 to 0.21. In some embodiments, the molar ratio of silybin A to sulfoalkyl ether cyclodextrin is in the range of about 0.01 to 0.1, about 0.01 to 0.07, about 0.02 to 0.07, about 0.02 to 0.06, or about 0.03 to 0.05. In some embodiments, the molar ratio of silybin B to sulfoalkyl ether cyclodextrin is in the range of about 0.01 to 0.5, about 0.01 to 0.25, about 0.02 to 0.25, about 0.02 to 0.2, about 0.04 to 0.15, about 0.05 to 0.12, or about 0.07 to 0.11. In some embodiments, the molar ratio of isosilybin A to sulfoalkyl ether cyclodextrin is in the range of about 0.01 to 0.15, about 0.01 to 0.1, about 0.02 to 0.09, about 0.03 to 0.09, or about 0.05 to 0.08. In some embodiments, the molar ratio of isosilybin B to sulfoalkyl ether cyclodextrin is in the range of about 0.001 to 0.05, about 0.002 to 0.04, about 0.002 to 0.03, about 0.005 to 0.03, about 0.01 to 0.03, or about 0.01 to 0.025.

Some embodiments relate to a composition comprising sulfoalkyl ether cyclodextrin and one or more of taxifolin, silychristin, silydianin, silybin A, silybin B, isosilybin A, and isosilybin B, wherein the molar ratio of taxifolin to sulfoalkyl ether cyclodextrin is in the range of about 0.02 to 0.25, wherein the molar ratio of silychristin to sulfoalkyl ether cyclodextrin is in the range of about 0.06 to 0.25, wherein the molar ratio of silydianin to sulfoalkyl ether cyclodextrin is in the range of about 0.08 to 0.25, wherein the molar ratio of silybin A to sulfoalkyl ether cyclodextrin is in the range of about 0.01 to 0.07, wherein the molar ratio of silybin B to sulfoalkyl ether cyclodextrin is in the range of about 0.04 to 0.15, wherein the molar ratio of isosilybin A to sulfoalkyl ether cyclodextrin is in the range of about 0.02 to 0.09, and wherein the molar ratio of isosilybin B to sulfoalkyl ether cyclodextrin is in the range of about 0.002 to 0.03.

In some embodiments, the molar ratio of a first component to a second component or a first component to a second component to SAE-CD in the composition described herein can be based on any of the molar ratio of the first component, the second component, and SAE-CD as listed in Table B below. For example, the molar ratio of taxifolin to sulfoalkyl ether cyclodextrin can be in the range of 0.3:10 to 2:10 or or any other combination in table B; the molar ratio of taxifolin to silychristin to SAE-CD can be in the range of (0.3-2):(1-2):10 or any other combination in table B; and the molar ratio of taxifolin to silychristin to silydianin to sulfoalkyl ether cyclodextrin is in the range of (0.3-2):(1-2):(1.4-2.5):10 or any other combination in table B.

TABLE B silymarin components and relative molar ratio between the components

| Component | Molar ratio 1 | Molar ratio 2 | Molar ratio 3 | Molar ratio 4 |
|---|---|---|---|---|
| Sulfoalkyl ether cyclodextrin (SAE-CD) | 10 | 10 | 10 | 10 |
| taxifolin | 0.3-2 | 0.5-1 | 0.15-5 | 0.1-10 |
| silychristin | 1-2.5 | 1-2 | 0.5-4 | 0.1-10 |
| Silydianin | 1.4-2.5 | 1.6-2.5 | 1.0-5 | 0.5-10 |
| silybin A | 0.1-0.6 | 0.4-0.6 | 0.1-1.0 | 0.05-5 |
| silybin B | 0.5-1.5 | 0.9-1.5 | 0.25-3.0 | 0.1-10 |
| isosilybin A | 0.4-0.9 | 0.5-0.9 | 0.2-2 | 0.1-5 |
| isosilybin B | 0.1-0.2 | 0.1-0.3 | 0.05-1 | 0.01-5 |

Silymarin Bioavailability

Some embodiments relate to a method of administration, comprising orally or parenterally (e.g. intraveneously) administering the composition described herein to a subject in need thereof to achieve an in vivo taxifolin plasma concentration $C_{max}$ from about 0.01 ng/ml to about 5000 ng/mL, from about 0.1 ng/ml to about 4000 ng/ml, from about 1 ng/ml to about 4000 ng/ml, from about 5 mg/nl to about 4000 ng/ml, from about 10 ng/ml to about 4000 ng/ml, from about 10 ng/ml to about 3000 ng/ml, from about 10 ng/ml to about 2500 ng/ml, from 10 ng/ml to about 2000 ng/ml, from about 10 ng/ml to about 1500 ng/ml, from about 10 ng/ml to about 1000 ng/ml, from about 200 ng/ml to about 3000 ng/ml, from about 500 ng/ml to about 2500 ng/ml, from 750 ng/ml to about 2000 ng/ml, from about 1000 ng/ml to about 4000 ng/ml, from about 1000 ng/ml to about 3000 ng/ml, from about 1000 ng/ml to about 2000 ng/ml, from about 5000 ng/ml to about 10000 nm/ml, or from 6000 ng/ml to about 9000 ng/ml. In some embodiments, the in vivo taxifolin plasma concentration $C_{max}$ is greater than about 0.1, 0.5, 1.0, 2.0, 3.0, 4.0, 5.0, 6.0, 7.0, 8.0, 9.0, 10, 15, 20, 30, 40, 50, 60, 70, 80, 90, 100, 120, 140, 160, 180, 200, 220, 240, 260, 280, 300, 320, 340, 350, 370, 400, 420, 450, 470, 500, 520, 550, 570, 600, 620, 650, 670, 700, 720, 750, 770, 800, 820, 850, 870, 900, 920, 950, 970, 1000, 1200, 1500, 1700, 2000, 2200, 2400, 2500, 2700, 3000, 3200, 3400, 3500, 3700, 4000, 4200, 4500, 4700, 4900, 6000, 7000, 7500, 8000, 9000, 10000, 12000, 14000, or 16000 ng/ml. In some embodiments, the in vivo taxifolin plasma concentration $C_{max}$ is lower than about 20000, 18000, 16000, 15000, 12000, 10000, 9000, 8000, 7000, 6000, 5000, 4900, 4700, 4500, 4200, 4000, 3700, 3500, 3400, 3200, 3000, 2800, 2500, 2400, 2200, 2000, 1700, 1500, 1200, 1000, 970, 950, 920, 900, 870, 850, 820, 800, 770, 750, 720, 700, 670, 650, 620, 600, 570, 550, 520, 500, 470, 450, 420, 400, 370, 350, 340, 320, 300, 280, 260, 240, 220, 200, 180, 160, 140, 120, 100, 90, 80, 70, 60, 50, 40, 30, 20, 15, 10, 9, 8, 7, 6, 5, 4, 3, 2, 1, or 0.5 ng/ml.

In some embodiments, orally or parenterally (e.g. intraveneously) administering the composition described herein to a subject in need thereof can increase the in vivo taxifolin plasma concentration $C_{max}$ by at least 4000%, 3900%, 3800%, 3700%, 3600%, 3500%, 3400%, 3300%, 3200%, 3100%, 3000%, 2900%, 2800%, 2700%, 2600%, 2500%, 2400%, 2300%, 2200%, 2100%, 2000%, 1900%, 1800%, 1700%, 1600%, 1500%, 1400%, 1300%, 1200%, 1100%, 1000%, 900%, 800%, 700%, 600%, 500%, 400%, 300%, 250%, 200%, 175%, 150%, 125%, 120%, 110%, 100%, 95%, 90%, 85%, 80%, 75%, 70%, 60%, 50%, 40%, 30%, 20%, 10%, or 5% when compared with administering silymarin or taxifolin without sulfoalkyl ether cyclodextrin. In some embodiments, orally or parenterally (e.g. intraveneously) administering the composition described herein to a subject in need thereof can achieve an in vivo taxifolin plasma concentration $C_{max}$ that is about the same as the in vivo taxifolin $C_{max}$ of administering silymarin or taxifolin without sulfoalkyl ether cyclodextrin. In some embodiments, orally or parenterally (e.g. intraveneously) administering the composition described herein to a subject in need thereof can achieve an in vivo taxifolin plasma concentration $C_{max}$ that is at least about 95%, 90%, 85%, 80%, 75%, 70%, 60%, or 50% of the in vivo taxifolin $C_{max}$ of administering silymarin or taxifolin without sulfoalkyl ether cyclodextrin.

Some embodiments relate to a method of method of administration, comprising orally or parenterally (e.g. intraveneously) administering the composition described herein to a subject in need thereof to achieve an in vivo silybin A plasma concentration $C_{max}$ from about 0.1 ng/ml to about 1000 ng/ml, from about 10 ng/ml to about 500 ng/ml, from about 10 ng/ml to about 300 ng/ml, from about 10 ng/ml to about 250 ng/ml, from 10 ng/ml to about 200 ng/ml, from about 10 ng/ml to about 150 ng/ml, from about 10 ng/ml to about 100 ng/ml, from about 20 ng/ml to about 300 ng/ml, from about 50 ng/ml to about 250 ng/ml, or from 75 ng/ml to about 200 ng/ml. In some embodiments, the in vivo silybin A plasma concentration $C_{max}$ is greater than about 0.1, 0.5, 1.0, 2.0, 3.0, 4.0, 5.0, 6.0, 7.0, 8.0, 9.0, 10, 15, 20, 30, 40, 50, 60, 70, 80, 90, 100, 120, 140, 160, 180, 200, 220, 240, 260, 280, 300, 320, 340, 350, 370, 400, 420, 450, 470, 500, 520, 550, 570, 600, 620, 650, 670, 700, 720, 750, 770, 800, 820, 850, 870, 900, 920, 950, 970, 1000, 1200, 1500, 1700, 2000, 2200, 2400, 2500, 2700, 3000, 3200, 3400, 3500, 3700, 4000, 4200, 4500, 4700, 4900, 5000, 6000, 7000, 7500, 8000, 9000, 10000, 12000, 14000, or 16000 ng/ml. In some embodiments, the in vivo silybin A plasma concentration $C_{max}$ is lower than about 20000, 18000, 16000, 15000, 12000, 10000, 9000, 8000, 7000, 6000, 5000, 4900, 4700, 4500, 4200, 4000, 3700, 3500, 3400, 3200, 3000, 2800, 2500, 2400, 2200, 2000, 1700, 1500, 1200, 1000, 970, 950, 920, 900, 870, 850, 820, 800, 770, 750, 720, 700, 670, 650, 620, 600, 570, 550, 520, 500, 470, 450, 420, 400, 370, 350, 340, 320, 300, 280, 260, 240, 220, 200, 180, 160, 140, 120, 100, 90, 80, 70, 60, 50, 40, 30, 20, 15, 10, 9, 8, 7, 6, 5, 4, 3, 2, 1, or 0.5 ng/ml.

In some embodiments, orally or parenterally (e.g. intraveneously) administering the composition described herein to a subject in need thereof can increase the in vivo silybin A plasma concentration $C_{max}$ by at least 4000%, 3900%, 3800%, 3700%, 3600%, 3500%, 3400%, 3300%, 3200%, 3100%, 3000%, 2900%, 2800%, 2700%, 2600%, 2500%, 2400%, 2300%, 2200%, 2100%, 2000%, 1900%, 1800%, 1700%, 1600%, 1500%, 1400%, 1300%, 1200%, 1100%, 1000%, 900%, 800%, 700%, 600%, 500%, 400%, 300%, 250%, 200%, 175%, 150%, 125%, 120%, 110%, 100%, 95%, 90%, 85%, 80%, 75%, 70%, 60%, 50%, 40%, 30%, 20%, 10%, or 5% when compared with administering silymarin or silybin A without sulfoalkyl ether cyclodextrin. In some embodiments, orally or parenterally (e.g. intraveneously) administering the composition described herein to a subject in need thereof can achieve an in vivo silybin A plasma concentration $C_{max}$ that is about the same as the in vivo silybin A $C_{max}$ of administering silymarin or silybin A without sulfoalkyl ether cyclodextrin. In some embodiments, orally or parenterally (e.g. intraveneously) administering the composition described herein to a subject in need thereof can achieve an in vivo silybin A plasma concentration $C_{max}$ that is at least about 95%, 90%, 85%, 80%, 75%, 70%, 60%, or 50% of the in vivo silybin A $C_{max}$ of administering silymarin or silybin A without sulfoalkyl ether cyclodextrin.

Some embodiments relate to a method of administration, comprising orally or parenterally (e.g. intraveneously) administering the composition described herein to a subject in need thereof to achieve an in vivo silybin B plasma concentration $C_{max}$ from about 0.1 ng/ml to about 1000 ng/ml, from about 10 ng/ml to about 500 ng/ml, from about 10 ng/ml to about 300 ng/ml, from about 10 ng/ml to about 300 ng/ml, from about 10 ng/ml to about 250 ng/ml, from 10 ng/ml to about 200 ng/ml, from about 10 ng/ml to about 150 ng/ml, from about 10 ng/ml to about 100 ng/ml, from about 20 ng/ml to about 300 ng/ml, from about 50 ng/ml to about 250 ng/ml, or from 75 ng/ml to about 200 ng/ml. In some embodiments, the in vivo silybin B plasma concentration $C_{max}$ is greater than about 0.1, 0.5, 1.0, 2.0, 3.0, 4.0, 5.0, 6.0, 7.0, 8.0, 9.0, 10, 15, 20, 30, 40, 50, 60, 70, 80, 90, 100, 120, 140, 160, 180, 200, 220, 240, 260, 280, 300, 320, 340, 350, 370, 400, 420, 450, 470, 500, 520, 550, 570, 600, 620, 650, 670, 700, 720, 750, 770, 800, 820, 850, 870, 900, 920, 950, 970, 1000, 1200, 1500, 1700, 2000, 2200, 2400, 2500, 2700, 3000, 3200, 3400, 3500, 3700, 4000, 4200, 4500, 4700, 4900, 5000, 6000, 7000, 7500, 8000, 9000, 10000, 12000, 14000, or 16000 ng/ml. In some embodiments, the in vivo silybin B plasma concentration $C_{max}$ is lower than about 15000, 12000, 10000, 9000, 8000, 7000, 6000, 5000, 4900, 4700, 4500, 4200, 4000, 3700, 3500, 3400, 3200, 3000, 2800, 2500, 2400, 2200, 2000, 1700, 1500, 1200, 1000, 970, 950, 920, 900, 870, 850, 820, 800, 770, 750, 720, 700, 670, 650, 620, 600, 570, 550, 520, 500, 470, 450, 420, 400, 370, 350, 340, 320, 300, 280, 260, 240, 220, 200, 180, 160, 140, 120, 100, 90, 80, 70, 60, 50, 40, 30, 20, 15, 10, 9, 8, 7, 6, 5, 4, 3, 2, 1, or 0.5 ng/ml.

In some embodiments, orally or parenterally (e.g. intraveneously) administering the composition described herein to a subject in need thereof can increase the in vivo silybin B plasma concentration $C_{max}$ by at least 4000%, 3900%, 3800%, 3700%, 3600%, 3500%, 3400%, 3300%, 3200%, 3100%, 3000%, 2900%, 2800%, 2700%, 2600%, 2500%, 2400%, 2300%, 2200%, 2100%, 2000%, 1900%, 1800%, 1700%, 1600%, 1500%, 1400%, 1300%, 1200%, 1100%, 1000%, 900%, 800%, 700%, 600%, 500%, 400%, 300%, 250%, 200%, 175%, 150%, 125%, 120%, 110%, 100%, 95%, 90%, 85%, 80%, 75%, 70%, 60%, 50%, 40%, 30%, 20%, 10%, or 5% when compared with administering silymarin or silybin B without sulfoalkyl ether cyclodextrin. In some embodiments, orally or parenterally (e.g. intraveneously) administering the composition described herein to a subject in need thereof can achieve an in vivo silybin B plasma concentration $C_{max}$ that is about the same as the in vivo silybin B $C_{max}$ of administering silymarin or silybin B without sulfoalkyl ether cyclodextrin.

Some embodiments relate to a method of method of administration, comprising orally or parenterally (e.g. intraveneously) administering the composition described herein to a subject in need thereof to achieve an in vivo isosilybin A plasma concentration $C_{max}$ from about 0.1 ng/ml to about 1000 ng/ml, from about 10 ng/ml to about 500 ng/ml, from about 10 ng/ml to about 300 ng/ml, from about 10 ng/ml to about 250 ng/ml, from 10 ng/ml to about 200 ng/ml, from about 10 ng/ml to about 150 ng/ml, from about 10 ng/ml to about 100 ng/ml, from about 20 ng/ml to about 300 ng/ml, from about 50 ng/ml to about 250 ng/ml, or from 75 ng/ml to about 200 ng/ml. In some embodiments, the in vivo isosilybin A plasma concentration $C_{max}$ is greater than about 0.1, 0.5, 1.0, 2.0, 3.0, 4.0, 5.0, 6.0, 7.0, 8.0, 9.0, 10, 15, 20, 30, 40, 50, 60, 70, 80, 90, 100, 120, 140, 160, 180, 200, 220, 240, 260, 280, 300, 320, 340, 350, 370, 400, 420, 450, 470, 500, 520, 550, 570, 600, 620, 650, 670, 700, 720, 750, 770, 800, 820, 850, 870, 900, 920, 950, 970, 1000, 1200, 1500, 1700, 2000, 2200, 2400, 2500, 2700, 3000, 3200, 3400, 3500, 3700, 4000, 4200, 4500, 4700, 4900, 5000, 6000, 7000, 7500, 8000, 9000, 10000, 12000, 14000, or 16000 ng/ml. In some embodiments, the in vivo isosilybin A plasma concentration $C_{max}$ is lower than about 15000, 12000, 10000, 9000, 8000, 7000, 6000, 5000, 4900, 4700, 4500, 4200, 4000, 3700, 3500, 3400, 3200, 3000, 2800, 2500, 2400, 2200, 2000, 1700, 1500, 1200, 1000, 970, 950, 920, 900, 870, 850, 820, 800, 770, 750, 720, 700, 670, 650, 620, 600, 570, 550, 520, 500, 470, 450, 420, 400, 370, 350, 340, 320, 300, 280, 260, 240, 220, 200, 180, 160, 140, 120, 100, 90, 80, 70, 60, 50, 40, 30, 20, 15, 10, 9, 8, 7, 6, 5, 4, 3, 2, 1, or 0.5 ng/ml.

In some embodiments, orally or parenterally (e.g. intraveneously) administering the composition described herein to a subject in need thereof can increase the in vivo isosilybin A plasma concentration $C_{max}$ by at least 4000%, 3900%, 3800%, 3700%, 3600%, 3500%, 3400%, 3300%, 3200%, 3100%, 3000%, 2900%, 2800%, 2700%, 2600%, 2500%, 2400%, 2300%, 2200%, 2100%, 2000%, 1900%, 1800%, 1700%, 1600%, 1500%, 1400%, 1300%, 1200%, 1100%, 1000%, 900%, 800%, 700%, 600%, 500%, 400%, 300%, 250%, 200%, 175%, 150%, 125%, 120%, 110%, 100%, 95%, 90%, 85%, 80%, 75%, 70%, 60%, 50%, 40%, 30%, 20%, 10%, or 5% when compared with administering silymarin or isosilybin A without sulfoalkyl ether cyclodextrin.

Some embodiments relate to a method of administration, comprising orally or parenterally (e.g. intraveneously) administering the composition described herein to a subject in need thereof to achieve an in vivo isosilybin B plasma concentration $C_{max}$ from about 0.1 ng/ml to about 1000 ng/ml, from about 10 ng/ml to about 500 ng/ml, from about 10 ng/ml to about 300 ng/ml, from about 10 ng/ml to about 300 ng/ml, from about 10 ng/ml to about 250 ng/ml, from 10 ng/ml to about 200 ng/ml, from about 10 ng/ml to about 150 ng/ml, from about 10 ng/ml to about 100 ng/ml, from about 20 ng/ml to about 300 ng/ml, from about 50 ng/ml to about 250 ng/ml, or from 75 ng/ml to about 200 ng/ml. In some embodiments, the in vivo isosilybin B plasma concentration $C_{max}$ is greater than about 0.1, 0.5, 1.0, 2.0, 3.0, 4.0, 5.0, 6.0, 7.0, 8.0, 9.0, 10, 15, 20, 30, 40, 50, 60, 70, 80, 90, 100, 120, 140, 160, 180, 200, 220, 240, 260, 280, 300, 320, 340, 350, 370, 400, 420, 450, 470, 500, 520, 550, 570, 600, 620, 650, 670, 700, 720, 750, 770, 800, 820, 850, 870, 900, 920, 950, 970, 1000, 1200, 1500, 1700, 2000, 2200, 2400, 2500, 2700, 3000, 3200, 3400, 3500, 3700, 4000, 4200, 4500, 4700, or 4900 ng/ml. In some embodiments, the in vivo isosilybin B plasma concentration $C_{max}$ is lower than about 15000, 12000, 10000, 9000, 8000, 7000, 6000, 5000, 4900, 4700, 4500, 4200, 4000, 3700, 3500, 3400, 3200, 3000, 2800, 2500, 2400, 2200, 2000, 1700, 1500, 1200, 1000, 970, 950, 920, 900, 870, 850, 820, 800, 770, 750, 720, 700, 670, 650, 620, 600, 570, 550, 520, 500, 470, 450, 420, 400, 370, 350, 340, 320, 300, 280, 260, 240, 220, 200, 180, 160, 140, 120, 100, 90, 80, 70, 60, 50, 40, 30, 20, 15, 10, 9, 8, 7, 6, 5, 4, 3, 2, 1, or 0.5 ng/ml.

In some embodiments, orally or parenterally (e.g. intraveneously) administering the composition described herein to a subject in need thereof can increase the in vivo isosilybin B plasma concentration $C_{max}$ by at least 4000%, 3900%, 3800%, 3700%, 3600%, 3500%, 3400%, 3300%, 3200%, 3100%, 3000%, 2900%, 2800%, 2700%, 2600%, 2500%, 2400%, 2300%, 2200%, 2100%, 2000%, 1900%, 1800%, 1700%, 1600%, 1500%, 1400%, 1300%, 1200%, 1100%, 1000%, 900%, 800%, 700%, 600%, 500%, 400%, 300%, 250%, 200%, 175%, 150%, 125%, 120%, 110%, 100%, 95%, 90%, 85%, 80%, 75%, 70%, 60%, 50%, 40%, 30%, 20%, 10%, or 5% when compared with administering silymarin or isosilybin B without sulfoalkyl ether cyclodextrin.

Some embodiments relate to a method of administration, comprising orally or parenterally (e.g. intraveneously) administering the composition described herein to a subject in need thereof to achieve an in vivo taxifolin $AUC_{(0\text{-}inf)}$ or $AUC_{(0\text{-}2h)}$ from about 1 ng*h/ml to about 20000 ng*h/ml, from about 100 ng*h/ml to about 15000 ng*h/ml, from about 100 ng*h/ml to about 10000 ng*h/ml, from about 500 ng*h/ml to about 10000 ng*h/ml, from about 1000 ng*h/ml to about 10000 ng*h/ml, from about 1000 ng*h/ml to about 8000 ng*h/ml, from about 1000 ng*h/ml to about 7000 ng*h/ml, from about 1000 ng*h/ml to about 6000 ng*h/ml, from about 1000 ng*h/ml to about 5000 ng*h/ml, from about 1000 ng*h/ml to about 2500 ng*h/ml, from about 500 ng*h/ml to about 2500 ng*h/ml, from 750 ng*h/ml to about 2000 ng*h/ml, from about 200 ng*h/ml to about 3000 ng*h/ml, from 100 ng*h/ml to about 2000 ng*h/ml, from about 100 ng*h/ml to about 1500 ng*h/ml, or from about 10 ng*h/ml to about 500 ng*h/ml. In some embodiments, the in vivo taxifolin $AUC_{(0\text{-}inf)}$ or $AUC_{(0\text{-}2h)}$ is greater than about 1.0, 2.0, 3.0, 4.0, 5.0, 6.0, 7.0, 8.0, 9.0, 10, 15, 20, 30, 40, 50, 60, 70, 80, 90, 100, 120, 140, 160, 180, 200, 220, 240, 260, 280, 300, 320, 340, 350, 370, 400, 420, 450, 470, 500, 520, 550, 570, 600, 620, 650, 670, 700, 720, 750, 770, 800, 820, 850, 870, 900, 920, 950, 970, 1000, 1200, 1500, 1700, 2000, 2200, 2400, 2500, 2700, 3000, 3200, 3400, 3500, 3700, 4000, 4200, 4500, 4700, 4900, 5000, 5500, 6000, 6500, 7000, 7500, 8000, 8500, 9000, 10000, 11000, 12000, or 12500 ng*h/ml. In some embodiments, the in vivo taxifolin $AUC_{(0\text{-}inf)}$ or $AUC_{(0\text{-}2h)}$ is lower than about 12000, 11000, 10000, 9000, 8000, 7000, 6000, 5000, 4900, 4700, 4500, 4200, 4000, 3700, 3500, 3400, 3200, 3000, 2800, 2500, 2400, 2200, 2000, 1700, 1500, 1200, 1000, 970, 950, 920, 900, 870, 850, 820, 800, 770, 750, 720, 700, 670, 650, 620, 600, 570, 550, 520, 500, 470, 450, 420, 400, 370, 350, 340, 320, 300, 280, 260, 240, 220, 200, 180, 160, 140, 120, 100, 90, 80, 70, 60, 50, 40, 30, 20, 15, 10, 9, 8, 7, 6, 5, 4, 3, 2, 1, or 0.5 ng*h/ml.

In some embodiments, orally or parenterally (e.g. intraveneously) administering the composition described herein to a subject in need thereof can increase the in vivo taxifolin plasma $AUC_{(0\text{-}inf)}$ or $AUC_{(0\text{-}2h)}$ by at least 4000%, 3900%, 3800%, 3700%, 3600%, 3500%, 3400%, 3300%, 3200%, 3100%, 3000%, 2900%, 2800%, 2700%, 2600%, 2500%, 2400%, 2300%, 2200%, 2100%, 2000%, 1900%, 1800%, 1700%, 1600%, 1500%, 1400%, 1300%, 1200%, 1100%, 1000%, 900%, 800%, 700%, 600%, 500%, 400%, 300%, 250%, 200%, 175%, 150%, 125%, 120%, 110%, 100%, 95%, 90%, 85%, 80%, 75%, 70%, 60%, 50%, 40%, 30%, 20%, 10%, or 5% when compared with administering silymarin or taxifolin without sulfoalkyl ether cyclodextrin. In some embodiments, orally or parenterally (e.g. intraveneously) administering the composition described herein to a subject in need thereof can achieve an in vivo taxifolin $AUC_{(0\text{-}inf)}$ or $AUC_{(0\text{-}2h)}$ that is about the same as the in vivo taxifolin $AUC_{(0\text{-}inf)}$ or $AUC_{(0\text{-}2h)}$ of administering silymarin or taxifolin without sulfoalkyl ether cyclodextrin.

Some embodiments relate to a method of administration, comprising orally or parenterally (e.g. intraveneously) administering the composition described herein to a subject in need thereof to achieve an in vivo silybin A $AUC_{(0\text{-}inf)}$ or $AUC_{(0\text{-}2h)}$ from about 1 ng*h/ml to about 2000 ng*h/ml, from about 10 ng*h/ml to about 1500 ng*h/ml, from about 10 ng*h/ml to about 1000 ng*h/ml, from about 50 ng*h/ml to about 1000 ng*h/ml, from about 100 ng*h/ml to about 1000 ng*h/ml, from about 100 ng*h/ml to about 800 ng*h/ml, from about 100 ng*h/ml to about 700 ng*h/ml, from about 100 ng*h/ml to about 600 ng*h/ml, from about 100 ng*h/ml to about 500 ng*h/ml, from about 100 ng*h/ml to about 250 ng*h/ml, from about 20 ng*h/ml to about 200 ng*h/ml, from 50 ng*h/ml to about 200 ng*h/ml, from about 20 ng*h/ml to about 300 ng*h/ml, from 100 ng*h/ml to about 500 ng*h/ml, from about 100 ng*h/ml to about 300 ng*h/ml, or from about 100 ng*h/ml to about 250 ng*h/ml. In some embodiments, the in vivo silybin A $AUC_{(0-inf)}$ or $AUC_{(0-2h)}$ is greater than about 1.0, 2.0, 3.0, 4.0, 5.0, 6.0, 7.0, 8.0, 9.0, 10, 15, 20, 30, 40, 50, 60, 70, 80, 90, 100, 120, 140, 160, 180, 200, 220, 240, 260, 280, 300, 320, 340, 350, 370, 400, 420, 450, 470, 500, 520, 550, 570, 600, 620, 650, 670, 700, 720, 750, 770, 800, 820, 850, 870, 900, 920, 950, 970, 1000, 1200, 1500, 1700, 2000, 2200, 2400, 2500, 2700, 3000, 3200, 3400, 3500, 3700, or 4000 ng*h/ml. In some embodiments, the in vivo silybin A $AUC_{(0-inf)}$ or $AUC_{(0-2h)}$ is lower than about 4000, 3700, 3500, 3400, 3200, 3000, 2800, 2500, 2400, 2200, 2000, 1700, 1500, 1200, 1000, 970, 950, 920, 900, 870, 850, 820, 800, 770, 750, 720, 700, 670, 650, 620, 600, 570, 550, 520, 500, 470, 450, 420, 400, 370, 350, 340, 320, 300, 280, 260, 240, 220, 200, 180, 160, 140, 120, 100, 90, 80, 70, 60, 50, 40, 30, 20, 15, 10, 9, 8, 7, 6, 5, 4, 3, 2, 1, or 0.5 ng*h/ml.

In some embodiments, orally or parenterally (e.g. intraveneously) administering the composition described herein to a subject in need thereof can increase the in vivo silybin A plasma $AUC_{(0-inf)}$ or $AUC_{(0-2h)}$ by at least 4000%, 3900%, 3800%, 3700%, 3600%, 3500%, 3400%, 3300%, 3200%, 3100%, 3000%, 2900%, 2800%, 2700%, 2600%, 2500%, 2400%, 2300%, 2200%, 2100%, 2000%, 1900%, 1800%, 1700%, 1600%, 1500%, 1400%, 1300%, 1200%, 1100%, 1000%, 900%, 800%, 700%, 600%, 500%, 400%, 300%, 250%, 200%, 175%, 150%, 125%, 120%, 110%, 100%, 95%, 90%, 85%, 80%, 75%, 70%, 60%, 50%, 40%, 30%, 20%, 10%, or 5% when compared with administering silymarin or silybin A without sulfoalkyl ether cyclodextrin.

Some embodiments relate to a method of administration, comprising orally or parenterally (e.g. intraveneously) administering the composition described herein to a subject in need thereof to achieve an in vivo silybin B $AUC_{(0-inf)}$ or $AUC_{(0-2h)}$ from about 1 ng*h/ml to about 3000 ng*h/ml, from about 10 ng*h/ml to about 2500 ng*h/ml, from about 10 ng*h/ml to about 2000 ng*h/ml, from about 10 ng*h/ml to about 1500 ng*h/ml, from about 10 ng*h/ml to about 1000 ng*h/ml, from about 50 ng*h/ml to about 2000 ng*h/ml, from about 100 ng*h/ml to about 2000 ng*h/ml, from about 100 ng*h/ml to about 1000 ng*h/ml, from about 100 ng*h/ml to about 700 ng*h/ml, from about 100 ng*h/ml to about 600 ng*h/ml, from about 100 ng*h/ml to about 500 ng*h/ml, from about 100 ng*h/ml to about 250 ng*h/ml, from about 20 ng*h/ml to about 200 ng*h/ml, from 50 ng*h/ml to about 200 ng*h/ml, from about 20 ng*h/ml to about 300 ng*h/ml, from 100 ng*h/ml to about 500 ng*h/ml, from about 100 ng*h/ml to about 300 ng*h/ml, or from about 100 ng*h/ml to about 250 ng*h/ml. In some embodiments, the in vivo silybin B $AUC_{(0-inf)}$ or $AUC_{(0-2h)}$ is greater than about 10, 15, 20, 30, 40, 50, 60, 70, 80, 90, 100, 120, 140, 160, 180, 200, 220, 240, 260, 280, 300, 320, 340, 350, 370, 400, 420, 450, 470, 500, 520, 550, 570, 600, 620, 650, 670, 700, 720, 750, 770, 800, 820, 850, 870, 900, 920, 950, 970, 1000, 1200, 1500, 1700, 2000, 2200, 2400, 2500, 2700, 3000, 3200, 3400, 3500, 3700, or 4000 ng*h/ml. In some embodiments, the in vivo silybin B $AUC_{(0-inf)}$ or $AUC_{(0-2h)}$ is lower than about 4000, 3700, 3500, 3400, 3200, 3000, 2800, 2500, 2400, 2200, 2000, 1700, 1500, 1200, 1000, 970, 950, 920, 900, 870, 850, 820, 800, 770, 750, 720, 700, 670, 650, 620, 600, 570, 550, 520, 500, 470, 450, 420, 400, 370, 350, 340, 320, 300, 280, 260, 240, 220, 200, 180, 160, 140, 120, 100, 90, 80, 70, 60, 50, 40, 30, 20, 15, 10, 9, 8, 7, 6, 5, 4, 3, 2, 1, or 0.5 ng*h/ml.

In some embodiments, orally or parenterally (e.g. intraveneously) administering the composition described herein to a subject in need thereof can increase the in vivo silybin B plasma $AUC_{(0-inf)}$ or $AUC_{(0-2h)}$ by at least 4000%, 3900%, 3800%, 3700%, 3600%, 3500%, 3400%, 3300%, 3200%, 3100%, 3000%, 2900%, 2800%, 2700%, 2600%, 2500%, 2400%, 2300%, 2200%, 2100%, 2000%, 1900%, 1800%, 1700%, 1600%, 1500%, 1400%, 1300%, 1200%, 1100%, 1000%, 900%, 800%, 700%, 600%, 500%, 400%, 300%, 250%, 200%, 175%, 150%, 125%, 120%, 110%, 100%, 95%, 90%, 85%, 80%, 75%, 70%, 60%, 50%, 40%, 30%, 20%, 10%, or 5% when compared with administering silymarin or silybin B without sulfoalkyl ether cyclodextrin.

Some embodiments relate to a method of administration, comprising orally or parenterally (e.g. intraveneously) administering the composition described herein to a subject in need thereof to achieve an in vivo isosilybin A $AUC_{(0-inf)}$ or $AUC_{(0-2h)}$ from about 1 ng*h/ml to about 2000 ng*h/ml, from about 10 ng*h/ml to about 1500 ng*h/ml, from about 10 ng*h/ml to about 1000 ng*h/ml, from about 50 ng*h/ml to about 1000 ng*h/ml, from about 100 ng*h/ml to about 1000 ng*h/ml, from about 100 ng*h/ml to about 800 ng*h/ml, from about 100 ng*h/ml to about 700 ng*h/ml, from about 100 ng*h/ml to about 600 ng*h/ml, from about 100 ng*h/ml to about 500 ng*h/ml, from about 100 ng*h/ml to about 250 ng*h/ml, from about 20 ng*h/ml to about 200 ng*h/ml, from 50 ng*h/ml to about 200 ng*h/ml, from about 20 ng*h/ml to about 300 ng*h/ml, from 100 ng*h/ml to about 500 ng*h/ml, from about 100 ng*h/ml to about 300 ng*h/ml, or from about 100 ng*h/ml to about 250 ng*h/ml. In some embodiments, the in vivo isosilybin A $AUC_{(0-inf)}$ or $AUC_{(0-2h)}$ is greater than about 1.0, 2.0, 3.0, 4.0, 5.0, 6.0, 7.0, 8.0, 9.0, 10, 15, 20, 30, 40, 50, 60, 70, 80, 90, 100, 120, 140, 160, 180, 200, 220, 240, 260, 280, 300, 320, 340, 350, 370, 400, 420, 450, 470, 500, 520, 550, 570, 600, 620, 650, 670, 700, 720, 750, 770, 800, 820, 850, 870, 900, 920, 950, 970, 1000, 1200, 1500, 1700, 2000, 2200, 2400, 2500, 2700, 3000, 3200, 3400, 3500, 3700, or 4000 ng*h/ml. In some embodiments, the in vivo isosilybin A $AUC_{(0-inf)}$ or $AUC_{(0-2h)}$ is lower than about 4000, 3700, 3500, 3400, 3200, 3000, 2800, 2500, 2400, 2200, 2000, 1700, 1500, 1200, 1000, 970, 950, 920, 900, 870, 850, 820, 800, 770, 750, 720, 700, 670, 650, 620, 600, 570, 550, 520, 500, 470, 450, 420, 400, 370, 350, 340, 320, 300, 280, 260, 240, 220, 200, 180, 160, 140, 120, 100, 90, 80, 70, 60, 50, 40, 30, 20, 15, 10, 9, 8, 7, 6, 5, 4, 3, 2, 1, or 0.5 ng*h/ml.

In some embodiments, orally or parenterally (e.g. intraveneously) administering the composition described herein to a subject in need thereof can increase the in vivo isosilybin A plasma $AUC_{(0-inf)}$ or $AUC_{(0-2h)}$ by at least 4000%, 3900%, 3800%, 3700%, 3600%, 3500%, 3400%, 3300%, 3200%, 3100%, 3000%, 2900%, 2800%, 2700%, 2600%, 2500%, 2400%, 2300%, 2200%, 2100%, 2000%, 1900%, 1800%, 1700%, 1600%, 1500%, 1400%, 1300%, 1200%, 1100%, 1000%, 900%, 800%, 700%, 600%, 500%, 400%, 300%, 250%, 200%, 175%, 150%, 125%, 120%, 110%, 100%, 95%, 90%, 85%, 80%, 75%, 70%, 60%, 50%, 40%, 30%, 20%, 10%, or 5% when compared with administering silymarin or isosilybin A without sulfoalkyl ether cyclodextrin.

Some embodiments relate to a method of administration, comprising orally or parenterally (e.g. intraveneously)

administering the composition described herein to a subject in need thereof to achieve an in vivo isosilybin B $AUC_{(0\text{-}inf)}$ or $AUC_{(0\text{-}2h)}$ from about 1 ng*h/ml to about 3000 ng*h/ml, from about 10 ng*h/ml to about 2500 ng*h/ml, from about 10 ng*h/ml to about 2000 ng*h/ml, from about 10 ng*h/ml to about 1500 ng*h/ml, from about 10 ng*h/ml to about 1000 ng*h/ml, from about 50 ng*h/ml to about 2000 ng*h/ml, from about 100 ng*h/ml to about 2000 ng*h/ml, from about 100 ng*h/ml to about 1000 ng*h/ml, from about 100 ng*h/ml to about 700 ng*h/ml, from about 100 ng*h/ml to about 600 ng*h/ml, from about 100 ng*h/ml to about 500 ng*h/ml, from about 100 ng*h/ml to about 250 ng*h/ml, from about 20 ng*h/ml to about 200 ng*h/ml, from 50 ng*h/ml to about 200 ng*h/ml, from about 20 ng*h/ml to about 300 ng*h/ml, from 100 ng*h/ml to about 500 ng*h/ml, from about 100 ng*h/ml to about 300 ng*h/ml, or from about 100 ng*h/ml to about 250 ng*h/ml. In some embodiments, the in vivo isosilybin B $AUC_{(0\text{-}inf)}$ or $AUC_{(0\text{-}2h)}$ is greater than about 10, 15, 20, 30, 40, 50, 60, 70, 80, 90, 100, 120, 140, 160, 180, 200, 220, 240, 260, 280, 300, 320, 340, 350, 370, 400, 420, 450, 470, 500, 520, 550, 570, 600, 620, 650, 670, 700, 720, 750, 770, 800, 820, 850, 870, 900, 920, 950, 970, 1000, 1200, 1500, 1700, 2000, 2200, 2400, 2500, 2700, 3000, 3200, 3400, 3500, 3700, or 4000 ng*h/ml. In some embodiments, the in vivo isosilybin B $AUC_{(0\text{-}inf)}$ or $AUC_{(0\text{-}2h)}$ is lower than about 4000, 3700, 3500, 3400, 3200, 3000, 2800, 2500, 2400, 2200, 2000, 1700, 1500, 1200, 1000, 970, 950, 920, 900, 870, 850, 820, 800, 770, 750, 720, 700, 670, 650, 620, 600, 570, 550, 520, 500, 470, 450, 420, 400, 370, 350, 340, 320, 300, 280, 260, 240, 220, 200, 180, 160, 140, 120, 100, 90, 80, 70, 60, 50, 40, 30, 20, 15, 10, 9, 8, 7, 6, 5, 4, 3, 2, 1, or 0.5 ng*h/ml.

In some embodiments, orally or parenterally (e.g. intraveneously) administering the composition described herein to a subject in need thereof can increase the in vivo isosilybin B plasma $AUC_{(0\text{-}inf)}$ or $AUC_{(0\text{-}2h)}$ by at least 4000%, 3900%, 3800%, 3700%, 3600%, 3500%, 3400%, 3300%, 3200%, 3100%, 3000%, 2900%, 2800%, 2700%, 2600%, 2500%, 2400%, 2300%, 2200%, 2100%, 2000%, 1900%, 1800%, 1700%, 1600%, 1500%, 1400%, 1300%, 1200%, 1100%, 1000%, 900%, 800%, 700%, 600%, 500%, 400%, 300%, 250%, 200%, 175%, 150%, 125%, 120%, 110%, 100%, 95%, 90%, 85%, 80%, 75%, 70%, 60%, 50%, 40%, 30%, 20%, 10%, or 5% when compared with administering silymarin or isosilybin B without sulfoalkyl ether cyclodextrin.

In some embodiments, orally or parenterally (e.g. intraveneously) administering the composition described herein to a subject in need thereof can increase the amount of taxifolin permeated across the lipid cell membrane of the GI tract by at least 100, 90, 80, 70, 60, 50, 40, 30, 20, 18, 16, 15, 13, 12, 10, 9, 8, 7, 6, 5, 4, 3, or 2 folds when compared with administering silymarin or taxifolin without sulfoalkyl ether cyclodextrin.

In some embodiments, orally or parenterally (e.g. intraveneously) administering the composition described herein to a subject in need thereof can increase the amount of silychristin permeated across the lipid cell membrane of the GI tract by at least 300, 250, 200, 190, 180, 170, 160, 150, 140, 130, 120, 110, 100, 90, 80, 70, 60, 50, 40, 30, 20, 10, 9, 8, 7, 6, 5, 4, 3, or 2 folds when compared with administering silymarin or silychristin without sulfoalkyl ether cyclodextrin.

In some embodiments, orally or parenterally (e.g. intraveneously) administering the composition described herein to a subject in need thereof can increase the amount of silydianin permeated across the lipid cell membrane of the GI tract by at least 300, 250, 200, 190, 180, 170, 160, 150, 140, 130, 120, 110, 100, 90, 80, 70, 60, 50, 40, 30, 20, 10, 9, 8, 7, 6, 5, 4, 3, or 2 folds when compared with administering silymarin or silydianin without sulfoalkyl ether cyclodextrin.

In some embodiments, orally or parenterally (e.g. intraveneously) administering the composition described herein to a subject in need thereof can increase the amount of Silybin A permeated across the lipid cell membrane of the GI tract by at least 600, 500, 480, 450, 425, 400, 380, 360, 350, 340, 320, 300, 280, 260, 250, 240, 220, 200, 175, 150, 125, 100, 90, 80, 70, 60, 50, 40, 30, 20, 10, 9, 8, 7, 6, 5, 4, 3, or 2 folds when compared with administering silymarin or silybin A without sulfoalkyl ether cyclodextrin.

In some embodiments, orally or parenterally (e.g. intraveneously) administering the composition described herein to a subject in need thereof can increase the amount of Silybin B permeated across the lipid cell membrane of the GI tract by at least 600, 500, 480, 450, 425, 400, 380, 360, 350, 340, 320, 300, 280, 260, 250, 240, 220, 200, 175, 150, 125, 100, 90, 80, 70, 60, 50, 40, 30, 20, 10, 9, 8, 7, 6, 5, 4, 3, or 2 folds when compared with administering silymarin or silybin B without sulfoalkyl ether cyclodextrin.

In some embodiments, orally or parenterally (e.g. intraveneously) administering the composition described herein to a subject in need thereof can increase the amount of isosilybin A permeated across the lipid cell membrane of the GI tract by at least 500, 400, 300, 280, 260, 250, 240, 220, 200, 190, 180, 170, 160 150, 140, 130, 120, 110, 100, 90, 80, 70, 60, 50, 40, 30, 20, 10, 9, 8, 7, 6, 5, 4, 3, or 2 folds when compared with administering silymarin or isosilybin A without sulfoalkyl ether cyclodextrin.

In some embodiments, orally or parenterally (e.g. intraveneously) administering the composition described herein to a subject in need thereof can increase the amount of isosilybin B permeated across the lipid cell membrane of the GI tract by at least 500, 400, 300, 280, 260, 250, 240, 220, 200, 190, 180, 170, 160 150, 140, 130, 120, 110, 100, 90, 80, 70, 60, 50, 40, 30, 20, 10, 9, 8, 7, 6, 5, 4, 3, or 2 folds when compared with administering silymarin or isosilybin B without sulfoalkyl ether cyclodextrin.

In some embodiments, orally orally administering the composition described herein to a subject in need thereof can achieve a % $F_{abs}$ for silybin A administration of greater than 0.5%, 1.0%, 2.0%, 3%, 4%, 5%, 6%, 7%, 8%, 9%, 10%, 15%, 20%, 25%, 30%, 40%, 50%, 60%, 70%, 80%, or 90%. In some embodiments, In some embodiments, orally orally administering the composition described herein to a subject in need thereof can achive a % $F_{abs}$ for silybin A administration in the range of about 0.5%-40%, 1.0%-30%, 2.0%-40%, 5%-10%, or 6% to 8%. In some embodiments, orally orally administering the composition described herein to a subject in need thereof can achive a % $F_{abs}$ for silybin A administration of lower than 10%, 15%, 20%, 25%, 30%, 40%, 50%, 60%, 70%, 80%, or 90%.

In some embodiments, orally administering the composition described herein to a subject in need thereof can increase the $F_{abs}$ for silybin A by at least 500, 400, 300, 280, 260, 250, 240, 220, 200, 190, 180, 170, 160 150, 140, 130, 120, 110, 100, 90, 80, 70, 60, 50, 40, 30, 20, 10, 9, 8, 7, 6, 5, 4, 3, or 2 folds when compared with administering silymarin or silybin A without sulfoalkyl ether cyclodextrin.

In some embodiments, orally orally administering the composition described herein to a subject in need thereof can achive a % $F_{abs}$ for silybin B administration of greater than 0.5%, 1.0%, 2.0%, 3%, 4%, 5%, 6%, 7%, 8%, 9%, 10%, 15%, 20%, 25%, 30%, 40%, 50%, 60%, 70%, 80%, or 90%. In some embodiments, In some embodiments, orally orally administering the composition described herein to a subject in need thereof can achive a % $F_{abs}$ for silybin B administration in the range of about 0.5%-40%, 1.0%-30%, 2.0%-40%, 5%-10%, or 6% to 8%. In some embodiments, orally orally administering the composition described herein to a subject in need thereof can achive a % $F_{abs}$ for silybin B administration of lower than 10%, 15%, 20%, 25%, 30%, 40%, 50%, 60%, 70%, 80%, or 90%.

In some embodiments, orally administering the composition described herein to a subject in need thereof can increase the $F_{abs}$ for silybin A by at least 500, 400, 300, 280, 260, 250, 240, 220, 200, 190, 180, 170, 160 150, 140, 130, 120, 110, 100, 90, 80, 70, 60, 50, 40, 30, 20, 10, 9, 8, 7, 6, 5, 4, 3, or 2 folds when compared with administering silymarin or silybin A without sulfoalkyl ether cyclodextrin.

In some embodiments, orally orally administering the composition described herein to a subject in need thereof can achive a % $F_{abs}$ for isosilybin A administration of greater than 0.5%, 1.0%, 2.0%, 3%, 4%, 5%, 6%, 7%, 8%, 9%, 10%, 11%, 12%, 13%, 14%, 15%, 20%, 25%, 30%, 40%, 50%, 60%, 70%, 80%, or 90%. In some embodiments, In some embodiments, orally orally administering the composition described herein to a subject in need thereof can achive a % $F_{abs}$ for isosilybin A administration in the range of about 0.5%-40%, 1.0%-30%, 2.0%-40%, 5%-15%, 6% to 15%, or 10% to 12%. In some embodiments, orally orally administering the composition described herein to a subject in need thereof can achive a % $F_{abs}$ for isosilybin A administration of lower than 10%, 15%, 20%, 25%, 30%, 40%, 50%, 60%, 70%, 80%, or 90%.

In some embodiments, orally administering the composition described herein to a subject in need thereof can increase the $F_{abs}$ for isosilybin B by at least 500, 400, 300, 280, 260, 250, 240, 220, 200, 190, 180, 170, 160 150, 140, 130, 120, 110, 100, 90, 80, 70, 60, 50, 40, 30, 20, 10, 9, 8, 7, 6, 5, 4, 3, or 2 folds when compared with administering silymarin or isosilybin B without sulfoalkyl ether cyclodextrin.

In some embodiments, orally orally administering the composition described herein to a subject in need thereof can achive a % $F_{abs}$ for isosilybin B administration of greater than 0.5%, 1.0%, 2.0%, 3%, 4%, 5%, 6%, 7%, 8%, 9%, 10%, 15%, 20%, 25%, 30%, 35%, 40%, 45%, 46.7%, 48%, 50%, 60%, 70%, 80%, or 90%. In some embodiments, In some embodiments, orally orally administering the composition described herein to a subject in need thereof can achive a % $F_{abs}$ for isosilybin B administration in the range of about 5%-90%, 10%-80%, 20%-70%, 30%-60%, or 40% to 50%. In some embodiments, orally orally administering the composition described herein to a subject in need thereof can achive a % $F_{abs}$ for isosilybin B administration of lower than 30%, 40%, 50%, 55%, 58%, 60%, 65%, 70%, 80%, or 90%.

In some embodiments, orally administering the composition described herein to a subject in need thereof can increase the $F_{abs}$ for isosilybin B by at least 500, 400, 300, 280, 260, 250, 240, 220, 200, 190, 180, 170, 160 150, 140, 130, 120, 110, 100, 90, 80, 70, 60, 50, 40, 30, 20, 10, 9, 8, 7, 6, 5, 4, 3, or 2 folds when compared with administering silymarin or isosilybin B without sulfoalkyl ether cyclodextrin.

Topical Compositions

Some embodiments relate to a topical composition containing silymarin or components of silymarin and sulfoalkyl ether cyclodextrin. The topical composition may be in any of the dosage forms which are generally suitable for topical administration such as a cream, ointment, gel, lotion, liniment, paste wash, shampoo, soap, spray or an emulsion.

The compositions described herein can also include a safe and effective amount of an anti-oxidant. The anti-oxidant is especially useful for providing protection against ultraviolet radiation that can cause increased scaling or texture changes in the stratum corneum and against other environmental agents that can cause skin damage. Anti-oxidants such as ascorbic acid (vitamin C) and its salts, ascorbic esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox™), gallic acid and its alkyl esters, especially propyl gallate, uric acid and its salts and alkyl esters, sorbic acid and its salts, lipoic acid, amines (e.g., N,N-diethylhydroxylamine, amino-gianidine), sulfitydryl compounds (e.g., glutathione), dihydroxy fumaric acid and its salts, lysine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts can be used. Other anti-oxidants/radical scavengers are selected from tocopherol sorbate and other esters of tocopherol. For example, the use of tocopherol sorbate in topical compositions and applicable herein is described in U.S. Pat. No. 4,847,071. Other examples of the anti-oxidants include BHA (butylated hydroxy anisole), BHT (butylated hydroxy toluene), retinoids, beta-carotene, ubiquinone, propyl gallate, alpha-tocopherol, superoxide dismutase, and polyphenols. In some embodiments, the composition includes one anti-oxidant. In some embodiments, the composition includes two or more anti-oxidants. In some embodiments, the composition can include ascorbic acid. In other embodiments, the composition can include retinoids.

A safe and effective amount of an anti-oxidant/radical scavenger can be added to the compositions described herein. The amount of the anti-oxidant in the composition can be in the range of from about 0.1% to about 10%, about 0.5% to about 5%, about 1% to 10%, or about 1% to 5% by weight, based on the total weight of the composition.

The composition described herein can contain one or more solvents. Suitable examples of solvent include water and a lower alcohol such as methanol, ethanol and isopropanol, and lactone. In some embodiments, the composition can contain water. In other embodiments, the composition can contain ethanol. In some embodiments, the composition can include one or more solvents selected from water, methanol, ethanol, isopropanol, lactone, or any combinations thereof. In some embodiments, the composition comprises phenoxyethanol, ethanol, PEG 400, and water.

The composition described herein can be in the form of a gel. In some embodiments, the composition comprises phenoxyethanol, ethanol, PEG 400, hydroxy cellulose and water. In some embodiments, the composition comprises phenoxyethanol. In some embodiments, the composition comprises ethanol. In some embodiments, the composition comprises PEG 400. In some embodiments, the composition comprises hydroxy cellulose. In some embodiments, the composition comprises water.

The composition described herein can contain, in addition to the aforementioned components, an oil component (0.1 to 50 weight %), so long as the oil component does not impede the effects of the composition. Examples of the oil component include glycerides such as castor oil, cocoa oil, mink oil, avocado oil, and olive oil; waxes such as beeswax, whale wax, lanolin, and carnauba wax; higher alcohols such as cetyl alcohol, oleyl alcohol, hexadecyl alcohol, lauryl alcohol, stearyl alcohol, isostearyl alcohol, and 2-octyldodecanol; esters such as isopropyl myristate, hexyl laurate, cetyl lactate, propylene glycol monostearate, oleyl oleate, hexadecyl 2-ethylhexanoate, and octyldodecyl myristate; hydrocarbon oils such as liquid paraffin, vaseline, squalane, and hydrogenated polyisobutene, silicone derivatives such as dimethylpolysiloxane, methylphenylpolysiloxane, polyether-modified silicone oil, epoxy-modified silicone oil, amino-modified silicone oil, and alkyl-modified silicone oil; and polypropylene glycol.

The composition can also contain an emulsifier for stabilizing such an oil component through emulsification. The emulsifier employed can be an anionic, amphoteric, cationic, or nonionic surfactant.

The composition described herein can also contain a perfume or a dye for improving its commercial value, or a preservative for preventing change over time in quality of the composition. The composition can also include at least one cosmetically or pharmaceutically acceptable excipient, diluent or carrier.

The composition described herein can include acceptable carriers and/or auxiliary agents necessary for the administration of the composition in the desired manner. Among the carriers and/or auxiliary agents are included excipients, thickeners, diluents, solvents, dispersants or adjuvants known to the expert of the art. Thickeners include, but are not limited to, water-soluble polymers such as those selected from the group consisting of modified celluloses, methylcellulose, ethylcellulose, hydroxyethylcellulose, hydroxyethylmethylcellulose, hydroxypropylcellulose, hydroxypropylmethylcellulose and carboxymethylcellulose, dextrans, gelatins, collagen, polyethylene glycol or polyvinyl pyrrolidone. Diluents and solvents include, but are not limited to, those selected from the group consisting of ethanol, polyethylene glycol, glycofurol, V-methyl-2-pyrrolidone, glycerol, propanediol, polypropylene glycol, benzyl alcohol or dimethylsulfoxide. Dispersants include, but are not limited to, surfactants selected from the group consisting of monoesters of fatty acids of polyoxyethylene sorbitan (Tween®, Emalex, Nikkol®, Hodag, Dacol or Liposorb®), fatty acid monoesters of sorbitan (Span®), 15-hydroxystearate polyethylene glycol (Solutol® HS15), fatty acid esters of polyethylene glycol (Crodet, Cithrol, Kessco®, Nikkol®, Mapeg®, Myrj, Tagat®, Aldo®, Capmul®, Glycerox, Lactomul®, or Emerest®), esters of glycol polyoxyethylene (Emulphor®), polyethoxylated castor oils (Cremophor®, Emalex, Eumulgin®, Nikkol® or Simusol®), fatty acid esters of polyglycerol (Nikkol Decaglyn, Polymuls, Caprol®), polyethylene glycol ethers (Volpo or Brij®), poloxamer (Lutrol® or Pluronic®), phenyl ethers of polyoxyethylene (Triton® or Igepal®), or mixtures thereof Preferably, the cosmetic or pharmaceutical composition described herein also contains one or more acceptable excipients such as humectants, pH buffers, preservatives, bactericidal and fungicidal agents, absorption retardants, absorption accelerators, or any other excipient known to the expert of the art.

The compositions described herein can also contain a safe and effective amount of an anti-cellulite agent. In accordance with the present disclosure, anti-cellulite agents are substances which i) exhibit beta-stimulation (adrenergic beta-agonists) to further enhance lipolysis into the dermal adipocytes; ii) act as collagen synthesis stimulators; iii) improve poor vascularity conditions associated to the cellulitic areas by a vasokinetic activity; or iv) exert adenylate cyclase agonist and/or anti-phosphodiesterase activities so as to accelerate the reduction of fatty deposits located in the cellulite-affected area. Suitable anti-cellulite agents suitable for use with the compositions described herein can include, but are not limited to, xanthine compounds (e.g., caffeine, theophylline, theobromine, and aminophylline), ascorbates, triterpenoids such as Asiatic acid, inositol phosphate and phytic acid, nicotinates, salicylates including methyl salicylate, and natural-product extracts such as alkaloids and plant extracts containing flavones. Anti-cellulite agents are preferably employed in a proportion of at least 0.05%, generally in a proportion of from about 0.05% to about 20%, preferably from about 0.10% to about 10% by weight of the composition in order to maximize efficacy at optimum cost.

The compositions described herein can also contain a safe and effective amount of a topical anesthetic. Examples of topical anesthetic drugs suitable for inclusion in the compositions described herein include but are not limited to benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof. In one embodiment of the present disclosure, the amount of topical anesthetic in the compositions ranges from about 0.001% to about 10%, such as from about 0.01% to about 5% such as from about 0.05% to about 2% by weight, based on the total weight of the composition.

One or more tanning compounds can be included in the compositions described herein. When present, the compositions can contain from about 0.1% to about 20%, or from about 2% to about 7%, or from about 3% to about 6%, by weight of the composition, of dihydroxyacetone as an artificial tanning compound. Exemplary tanning compounds suitable for use with the instant compositions include dihydroxyacetone (and derivatives and analogs thereof), which is also known as DHA or 1,3-dihydroxy-2-propanone, as well as other self-tanning compounds. This material is represented by the chemical formula C3H603, and can exist as a mixture of monomers and dimers, with the dimers predominating in the solid crystalline state. Upon heating or melting, the dimers break down to yield the monomers. This conversion of the dimeric form to the monomeric form also occurs in aqueous solution. Dihydroxyacetone is also known to be more stable at acidic pH values.

One or more skin-lightening agents can be included in compositions described herein. When used, the compositions can contain from about 0.1% to about 10%, or from about 0.2% to about 5%, or from about 0.5% to about 2%, by weight of the composition, of a skin lightening agent. Suitable skin lightening agents include but are not limited to kojic acid, arbutin, ascorbic acid and derivatives thereof (e.g., magnesium ascorbyl phosphate or sodium ascorbyl phosphate), and extracts (e.g., mulberry extract, placental extract). Skin lightening agents suitable for use herein also include those described by Rendon, M. I., et al. [Dermatol. Surg., Vol. 31 (7, pt. 2), pp. 886-889 (2005)], and Zhu, W., et al. [Journal of Investigative Dermatology, Symposium Proceedings, Vol. 13 (1), pp. 20-24 (2008)].

One or more skin soothing and skin healing compounds can be included in the compositions described herein. Skin soothing or skin healing compounds suitable for use herein include panthenoic acid derivatives (including panthenol, dexpanthenol, ethyl panthenol), aloe vera, allantoin, bisabolol, and dipotassium glycyrrhizinate. A safe and effective amount of a skin soothing or skin healing compound can be added to the present composition, for example, from about 0.1% to about 30%, or from about 0.5% to about 20%, or from about 0.5% to about 10%, by weight of the composition formed.

One or more antimicrobial and/or anti-fungal compounds can be included in the compositions described herein. Such compounds are capable of destroying microbes, preventing the development of microbes or preventing the pathogenic action of microbes. A safe and effective amount of an anti-microbial or anti-fungal compound can be added to the present compositions, for example, from about 0.001% to about 10%, or from about 0.01% to about 5%, or from about 0.05% to about 2%, by weight of the composition formulated.

Examples of antimicrobial and antifungal compounds suitable for use with the presently described compositions include but are not limited to β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netihnicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amantadine hydrochloride, amantadine sulfate, octopirox, parachlorometa xylenol, nystatin, tolnaftate, zinc pyrithione and clotrimazole.

Examples of particular compounds useful herein include those selected from benzoyl peroxide, 3-hydroxy benzoic acid, glycolic acid, lactic acid, 4-hydroxy benzoic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neocycin sulfate, and mixtures thereof.

One or more sunscreen compounds can be included in the compositions described herein. As used herein, "sunscreen compound" includes both sunscreen agents and physical sun blocks. Suitable sunscreen compounds can be either organic or inorganic, and preferably are GRAS compounds.

Inorganic sunscreens useful herein include the following metallic oxides; titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. When used herein, the inorganic sunscreens can be present in the amount of from about 0.1% to about 20%, or from about 0.5% to about 10%, or from about 1% to about 5%, by weight of the composition.

A wide variety of conventional organic sunscreen compounds are suitable for use herein. In "The Handbook of Cosmetic Science and Technology, 3rd Edition" [Marc Paye, H. I. Maibach, & A. O. Barel, eds.; 2009, which is incorporated herein by reference in its entirety], there are disclosed numerous suitable compounds for use as sunscreen compounds in the compositions of the present disclosure, including but not limited to p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylate esters (amyl, phenyl, octyl, benzyl, menthyl, glyceryl, and di-propyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one), terephthalylidene dicamphor sulfonic acid and 4-isopropyl-di-benzoylmethane.

Desirable compounds suitable for use in the compositions of the present disclosure include but are not limited to 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, di galloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds.

In some embodiments, the organic sunscreen compounds used in the compositions described herein are 2-ethylhexyl-p-methoxycinnamate, butylmethoxydibenzoyl-methane, 2-hydroxy-4-methoxybenzo-phenone, 2-phenylbenzimidazole-5-sulfonic acid, octyldimethyl-p-aminobenzoic acid, octocrylene and mixtures thereof.

Useful sunscreen compounds are also described by Gonzalez, et al. [G. Ital. Dermatol. Venereol., Vol. 145(4), pp. 515-523 (2010), which is incorporated herein by reference in its entirety], as well as other sunscreen compounds known in the arts. The sun-screening agents which are particularly desirable in accordance with at least one aspect of the present disclosure include those which have, in a single molecule, two distinct chromophore moieties that exhibit different ultra-violet radiation absorption spectra. One of the chromophore moieties absorbs predominantly in the UVB radiation range and the other absorbs strongly in the UVA radiation range. Desirable members of this class of sun-screening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy) benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy) benzophenone; and N,N-di-(2-ethylhexyl)-4-aminobenzoic acid ester of 4-(2-hydroxyethoxy)dibenzoylmethane and mixtures thereof. Other desirable sunscreen compounds include 4,4'-t-butylmethoxydibenzoyl-methane, 2-ethylhexyl-p-methoxycinnamate, phenyl benzimidazole sulfonic acid, and octocrylene.

A safe and effective amount of the organic sunscreen compound can be used, typically from about 1% to about 20%, more typically from about 2% to about 10% by weight of the composition. Exact amounts will vary depending upon the sunscreen or sunscreens chosen and the desired Sun Protection Factor (SPF).

The compositions described herein can contain a particulate material, for example, a inorganic, metallic oxide. These particulates can be coated or uncoated, charged or uncharged. Charged particulate materials are disclosed, for example, in U.S. Pat. No. 5,997,887, to Ha, et al. Particulate materials suitable for use with the compositions described herein include but are not limited to bismuth oxychloride, iron oxide, mica, mica treated with barium sulfate and TiO2, silica, nylon, polyethylene, talc, styrene, polypropylene, ethylene/acrylic acid copolymer, sericite, titanium dioxide, bismuth oxychloride, iron oxide, aluminum oxide, silicone resin, barium sulfate, calcium carbonate, cellulose acetate, polymethyl methacrylate, and mixtures thereof. Inorganic particulate materials suitable for use herein also include metal oxides wherein the metals are from the transition metal series of the Periodic Table of Elements, including but not limited to Ti02, ZnO, or Zr02, all of which are commercially available from a number of sources. One example of a suitable particulate material contains the material available from U.S. Cosmetics (e.g., the TRONOX® TiO2 series, such as TRONOX® CR-837, a rutile TiO2). Particulate materials can be present in the compositions disclosed herein in levels ranging from about 0.01% to about 2%, or from about 0.05% to about 1.5%, or from about 0.1% to about 1%, by weight of the composition.

The compositions described herein can contain a conditioning agent selected from humectants, moisturizers, or skin conditioners. A variety of these materials can be employed and each can be present at a level of from about 0.01% to about 20%, more preferably from about 0.1% to about 10%, and still more preferably from about 0.5% to about 7% by weight of the composition. These materials include, but are not limited to, guanidine; urea; glycolic acid and glycolate salts (e.g. ammonium and quaternary alkyl ammonium); lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fucose, glucosamine); hyaluronic acid; lactamide monoethanolamine; acetamide monoethanolamine; panthenol; allantoin; and mixtures thereof. Also useful herein are propoxylated glycerols.

Also useful as conditioning agents are various $C_1$-$C_{30}$ monoesters and polyesters of sugars and related materials. These esters are derived from a sugar or polyol moiety and one or more carboxylic acid moieties.

Desirable conditioning agents for use with the instant composition are selected from urea, guanidine, sucrose polyester, panthenol, dexpanthenol, allantoin, and combinations thereof.

The compositions described herein can contain one or more thickening agents, in an amount ranging from about 0.1% to about 5%, or from about 0.1% to about 4%, or from about 0.25% to about 3%, by weight of the composition. Non-limiting classes of thickening agents suitable for use with the present compositions include, but are not limited to, those selected from the group consisting of carboxylic acid polymers, crosslinked polyacrylate polymers, polyacrylamide polymers, polysaccharides, and gums, as well as combinations thereof.

a) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in compositions described herein are more fully described in U.S. Pat. No. 5,087,445, to Haffey, et al., and in the CTFA International Cosmetic Ingredient Dictionary and Handbook, Eleventh Edition, 2006 (vols. 1-4), both of which are incorporated herein by reference in their entirety.

Examples of commercially available carboxylic acid polymers useful herein include the carbomers, which are homopolymers of acrylic acid crosslinked with allyl ethers of sucrose or pentaerytritol. The carbomers are available as the CARBOPOL™ 900 series from B.F. Goodrich (e.g., CARBOPOL™). In addition, other suitable carboxylic acid polymeric agents include copolymers of C-io-30 alkyl acrylates with one or more monomers of acrylic acid, methacrylic acid, or one of their short chain (i.e., d. 4 alcohol) esters, wherein the crosslinking agent is an allyl ether of sucrose or pentaerytritol. These copolymers are known as acrylates/C1-30 alkyl acrylate crosspolymers and are commercially available as Carbopol™ 1342, Carbopol™ 1382, Pemulen TR-1, and Pemulen TR-2, available from B.F. Goodrich. In other words, examples of carboxylic acid polymer thickeners useful herein are those selected from carbomers, acrylates/C1-C30 alkyl acrylate crosspolymers, and mixtures thereof.

b) Crosslinked Polyacrylate Polymers

The compositions described herein can optionally contain crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers include those described in U.S. Pat. No. 5,100,660, to Hawe et al., which is incorporated herein by reference in its entirety.

c) Polyacrylamide Polymers

The compositions described herein can optionally contain polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Trade name SEPIGEL™ 305, available from the Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, and Hypan SS201 available from Lipo Chemicals, Inc., (Patterson, N.J.).

d) Polysaccharides

A wide variety of polysaccharides are useful herein. "Polysaccharides" refer to gelling agents that contain a backbone of repeating sugar (i.e., carbohydrate) units. Non-limiting examples of polysaccharide gelling agents include those selected from cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. In these polymers, the hydroxy groups of the cellulose polymer is hydroxyalkylated (preferably hydroxyethylated or hydroxypropylated) to form a hydroxyalkylated cellulose that is then further modified with a C10-C30 straight chain or branched chain alkyl group through an ether linkage. Typically these polymers are ethers of C10-C30 straight or branched chain alcohols with hydroxyalkylcelluloses. Examples of alkyl groups useful herein include those selected from stearyl, isostearyl, lauryl, myristyl, cetyl, isocetyl, cocoyi (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is available under the trade name NATROSOL™ CS Plus from Aqualon Corporation (Wilmington, Del.).

Other useful polysaccharides include scleroglucans that are a linear chain of (1→3) linked glucose units with a (1→6) linked glucose every three units, a commercially available example of which is CLEAROGEL™ CS1 1 from Michel Mercier Products Inc. (Mountainside, N.J.).

Other thickening and gelling agents useful herein include materials that are primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof. Compositions described herein can therefore include desirable thickening agents such as carboxylic acid polymers, crosslinked polyacrylate polymers, polyacrylamide polymers, and mixtures thereof, more preferably selected from carboxylic acid polymers, polyacrylamide polymers, and mixtures thereof.

Where necessary, the compositions further include water sufficient to provide the remaining weight of the composition. Deionized or distilled water can be employed.

Inorganic agents with or without organic modifications can form a part of the compositions disclosed herein. The total amount of these agents in the composition is in the range from about 0.5 to about 5% by weight of the composition. The inorganic agent preferably comprises at least one smectite clay. Preferably, at least 20% by weight of the inorganic agent is a smectite clay, more preferably at least 30%, even more preferably at least 40% and optimally at least 50% by weight of the inorganic agent is a smectite clay.

Preferably the smectite clay is chosen from the group consisting of: aluminum silicates, such as the montmorillonites (bentonites, hectorites and derivatives thereof); purified magnesium aluminum silicates (commercially available as VEEGUM™ in various grades); purified sodium magnesium silicates (commercially available as LAPONITE™ in various grades); organically modified smectites including tetra alkyl and/or trialkyi ammonium smectites (organically modified montmorillonite clays) such as quaternium-18 bentonite, quaternium-18 hectorite, stearalkonium bentonite and stearalkonium hectorite; and mixtures thereof.

Montmorillonites represent clay minerals, which belong to the dioctahedral smectites, and are materials which swell in water but do not become plastic. The layer packets in the 3-layer structure of the montmorillonites can swell as the result of reversible incorporation of water (in a 2-7 fold amount) and other substances, such as, for examples, alcohols, glycols, pyridine, cc-picoline, ammonium compounds, hydroxyaluminosilicate ions, etc.

Since montmorillonite has a large capacity for ion exchange, aluminum can be replaced by Mg, Fe(II), Fe(III), Zn, Pb, Cr, Cu and others. The resulting negative charge of the octahedral layers is balanced by cations, in particular Na+ (sodium montmorillonite) and Ca2+ (calcium montmorillonite) in interlayer positions.

The organophilization of montmorillonite or bentonites (exchange of the interlayer cations for quaternary alkylammonium ions) produces products (bentones), which are also useful herein.

The balance of the inorganic agent can be selected individually or as mixtures from the following: silicas, silicates, colloidal silicas, silicate pigments in which the free —OH (hydroxyl) groups on the surface of the particles have been (completely or partially) organically modified, chalk, talc, kaolin, Fullers earth, sodium polyacrylate, chemically modified magnesium aluminum silicate, hydrated aluminum silicate, zinc oxide, titanium oxide, and mixtures thereof.

The composition may be provided in a substance or carrier that facilitates penetration and/or includes a controlled release mechanism. Examples of controlled release mechanisms include microsponges, microspheres, liposomes, microcapsules, polymers, gels, hydrophilic gums, and/or other colloidal drug delivery systems. Hence, a cosmetic composition of the disclosure may include one or more of: microsponges, microspheres (e.g., micelles), and/or liposomes.

For instance, the composition may include a controlled release mechanism such as a microsponge. Microsponges are microscopic, porous spherical sponges. Generally, microsponges are porous microspheres having a myriad of interconnected voids of particle size range 5-300 μm. Depending upon the size, the total pore length may range up to 10 ft and pore volume may range up to 1 ml/g. A suitable microsponge of the disclosure has the capacity to entrap a prostaglandin based compound and/or other cosmetically suitable compound, such as an emollient, surfactant, essential oils, sunscreen and anti-infective, etc. and can be used with the prostaglandin based compound of the disclsoure as a topical carrier system. The prostaglandins based compound of the disclosure can be incorporated in to a micrsoponge and formulated into creams, lotions, balms, and powders. Other forms of microspheres may be incorporated into the present formulations of the disclosure, such as those formed from lipids, typically charged lipids, such as phospholipids.

Further, the composition may include a controlled release mechanism such as a microsphere or micelle. Micelles are comprised of surfactant molecules that are arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles may include, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl 8 dodecyl ether, polyoxyl 12 dodecyl either, nonoxynol 10 and nonoxynol 30.

Additionally, the composition may include and/or be used in combination with a controlled release mechanism such as a liposome. Liposomes are vesicles having a lipid wall comprising a lipid bilayer. Liposomal preparations for use in the instant disclosure include cationic (positively charged), anionic (negatively charged) and neutral preparations. Cationic liposomes are readily available. For example, N-[1-2,3-dioleyloxy)propyl]-N,N,N-triethylammonium liposomes are commercially available, Anionic and neutral liposomes are commercially and readily available as well, or can be easily prepared using readily available materials. Such materials may include phosphatidyl choline, cholesterol, phosphatidyl ethanolamine, dioleoylphosphatidyl choline, dioleoylphosphatidyl glycerol, dioleoylphoshatidyl ethanolamine, among others. These materials may be mixed with N-[1-2,3-dioleyloxy)propyl]-N,N,N-triethylammonium (DOTMA) in appropriate ratios. Methods for making liposomes using these materials are well known in the art.

The cosmetic compositions of the present disclosure may also contain agents that sooth or condition the skin and hair ("conditioning agents"). One such agent is panthenol, a pro-vitamin moisturizing agent, such as Vitamin E. Panthenol is may be incorporated into the cosmetic formulations of the disclosure and may promote the penetration of the prostaglandins based compound into the skin and hair. Panthenol derivatives (e.g., ethyl panthenol) also find use in the compositions of the disclsoure as do agents such as aloe vera, pantothenic acid and its derivatives, allantoin, bisabolol, and dipotassium glycyrrhizinate. For instance, a hair conditioning agent may be a hydrolyzed wheat protein, which may be included so as to improve the hair's resilience and promote body by penetrating the hair shaft to repair damage and is provided in an amount from 5 to 25% by weight.

Other hair and skin conditioning/soothing agents may also be included in the subject compositions. For example, one or more anti-microbial agents can be included in the composition, e.g., leuconostoc/radish root ferment filtrate. If desired, a pH stabilizer such as triethanoolamine can be included in the composition, as can antioxidants, such as ascorbyl palmitate, tocopheryl acetate, L-camosine, Carotenoids, CoEnzyme Q10, Vitamin A, B, C, D, and/or E, Green Tea extract, Selenium or Zinc; or a moisturizing agent such as xodium hyaluronate; or a chelator, such as ethylenediamine, porphine, EDTA (ethylenediamine tetraacetate), DMSO, DMSO2 (MSM), sodium phytate, DTPA (Diethylenetriaminepentaacetic acid) or NTA ACID (Nitrilotriacetic acids.

Other minor components may also be incorporated into the cosmetic compositions. These ingredients may include coloring agents, opacifiers and perfumes. Amounts of these other minor components may range anywhere from 0.00.1% or less up to 20% or more by weight of the composition. The form of the composition can vary depending on the use of the composition. The composition can be in a solid or liquid form.

Oral Compositions

Some embodiments relate to an oral composition containing silymarin or components of silymarin and sulfoalkyl ether cyclodextrin described herein. The oral composition may be in any of the dosage forms which are generally used for dietary supplements such as liquids, gels, powders, tablets, caplets, capsules, gel, caps, food additives, drops, beverages, pills, lozenges, rinses, pastes, gums and soft gels.

Dietary supplement compositions described herein may also contain additives, such as water, alcohols, oils (mineral, vegetable, animal and synthetics), glycols, colorants, preservatives, emulsifiers, gelling agents, gums, esters, hormones, steroids, anti-oxidants, silicones, polymers, fragrances, flavors, sunscreens, other active ingredients, acids, bases, buffers, vitamins, minerals, salts, polyols, proteins and their derivatives, essential oils, other enzymes, co-enzymes and extracts, surfactants, anionics, non-ionics, ionics, waxes, lipids, stabilizers, celluloses, glycans, amines, solubilizers, thickeners, sugars and sugar derivatives, ceramides, sweeteners and the like.

Suitable optional carriers include but are not limited to, for example, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, wheat germ oil, tallow, beef tallow, butter, chicken fat, lard, dairy butterfat, shea butter or combinations thereof.

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. Alternatively or in combination with one of the above identified carrier, beeswax can be used as a suitable carrier, as well as suspending agents such as silica (silicon dioxide).

The formulations described herein can further include various ingredients to help stabilize, or help promote the bioavailability of the components of the beneficial compositions or serve as additional nutrients to an individual's diet. Suitable additives can include vitamins and biologically-acceptable minerals. Non-limiting examples of vitamins include vitamin A, B vitamins, vitamin C, vitamin D, vitamin E, vitamin K and folic acid. Non-limiting examples of minerals include iron, calcium, magnesium, potassium, copper, chromium, zinc, molybdenum, iodine, boron, selenium, manganese, derivatives thereof or combinations thereof. These vitamins and minerals may be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

Vitamin(s), if present, are present in the composition described herein in an amount ranging from about 5 mg to about 500 mg. More particularly, the vitamin(s) is present in an amount ranging from about 10 mg to about 400 mg. Even more specifically, the vitamin(s) is present from about 250 mg to about 400 mg. Most specifically, the vitamin(s) is present in an amount ranging from about 10 mg to about 50 mg. For example, B vitamins are in usually incorporated in the range of about 1 milligram to about 10 milligrams, i.e., from about 3 micrograms to about 50 micrograms of B12. Folic acid, for example, is generally incorporated in a range of about 50 to about 400 micrograms, biotin is generally incorporated in a range of about 25 to about 700 micrograms and cyanocobalamin is incorporated in a range of about 3 micrograms to about 50 micrograms.

Mineral(s), if present, are present in the composition described herein in an amount ranging from about 25 mg to about 1000 mg. More particularly, the mineral(s) are present in the composition ranging from about 25 mg to about 500 mg. Even more particularly, the mineral(s) are present in the composition in an amount ranging from about 100 mg to about 600 mg.

Various additives can be incorporated into the present compositions. Optional additives of the present composition include, without limitation, hyaluronic acid, phospholipids, starches, sugars, fats, antioxidants, amino acids, proteins, flavorings, coloring agents, hydrolyzed starch(es) and derivatives thereof or combinations thereof.

As used herein, the term "phospholipid" is recognized in the art, and refers to phosphatidyl glycerol, phosphatidyl inositol, phosphatidyl serine, phosphatidyl choline, phosphatidyl ethanolamine, as well as phosphatidic acids, ceramides, cerebrosides, sphingomyelins and cardiolipins.

Some embodiments include pharmaceutical compositions for use in treatment of the conditions described above. Standard pharmaceutical formulation techniques can be used, such as those disclosed in Remington's The Science and Practice of Pharmacy, 21st Ed., Lippincott Williams & Wilkins (2005), incorporated herein by reference in its entirety.

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents. Often the formulation will include an acceptable carrier, such as an oil, or other suspending or emulsifying agent.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

The compositions described herein can comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Preparations for oral administration may be suitably formulated to give controlled release of the active compound.

Alternative Routes of Administration

In addition to the topical and oral administration described above, the compositions described herein may take other suitable form of administration, including, for example, buccal, systemic, injection, transdermal, rectal, vaginal, etc., or a form suitable for administration by inhalation or insufflation. Standard administration techniques can be used, such as those disclosed in Remington's The Science and Practice of Pharmacy, 21st Ed., Lippincott Williams & Wilkins (2005), incorporated herein by reference in its entirety.

Method of Preparation

The compositions described herein are generally prepared by conventional methods known in the art for making topical compositions or dietary supplement compositions. These methods typically involve mixing of the ingredients in one or more steps to a relatively uniform state, with or without heating, cooling, application of vacuum, and the like.

The aqueous solubility of the active ingredient silymarin or components of silymarin can be increased by the formation of a complex, preferably an inclusion complex, with the SAE-CD. Various methods known in the art for preparing a pharmaceutical composition can be used to prepare the silymarin (or components of silymarin) and SAE-CD complexes, including the solution method, co-precipitation method, the slurry method, the kneading method and the grinding method. See T. Loftsson, Pharmaceutical Technology, 1999, 12, 41-50, which is incorporated herein by reference in its entirety.

In the solution method, the active ingredient, either as a solid or in a solution, is added to a solution containing an excess amount of SAE-CD. It is also possible to add an excess of the active ingredient to an aqueous SAE-CD solution. The mixture is agitated, and may optionally be heated, until an equilibrium is reached, which may take several hours or several days. The equilibrated solution is then filtered or centrifuged to give a clear solution of the drug-cyclodextrin complex. The clear solution can be directly used in subsequent composition formation, or a solid complex can be obtained by removal of the water by evaporation (such as spray-drying), sublimation (such as lyophilization) or other drying means well known in the art.

A solid complex may also be obtained by the precipitation method. The SAE-CD complexes can precipitate upon cooling of the solution. Otherwise, a solvent in which the complex has minimal solubility, typically an organic solvent, is used to precipitate the solid complex. The precipitate containing the complex can then be filtered or centrifuged to obtain a solid active ingredient and SAE-CD complex.

Another method of preparing a solid complex mixture is to grind a dry mixture of the active ingredient and SAE-CD in a sealed container which is then gently heated to a temperature between 60-140° C. If the drug is poorly water-soluble, the slurry or kneading methods can be employed. The active ingredient and SAE-CD can be suspended in water to form a slurry, which is similarly stirred and/or heated to equilibration. The complex can be collected by filtration or by evaporation of the water. The kneading method is similar to the slurry method, whereby the drug and cyclodextrin are mixed with a minimal amount of water to form a paste. The complex can be isolated by methods similar to those discussed above.

There are various physicochemical methods to determine the formation of an inclusion complex in solution, including UN, circular dichroism and fluorescence spectroscopy. Nuclear magnetic resonance and potentiometry can also show complexation. Solid cyclodextrin complexes can be studied by powder X-ray diffractometry, differential scanning calorimetry or thermogravimetry.

In one exemplary non-limiting general procedure for preparing a composition for topical administration, sulfoalkyl ether cyclodextrin, silymarin or components of silymarin, and other ingredients in the composition are combined and dispersed in suitable solvents such as water (in some instances, pre-dispersions of selected components, such as in a mineral oil or the like, are available to facilitate the procedure). Then, emollients, emulsifiers, lipophilic components (consistency factors) are combined and melted at room temperature or an elevated temperature. Stabilizers (thickeners) may then be dispersed separately under stirring in the water phase until homogeneous gel is formed and heated to 80° C. The two mixtures are combined progressively to form the emulsion, via mixing under intensive stirring until emulsion is formed. Gentle mixing continues while the emulsion is cooled. Sensitive components like the actives described herein (e.g., silymarin or components or silymarin), special additives, and preservatives can be added after the mixture has been cooled (e.g., to a temperature ranging from about 20-40° C.), in order to keep their properties intact.

In another exemplary non-limiting procedure, a composition for oral administration can be prepared by first mixing silymarin (or components or silymarin) and sulfoalkyl ether cyclodextrin in water at a predetermined ratio to provide a mixture and then drying the mixture to form a powder. The dried powder is then combined with additional ingredients to form the nutraceutical composition. The composition can be made into the form of a capsule, pill, tablet, or soft gel.

Silymarin can be prepared by any methods known in the art. One nonlimiting example for silymarin preparation can include the following procedures: The seeds of *S. marianum* are partially defatted by pressing, which lowers the fat content from ca 25% to ca 8%; then the seeds are extracted with acetone (alternatively ethanol, methanol or ethyl acetate can be used); acetone extract is partially evaporated and remaining fat is removed by hexane extraction; crude silymarin (complex) precipitates after further evaporation; pure silybin is prepared by dissolving silymarin in abs. ethanol followed by addition of about 10% of water. Crude silybin, which precipitates can be further purified by recrystallization from ethanol.

Some embodiments relate to methods for preparing the gel formulation described herein. In some embodiments, the silymarin and sulfoalkyl ether cyclodextrin may be combined with any combination of components described above in purified water using conventional mixing; after the silymarin are fully dissolved or after the mixture is filtered to remove any undissolved silymarin, additional solvent can be added to maintain the composition stability; then a gelling agent such as hydroxypropyl cellulose can be added until the gelling agent is fully hydrated. Following hydration of the gelling agent, the pH and viscosity may be adjusted using known methods to achieve a gel having an appropriate pH. In other embodiments, various combinations of components may be combined in purified water by conventional mixing and silymarin (and/or sulfoalkyl ether cyclodextrin) may then be added to the mixture. In some embodiments, sulfoalkyl ether cyclodextrin, organic solvent (e.g. ethanol), preservative (e.g., phenoxytthanol), and emulsifier (e.g., PEG 400) can be combined in purified water based on the ratios described herein to prepare a solvent system; this solvent system is then combined with silymarin using conventional mixing until silymarin reaches its maximum solubility in the solution; the solution saturated with silymarin can then undergo centrifugation and filtration; the resulting supernate or filtrate can then be diluted with the solvent system (e.g., adding 10% more solvent system by weight); the diluted solution can then be combined with the gelling agent (e.g., hydroxypropyl cellulose) to form a gel. The pH, viscosity, opaqueness, and/or density may be adjusted to achieve a gel which is cosmetically acceptable.

One method for quickly preparing saturated silymarin solution can include combining silymarin (e.g. 155 mg) and sulfoalkyl ether cyclodextrin solution (e.g., 0.1M) at a temperature that is between 50° C. to 85° C. and mixing the solution until it reaches equilibrium (e.g., 1 hour). The solution is then centrifuged and the supernatant is saturated with silymarin and can be used for preparing various formulations.

Hot Extraction Process

Some embodiments relate to a composition comprising silymarin or one or more silymarin components selected from the group consisting of taxifolin, silychristin A, silydianin, silychristin B, silybin A, silybin B, 2,3-cis-silybin A, 2,3-cis-silybin B, isosilybin A, isosilybin B, or 2,3-cis-isosilybin; and sulfoalkyl ether cyclodextrin, wherein the composition is prepared by a process described herein.

Some embodiments relate to a process of preparing a composition comprising silymarin or one or more silymarin components selected from the group consisting of taxifolin, silychristin A, silydianin, silychristin B, silybin A, silybin B, 2,3-cis-silybin A, 2,3-cis-silybin B, isosilybin A, isosilybin B, or 2,3-cis-isosilybin; and sulfoalkyl ether cyclodextrin, the process includes:

combining in a aqueous medium the silymarin or one or more components of silymarin and sulfoalkyl ether cyclodextrin at an elevated temperature that is greater than 25° C. to form a solution; and purifying the solution.

In some embodiments, purifying the solution includes conducting one or more separations to remove one or more undissolved components from the solution. In some embodiments, purifying the solution includes filtering the solution.

In some embodiments, combining the silymarin or one or more components of silymarin and sulfoalkyl ether cyclodextrin includes combining them in a sealed container. In some embodiments, combining the silymarin or one or more components of silymarin and sulfoalkyl ether cyclodextrin includes combining them without exposure to oxygen.

In some embodiments, the process further includes maintaining the solution at the elevated temperature for about 10 mins, 20 mins, 30 mins, 40 mins, 50 mins, 60 mins, 70 mins, 80 mins, 90 mins, 100 mins, 110 mins, or 120 mins. In some embodiments, the process further includes maintaining the solution at the elevated temperature for about 60 mins. In some embodiments, the process further includes maintaining the solution at the elevated temperature for about 10 mins to 120 mins, about 20 mins to about 100 mins, about 30 mins to about 90 mins, or about 40 mins to about 80 mins.

In some embodiments, the process further includes cooling the solution to room temperature prior to conducting the separation step. In some embodiments, the cooling step includes gradually cooling the solution to room temperature in about 10 mins, 20 mins, 30 mins, 40 mins, 50 mins, 60 mins, 70 mins, 80 mins, 90 mins, or 100 mins. In some embodiment, the cooling step included a sealed container having the solution in a water bath for about 10 mins, 20 mins, 30 mins, 40 mins, 50 mins, 60 mins, 70 mins, 80 mins, 90 mins, or 100 mins.

In some embodiments, conducting the separation to remove undissolved components includes a process selected from: ultrafiltration, diafiltration, centrifugation, extraction, solvent precipitation, and dialysis. In some embodiments, the separation includes centrifugation.

In some embodiments, the process further includes dissolving a sulfoalkyl ether cyclodextrin in an aqueous medium to form a sulfoalkyl ether cyclodextrin solution prior to combining the sulfoalkyl ether cyclodextrin and silymarin or silymarin components. In some embodiments, the sulfoalkyl ether cyclodextrin solution has a concentration of about 5 mM, 10 mM, 20 mM, 30 mM, 40 mM, 50 mM, 60 mM, 70 mM, 80 mM, 90 mM, 100 mM, 150 mM, 200 mM, 300 mM, 400 mM, 500 mM, 600 mM, 700 mM, 800 mM, 900 mM, or 1M. In some embodiments, the sulfoalkyl ether cyclodextrin solution has a concentration in the range of about 5 mM to about 900 mM, about 10 mM to about 800 mM, about 10 mM to about 500 mM, about 10 mM to about 250 mM, about 20 mM to about 150 mM, about 20 mM to about 120 mM, or about 20 mM to about 100 mM.

In some embodiments, combining in an aqueous medium the silymarin or one or more components of silymarin and sulfoalkyl ether cyclodextrin includes adding an excess amount of silymarin or silymarin components. In some embodiments, combining in an aqueous medium the silymarin or one or more components of silymarin and sulfoalkyl ether cyclodextrin includes adding more than 40 mg, 50 mg, 60 mg, 70 mg, 80 mg, 90 mg, 100 mg, 120 mg, 160 mg, 180 mg, 200 mg, 220 mg, 250 mg, 260 mg, 280 mg, 300 mg, 320 mg, 340 mg, 350 mg, 360 mg, 380 mg, 400 mg, 450 mg, or 500 mg of silymarin per 1 ml of aqueous medium, In some embodiments, the silymarin or one or more silymarin components and sulfoalkyl ether cyclodextrin in the composition form a complex.

In some embodiments, the silymarin or the one or more components of silymarin and sulfoalkyl ether cyclodextrin are combined in water. In some embodiments, the silymarin or one or more components of silymarin and sulfoalkyl ether cyclodextrin are combined in a solvent that is a mixture of water and alcohol.

In some embodiments, the silymarin or one or more components of silymarin and sulfoalkyl ether cyclodextrin are combined to form a solution and the solution is then kept at a temperature in the range of about 30° C. to about 100° C., about 40° C. to about 100°, 50° C. to about 100° C., about 60° C. to about 100° C., about 70° C. to about 100° C., about 40° C. to about 90° C., about 40° C. to about 80° C., about 50° C. to about 80° C., about 60° C. to about 80° C., or about 70° C. to about 75° C. In some embodiments, the silymarin or one or more components of silymarin and sulfoalkyl ether cyclodextrin are combined to form a solution and the solution is then kept at a temperature of about 50° C., 60° C., 65° C., 70° C., 75° C., 80° C., 85° C., 90° C., or 95° C.

In some embodiments, the process further includes lyophilizing or spray drying the composition after conducting the separation step.

The hot extraction process described herein can prepare a silymarin composition that is supersaturated at room temperature and has a solubility that is greater than the composition prepared by combining the silymarin or silymarin components and sulfoalkyl ether cyclodextrin at ambient temperature.

Method of Selective Enrichment

Some embodiments relate to a method of increasing or enhancing the amount of a first component in a silymarin composition, the method comprising combining the silymarin composition and sulfoalkyl ether cyclodextrin, wherein the silymarin composition comprises silymarin or one or more components selected from taxifolin, silychristin A, silydianin, silychristin B, silybin A, silybin B, 2,3-cis-silybin A, 2,3-cis-silybin B, isosilybin A, isosilybin B, or 2,3-cis-isosilybin; and wherein the first component is selected from the group consisting of taxifolin, silychristin A, silydianin, silychristin B, silybin A, silybin B, 2,3-cis-silybin A, 2,3-cis-silybin B, isosilybin A, isosilybin B, and 2,3-cis-isosilybin.

Some embodiments relate to a process of increasing or enhancing the amount of a first component in a silymarin composition, the method comprising combining the silymarin composition and sulfoalkyl ether cyclodextrin, wherein the silymarin composition comprises silymarin or one or more components selected from taxifolin, silychristin A, silydianin, silychristin B, silybin A, silybin B, 2,3-cis-silybin A, 2,3-cis-silybin B, isosilybin A, isosilybin B, or 2,3-cis-isosilybin; and wherein the first component is selected from the group consisting of taxifolin, silychristin A, silydianin, silychristin B, silybin A, silybin B, 2,3-cis-silybin A, 2,3-cis-silybin B, isosilybin A, isosilybin B, and 2,3-cis-isosilybin.

In some embodiments, the method or process described herein further comprises increasing the amount of a second component in the silymarin composition, wherein the second component is selected from the group consisting of taxifolin, silychristin A, silydianin, silychristin B, silybin A, silybin B, 2,3-cis-silybin A, 2,3-cis-silybin B, isosilybin A, isosilybin B, and 2,3-cis-isosilybin, and wherein the first component and the second component are different.

In some embodiments, the method or process described herein further comprises increasing the amount of a third or a fourth component in the silymarin composition, wherein the third or fourth component is selected from the group consisting of taxifolin, silychristin A, silydianin, silychristin B, silybin A, silybin B, 2,3-cis-silybin A, 2,3-cis-silybin B, isosilybin A, isosilybin B, and 2,3-cis-isosilybin, and wherein the first, second, third, and fourth components are different.

Some embodiments relate to a method or process of increasing or enhancing the amount of taxifolin in a silymarin composition, comprising combining the silymarin composition and sulfoalkyl ether cyclodextrin, wherein the composition comprises silymarin or one or more components selected from taxifolin, silychristin A, silydianin, silychristin B, silybin A, silybin B, 2,3-cis-silybin A, 2,3-cis-silybin B, isosilybin A, isosilybin B, and 2,3-cis-isosilybin.

Some embodiments relate to a method or process of increasing or enhancing the amount of silychristin A in a silymarin composition, comprising combining the silymarin composition and sulfoalkyl ether cyclodextrin, wherein the composition comprises silymarin or one or more components selected from taxifolin, silychristin A, silydianin, silychristin B, silybin A, silybin B, 2,3-cis-silybin A, 2,3-cis-silybin B, isosilybin A, isosilybin B, and 2,3-cis-isosilybin.

Some embodiments relate to a method or process of increasing or enhancing the amount of silydianin in a silymarin composition, comprising combining the silymarin composition and sulfoalkyl ether cyclodextrin, wherein the composition comprises silymarin or one or more components selected from taxifolin, silychristin A, silydianin, silychristin B, silybin A, silybin B, 2,3-cis-silybin A, 2,3-cis-silybin B, isosilybin A, isosilybin B, and 2,3-cis-isosilybin.

Some embodiments relate to a method or process of increasing or enhancing the amount of silychristin B in a silymarin composition, comprising combining the silymarin composition and sulfoalkyl ether cyclodextrin, wherein the composition comprises silymarin or one or more components selected from taxifolin, silychristin A, silydianin, silychristin B, silybin A, silybin B, 2,3-cis-silybin A, 2,3-cis-silybin B, isosilybin A, isosilybin B, and 2,3-cis-isosilybin.

Some embodiments relate to a method or process of increasing or enhancing the amount of silybin A in a silymarin composition, comprising combining the silymarin composition and sulfoalkyl ether cyclodextrin, wherein the composition comprises silymarin or one or more components selected from taxifolin, silychristin A, silydianin, silychristin B, silybin A, silybin B, 2,3-cis-silybin A, 2,3-cis-silybin B, isosilybin A, isosilybin B, and 2,3-cis-isosilybin.

Some embodiments relate to a method or process of increasing or enhancing the amount of silybin B in a silymarin composition, comprising combining the silymarin composition and sulfoalkyl ether cyclodextrin, wherein the composition comprises silymarin or one or more components selected from taxifolin, silychristin A, silydianin, silychristin B, silybin A, silybin B, 2,3-cis-silybin A, 2,3-cis-silybin B, isosilybin A, isosilybin B, and 2,3-cis-isosilybin.

Some embodiments relate to a method or process of increasing or enhancing the amount of 2,3-cis-silybin A in a silymarin composition, comprising combining the silymarin composition and sulfoalkyl ether cyclodextrin, wherein the composition comprises silymarin or one or more components selected from taxifolin, silychristin A, silydianin, silychristin B, silybin A, silybin B, 2,3-cis-silybin A, 2,3-cis-silybin B, isosilybin A, isosilybin B, and 2,3-cis-isosilybin.

Some embodiments relate to a method or process of increasing or enhancing the amount of 2,3-cis-silybin B, in a silymarin composition, comprising combining the silymarin composition and sulfoalkyl ether cyclodextrin, wherein the composition comprises silymarin or one or more components selected from taxifolin, silychristin A, silydianin, silychristin B, silybin A, silybin B, 2,3-cis-silybin A, 2,3-cis-silybin B, isosilybin A, isosilybin B, and 2,3-cis-isosilybin.

Some embodiments relate to a method or process of increasing or enhancing the amount of isosilybin A in a silymarin composition, comprising combining the silymarin composition and sulfoalkyl ether cyclodextrin, wherein the composition comprises silymarin or one or more components selected from taxifolin, silychristin A, silydianin, silychristin B, silybin A, silybin B, 2,3-cis-silybin A, 2,3-cis-silybin B, isosilybin A, isosilybin B, and 2,3-cis-isosilybin. A method of increasing or enhancing the amount of isosilybin B in a silymarin composition, comprising combining the silymarin composition and sulfoalkyl ether cyclodextrin, wherein the composition comprises silymarin or one or more components selected from taxifolin, silychristin A, silydianin, silychristin B, silybin A, silybin B, 2,3-cis-silybin A, 2,3-cis-silybin B, isosilybin A, isosilybin B, and 2,3-cis-isosilybin.

In some embodiments, the method or process described above comprises forming a solution of the silymarin composition and sulfoalkyl ether cyclodextrin and removing undissolved components.

Methods of Treatment

The compositions containing silymarin (or components of silymarin) and SAE-CD can be used in cosmetic, pharmaceutical, or nutraceutical applications.

Rosacea Treatment

One use of the disclosed composition relates to a method of reducing appearance of facial redness in rosacea-prone skin, and the method includes administering to a subject in need thereof an effective amount of the composition described herein.

Rosacea develops gradually starting as frequent blushing and frequent irritation of the facial skin. More advanced rosacea is characterized by a vascular stage where patients display increasingly severe erythema (abnormal redness of the skin) and telangiectasia (visible red lines due to abnormal dilatation of capillary vessels and arterioles). Pimple-like eruptions, which may be solid (called papules or nodules) or puss filled (known as pustules) may develop. Such eruptions often look like acne, but closed and open comedones, frequently referred to as whiteheads or blackheads, and commonly present in acne, are not, usually found in rosacea. Later-stage rosacea is characterized by rhinophyma (enlargement of the nose). If left untreated, rosacea can progress to irreversible disfigurement. Rosacea signs and symptoms are often aggravated by sun exposure, changes or extremes in temperature, wind, and consumption of certain foods, such as spicy foods, caffeine, and alcohol.

In some embodiments, the present compositions are administered for at least two weeks on a regular basis to reduce the appearance of the rosacea including the redness ad dryness of the skin. For severe case of rosacea, the present compositions are preferably applied on a regular basis for at least 5 weeks to eliminate the rosacea. After elimination of the rosacea, application of the present topical compositions may continue once a day to maintain the skin as rosacea-free.

Skin Rejuvenation

Another use of the disclosed composition relates to a method of rejuvenating skin, and the method includes administering to a subject in need thereof an effective amount of the composition described herein. The beneficial effects of the silymarin (components of silymarin) in promoting protein synthesis and cell regeneration can be further enhanced by forming a composition with the SAE-CD and be used in increasing the health of skin, improving the appearance of skin, decreasing signs of skin aging, decreasing the presence or appearance of wrinkles, fine lines or age spots or increasing the viability of skin cells.

Cream or lotion compositions and formulations are described herein, for use in the therapeutic renewal and rejuvenation of the skin of a subject, by activating through the use of specific target components which act, alone or in synergistic combination, to increase the generation of stem, epidermal, or other cells in the skin; to activate or increase collagen synthesis in the skin; to activate or increase endogenous hyaluronic acid synthesis in the epidermis; to activate or increase the hydration of the skin, and to activate or increase the stem cell and fibroblast migration within the epidermis to sites of needed repair on the skin. The use of the cosmetic composition cream, lotion, balm, or other dermal application compositions described herein yield progress towards dramatically younger looking skin, rehydration and a decrease in signs of aging such as dryness, thin skin, deep wrinkles and dull appearances.

Skin Aging Prevention

One additional use of the disclosed composition relates to a method of preventing skin aging, and the method includes administering to a subject in need thereof an effective amount of the composition described herein. The composition of silymarin and SAE-CD can provide aged or environmentally-damaged skin with anti-aging benefits.

The term "preventing aging" as used herein refers to any reversal of the physical or functional changes which occur in skin as a result of intrinsic (i.e. natural) aging as caused by the passage of time, or environmentally-induced changes due to sun, weather conditions, or exposure to adverse chemical substances. Examples of benefits include, but are not limited to improvements in the following: fine lines and wrinkles, uneven pigmentation, excessive dryness, excessive roughness, fragility, corneum water holding capacity, microcirculation, elasticity, firmness, epidermal turnover rates, and dermal water content.

Inhibiting Oxidative Stress

The disclosed composition can be used in a method of inhibiting oxidative stress in epidermal and dermal cells, and the method includes administering to a subject in need thereof an effective amount of the composition described herein. In some embodiments, the oxidative stress is induced by UV light, radiation, inflammation, exposure to cigarette smoke, pollution, radiation, or any combination thereof. In some embodiments, the oxidative stress is induced by UV light. The term "oxidative stress" as used herein particular relates to the effect of production of reactive oxygen species, for example to the intracellular increase of ROS. Reactive oxygen species (ROS) are generated in various tissues or cells (intracellular), such as fibroblasts, keratinocytes, melanocytes, cells of the hair follicle and epithelial layers of other non-cutaneous organs. ROS include oxygen ions, free radicals and peroxides both inorganic and organic. They are generally very small molecules and are highly reactive due to the presence of unpaired valence shell electrons. ROSs form as a natural byproduct of the normal metabolism of oxygen and have important roles in cell signaling. However, during times of environmental stress ROS levels can increase dramatically, which can result in significant damage to cell structures. This cumulates into a situation known as oxidative stress. Various types of radiation, like UV radiation, including UVA and UVB, or ionizing radiation, may induce oxidative stress.

Preventing Scar Formation and Accelerating Wound Healing

An additional aspect of the disclosed technology relates to a method of reducing or inhibiting fibronectin production, and the method includes administering to a subject in need thereof an effective amount of the composition described herein.

One aspect of the disclosed technology relates to a method of accelerating wound healing, and the method includes administering to a subject in need thereof an effective amount of the composition described herein.

In wound healing, TGF-β is a potent activator of extracellular matrix gene expression and stimulates collagen and fibronectin synthesis by dermal fibroblasts and Silymarin has been shown to reduce TGF. Despite the necessity for fibronectin production in wound healing, overproduction of fibronectin is associated with hypertrophic scars (HS) as such inhibition of fibronectin production has been suggested to have therapeutic potential in the treatment of excessive scars and other fibroproliferative diseases. Wound healing occurs in sequential periods including hemostasis, inflammation, proliferation, and remodeling. Wound healing is a dynamic and closely interactive process of various factors including procollagen and fibronectin. The composition described herein can accelerate the wound healing process by modulating the inflammation response.

One aspect of the disclosed technology relates to a method of reducing or inhibiting the appearance of scar, and the method includes administering to a subject in need thereof an effective amount of the composition described herein. In some embodiments, the scar is a hypertrophic scar or post-burn scar.

Scar formation such as hypertrophic scar and post-burn scar, may be related to excessive or persistent production of fibronectin. Therefore, the modulation of fibronectin production by the composition described herein can help to reduce or inhibit the scar formation.

Treatment of Skin Inflammation

One aspect of the disclosed technology relates to a method of treating or inhibiting progression a skin inflammation condition, and the method includes administering to a subject in need thereof an effective amount of the composition described herein. In some embodiments, the composition described herein can reduce or inhibit a production of interleukin 6 (IL-6). In some embodiments, the composition described herein can reduce or inhibit the production of interferon gamma-induced protein 10 (IP-10). In some embodiments, the composition described herein can reduce or inhibit a production of interleukin-8 (IL-8).

Skin inflammation condition can cover a broad category that includes many conditions ranging in severity, from mild itching to grave medical health complications. Skin inflammation conditions can be common in people of all ages and races. Such conditions can be characterized by irritation and inflammation of the skin. Skin inflammation condition can include any conditions known by those skilled in the art. Examples of skin inflammation condition include but are not limited to acne, dermatitis/eczema, psoriasis, sebaceous cysts, diaper rash. In some embodiments, the skin inflammation condition is psoriasis.

Anti-Oxidant Properties

One aspect of the disclosed technology relates to a method of protecting skin from oxidation, and the method includes administering to a subject in need thereof an effective amount of the composition described herein. In some embodiments, the composition described herein can reduce a concentration of reactive nitrogen species. In some embodiments, the composition described herein can reduce a concentration of reactive oxygen species.

One aspect of the disclosed technology relates to a method of delivering anti-oxidant to skin, and the method includes administering to a subject in need thereof an effective amount of the composition described herein. In some embodiments, the anti-oxidant includes silymarin. [0183] Antioxidants can help slow or prevent the oxidation of other molecules. Antioxidants function in three ways: primary antioxidants, or electron donors; secondary antioxidants, which chelate metal ions; and co-antioxidants, which facilitate other antioxidants. Many anti-oxidants including silymarin offer multiple protective benefits. The use of topical cosmeceuticals containing antioxidants increases protection and limits damage.

Skin Cancer Treatment

The compositions described herein can also be used in a method of reducing the likelihood of skin cancer occurring in a subject, and the method includes administering to a subject in need thereof an effective amount of the composition described herein.

Silymarin and components of silymarin are strong antioxidants capable of scavenging both free radicals and reactive oxygen species (ROS), thus increasing the antioxidant potential of cells by ameliorating the deleterious effects of free radical reactions. Additionally, since an increase in ornithine decarboxylase (ODC) activity in epidermis is a prerequisite for skin tumor promotion, it has been shown that silymarin possesses strong inhibitory effects against the induction of epidermal ODC and messenger RNA expression in mouse models, caused by 12-O-tetradecanoylphorbol-13-acetate (TPA). Further, silymarin has been shown to afford substantial protection against photocarcinogenesis in a mouse model. This effect of silymarin is due to the inhibition of several different events associated with UNB-induced tumor initiations and tumor promotion, by virtue of its strong anti-oxidant activity. Therefore, a composition containing silymarin and SAE-CD can be effective for preventing skin cancer, either through topical or oral administration.

Liver Damage Treatment

Another use of the compositions described herein relates to a method of treating or reducing liver damage from toxin, and the method includes administering to a subject in need thereof an effective amount of the composition described herein.

A method of reducing or inhibiting hepatic collagen accumulation in liver, comprising and the method includes administering to a subject in need thereof an effective amount of the composition described herein.

A method of reducing or inhibiting liver fibrosis, and the method includes administering to a subject in need thereof an effective amount of the composition described herein Liver has a high risk of being exposed to numerous toxic substances as well as nutrients since the exogenous materials taken up by the body initially enter the liver to be filtered. Thus, liver is highly vulnerable to damage relative to other organs. Liver diseases are classified into two major types according to cause: one is toxic liver disease caused by the excessive ingestion of alcohol or the like, and the other is viral liver disease caused by viral infection. Viral liver diseases arise from infection with hepatitis B virus, hepatitis C virus, or the like. Recently, toxic liver disease is increasing due to food, medicaments, medicinal herbal substances, alcohol, and the like.

Silymarin and components of silymarin have been found to stabilize the membranes of liver cells as to block the inflow of harmful substances and up-regulate protein synthesis in the liver to promote liver regeneration. Studies have suggested an inhibition of the expression of inflammatory factors in the liver protection by silymarin wherein the inhibition is mediated through downregulation of Kupper cells, a macrophage found inside liver tissues (Dehmlow, C. et al., Hepatology 23(4):749~754, 1996), which is incorporated herein by reference in its entirety. Therefore, a containing silymarin and SAE-CD can be effective for treating or reducing liver damage from toxin, either through topical or oral administration.

Additionally, the compositions described herein can be used in a method of treating a liver disease, and the method includes administering to a subject in need thereof an effective amount of the composition described herein. In some embodiments, the liver disease is alcoholic fatty liver disease, non-alcoholic fatty liver disease, non-alcoholic steatohepatitis, liver fibrosis, cirrhosis, primary biliary cirrhosis, hepatic ischemia reperfusion injury, viral hepatitis B, viral hepatitis C, or alcoholic hepatitis.

The administration method can vary depending on the use of the composition. In some embodiments, the administration is oral administration. In some embodiments, the administration is topical administration. In some embodiments, the method of administering includes topically administering composition described above. In some embodiments, the method of administering, comprising topically administering composition described above.

The following examples will further describe the compositions described herein, and are used for the purposes of illustration only, and should not be considered as limiting.

EXAMPLES

Example 1

Silymarin Solubility with CAPTISOL®

CAPTISOL® was dissolved in water to form four solutions with a CAPTISOL® concentration of 0.05 mol/L, 0.1 mol/L, 0.2 mol/L, and 0.3 mol/L respectively. 12 mg of silymarin powder (Sigma Aldrich) was added to 1 mL of each of the four CAPTISOL® solutions on Day 1, another 12 mg Silymarin powder was added on Day 3, and 19-22 mg Silymarin powder was added on Day 7 to ensure that silymarin reached its maximum solubility in each solution. The solutions were stirred in a water bath at 25° C. The solutions were then centrifuged prior to sampling. The supernatant was diluted in MeOH in preparation for HPLC assay.

A reference standard was prepared by mixing silymarin with methanol to provide a methanol solution with a silymarin concentration of 0.1 mg/ml.

HPLC was used to measure the relative concentrations of the different components of silymarin in each sample solution following the method described in Kuki et al., (2012) Chromatogram 75:175-180. The relative concentration of each component of silymarin was measured by comparing the normalized peak area units with that of the standard reference measured by the UV data at 288 nm and assuming equivalent extinction coefficients for all components.

Figure 15:
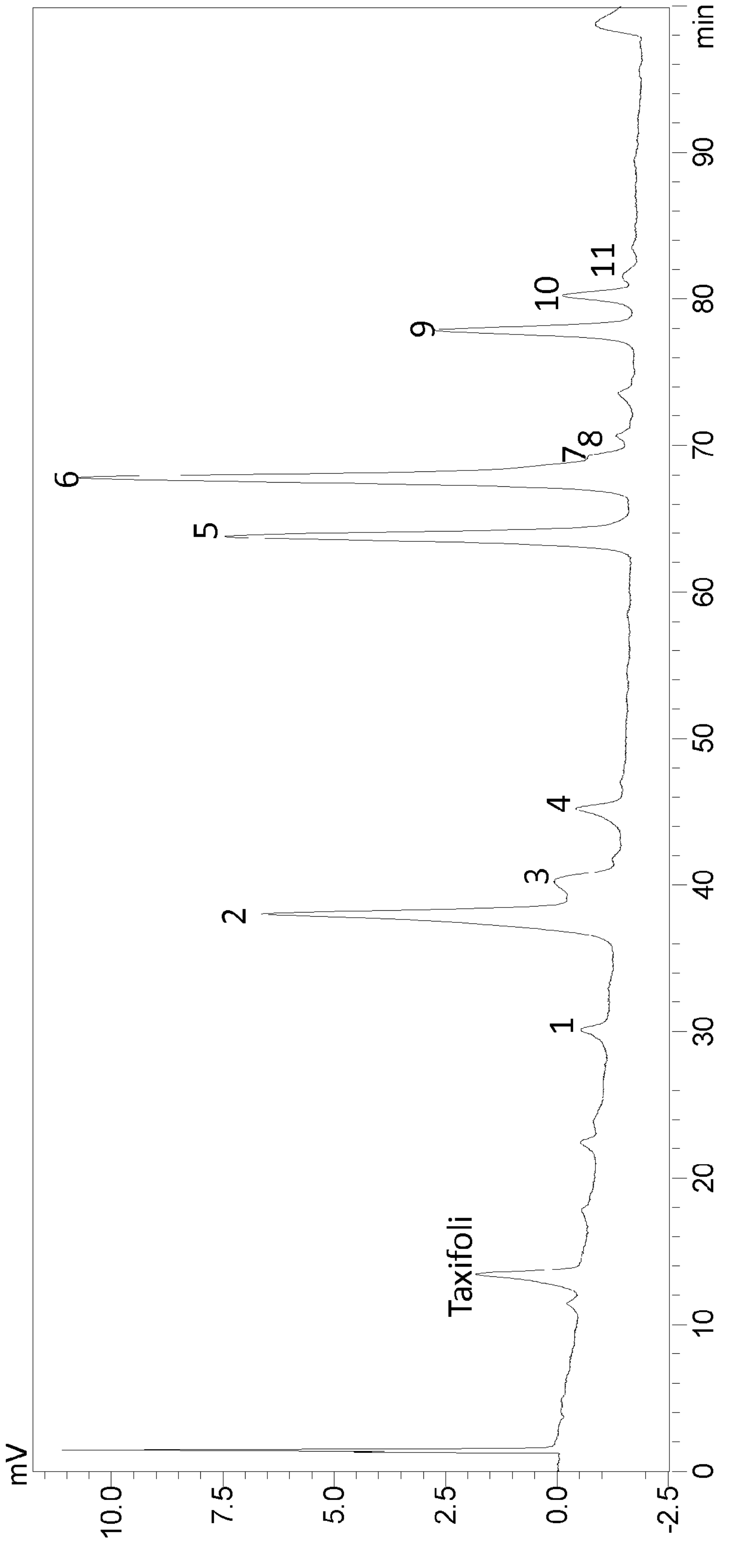
FIG. 15 shows the HPLC chromatogram of the various constituents of silymarin.

Identification of various constituents of silymarin as described herein was made by reference to the HPLC chromatogram shown in Kuki et al., (2012) Chromatogram 75:175-180. FIG. 15 shows the HPLC/UV chromatogram of the various constituents of the silymarin extract. The eluate having a retention time of about 14.7 min corresponds to taxifolin, the eluate at peak 2 having a retention time of about 37.31 min corresponds to silycrhistin A, the eluate at peak 3 having a retention time of about 40.22 min corresponds to silydanin, the eluate at peak 4 having a retention time of about 43.84 min corresponds to silychristin B, the eluate at peak 5 having a retention time of about 63.70 min corresponds to silybin A, the eluate at peak 6 having a retention time of about 67.40 min corresponds to silybin B, the eluate at peak 7 having a retention time of about 68.06 min possibly corresponds to 2,3-cis-silybin A, the eluate at peak 8 having a retention time of about 68.65 min possibly corresponds to 2,3-cis-silybin B, the eluate at peak 9 having a retention time of about 77.91 min corresponds to isosilybin A, the eluate at peak 10 having a retention time of about 80.25 min corresponds to isosilybin B; and the eluate at peak 11 having a elution time of about 81.51 min possibly corresponds to 2,3-cis-isosilybinisomer A or B (isosilybin isomer).

Table 1a shows the normalized HLPC peak areas and retention time (RT) of various components of silymarin in the methanol (0.1 mg/ml) reference, water only solution, and 0.05M CAPTISOL® water solution. Table 1b shows the normalized peak areas (indicative of relative concentration) and retention time (RT) of various components of silymarin in 0.1M CAPTISOL® water solution, 0.2M CAPTISOL® water solution, and 0.3M CAPTISOL® water solution under the same HPLC measurement conditions as those samples listed in Table 1a. Ten components of silymarin are listed, including Silychristin A, Silydianin, Silychristin B, Silybin A, Silybin B, 2,3-cis-silybin A, 2,3-cis-silybin B, Isosilybin A, Isosilybin B, and 2,3-cis-isosilybin isomer. The normalized peak areas listed for $H_2O$, 0.05 M CAPTISOL®, 0.1 M CAPTISOL®, 0.2 CAPTISOL®, and 0.3 CAPTISOL® are the average peak areas measured from two samples of each type of solution. As shown in Tables 1a and 1b, for the sample where the silymarin was dissolved only in water without CAPTISOL®, the total of the normalized peak areas are smaller than the samples wherein the silymarin was dissolved in water with CAPTISOL®, indicating a higher concentration (and hence solubility) in the CAPTISOL® samples. For samples with CAPTISOL®, the total of the normalized peak areas increase as the concentration of CAPTISOL® increases in the samples, indicating that solubility of silymarin also increases.

TABLE 1a

Normalized peak area of various components of silymarin in standard reference, water, and 0.05M CAPTISOL ®

| Components | Retention time | MeOH standard (0.1 mg/ml) | $H_2O$ | CAPTISOL ® 0.05M |
|---|---|---|---|---|
| Silychristin A | 38 | 935568 | 19224798 | 401872862.5 |
| Silydianin | 40.1 | 114318 | 3100092.5 | 26458700 |
| Silychristin B | 45.2 | 62791 | 1531907.5 | 38908312.5 |
| Silybin A | 63.8 | 1064703 | 925932.5 | 93437687.5 |
| Silybin B | 67.7 | 1343653 | 2268945 | 234922837.5 |
| 2,3-cis-silybin A | 69.1 | 51986 | 177117.5 | 15388762.5 |
| 2,3-cis-silybin B | 70.6 | 30393 | 61772.5 | 5780750 |
| Isosilybin A | 77.8 | 442127 | 1526917.5 | 117727325 |
| Isosilybin B | 80.2 | 132664 | 447682.5 | 37674712.5 |
| 2,3-cis-isosilybin isomer | 81.5 | 21019 | 121460 | 6281612.5 |
| Total | | 4199222 | 29386625 | 978453562.5 |

TABLE 1b

| Normalized peak area of various flavonolignan components of silymarin in 0.1M CAPTISOL ®, 0.2M CAPTISOL ®, and 0.3M CAPTISOL ® | | | |
|---|---|---|---|
| Components | CAPTISOL ® 0.1M | CAPTISOL ® 0.2M | CAPTISOL ® 0.3M |
| Silychristin A | 642151950 | 1069088200 | 1129854350 |
| Silydianin | 55230500 | 127256650 | 147989500 |
| Silychristin B | 48315700 | 97543950 | 104807350 |
| Silybin A | 159488700 | 267520300 | 307815350 |
| Silybin B | 374904700 | 579992500 | 661382400 |
| 2,3-cis-silybin A | 18540350 | 41995100 | 38027300 |
| 2,3-cis-silybin B | 7237250 | 25609950 | 26827550 |
| Isosilybin A | 231633300 | 422609150 | 441872850 |
| Isosilybin B | 69164250 | 124076150 | 130295850 |
| 2,3-cis-isosilybin isomer | 10679500 | 19413900 | 22244200 |
| Total | 1617346200 | 2775105850 | 3011116700 |

The relative molar amounts of the ten flavonolignan components of silymarin were calculated by dividing the normalized peak area of each component in a sample by the total normalized peak area of the sample. Table 2 lists the relative amounts of the ten flavonolignan components of silymarin in the methanol (0.1 mg/ml) reference, and upon saturated solublity in water only solution, 0.05M CAPTISOL® water solution, 0.1M CAPTISOL® water solution, 0.2M CAPTISOL® water solution, and 0.3M CAPTISOL® water solution. The data shown in Table 2 is depicted in the bar chart of FIG. 1 As shown in Table 2 and FIG. 1, the relative amounts of some components increase in the presence of CAPTISOL® whereas others decrease. For example, the presence of CAPTISOL® results in enrichment of the relative amounts of Silybin A and Silybin B and a decrease in the relative amount of Silychristin A.

TABLE 2

| Percentages of Various Flavonolignan Components of Silymarin in the samples | | | | | | |
|---|---|---|---|---|---|---|
| | MeOH standard (0.1 mg/ml) (%) | $H_2O$ (%) | CAPTISOL ® (0.05M) (%) | CAPTISOL ® (0.1M) (%) | CAPTISOL ® (0.2M) (%) | CAPTISOL ® (0.3M) (%) |
| Silychristin A | 22.28 | 65.42 | 41.07 | 39.70 | 38.52 | 37.52 |
| Silydianin | 2.72 | 10.55 | 2.70 | 3.41 | 4.59 | 4.91 |
| Silychristin B | 1.50 | 5.21 | 3.98 | 2.99 | 3.51 | 3.48 |
| Silybin A | 25.35 | 3.15 | 9.55 | 9.86 | 9.64 | 10.22 |
| Silybin B | 32.00 | 7.72 | 24.01 | 23.18 | 20.90 | 21.96 |
| 2,3-cis-silybin A | 1.24 | 0.60 | 1.57 | 1.15 | 1.51 | 1.26 |
| 2,3-cis-silybin B | 0.72 | 0.21 | 0.59 | 0.45 | 0.92 | 0.89 |
| Isosilybin A | 10.53 | 5.20 | 12.03 | 14.32 | 15.23 | 14.67 |
| Isosilybin B | 3.16 | 1.52 | 3.85 | 4.28 | 4.47 | 4.33 |
| 2,3-cis-isosilybin isomer | 0.50 | 0.41 | 0.64 | 0.66 | 0.70 | 0.74 |
| Total | 100 | 100 | 100 | 100 | 100 | 100 |

As shown in Table 2, the presence of CAPTISOL® in the samples helped to selectively enrich the percentages of some flavonolignan components of silymarin. For example, the percentage of silybin A in water only sample (about 3.15%) is lower than the percentages of silybin A in the four samples with CAPTISOL® added (over 9.5% for all four samples with CAPTISOL® added); the percentage of silybin B in water only sample (about 7.72%) is lower than the percentages of silybin A in the four samples with CAPTISOL® added (over 20% for all four samples with CAPTISOL® added); the percentage of isosilybin A in water only sample (about 5.20%) is lower than the percentages of isosilybin A in the four samples with CAPTISOL® added (over 12% for all four samples with CAPTISOL® added); and the percentage of isosilybin B in water only sample (about 1.52%) is lower than the percentages of isosilybin B in the four samples with CAPTISOL® added (over 3.8% for all four samples with CAPTISOL® added). The increased percentages of silybin A, silybin B, isosilybin A, and isosilybin B in the samples with CAPTISOL® added show that CAPTISOL® helps to enrich these components of flavonolignan in the compositions.

The presence of CAPTISOL® also helped to selectively decrease the percentages of some components of silymarin in the compositions. For example, the percentage of Silychristin A in water only sample (about 65.42%) is higher than the percentages of Silychristin A in the four samples with CAPTISOL® added (between about 37% to about 42% for all four samples with CAPTISOL® added); and the percentage of Silydianin in water only sample (about 10.55%) is higher than the percentages of Silydianin in the four samples with CAPTISOL® added (between about 2.5% to about 5% for all four samples with CAPTISOL® added). The reduced percentages of Silychristin A and Silydianin in the samples with CAPTISOL® added show that CAPTISOL® helps to reduce the percentages of these components of all flavonolignan components.

Figure 2:
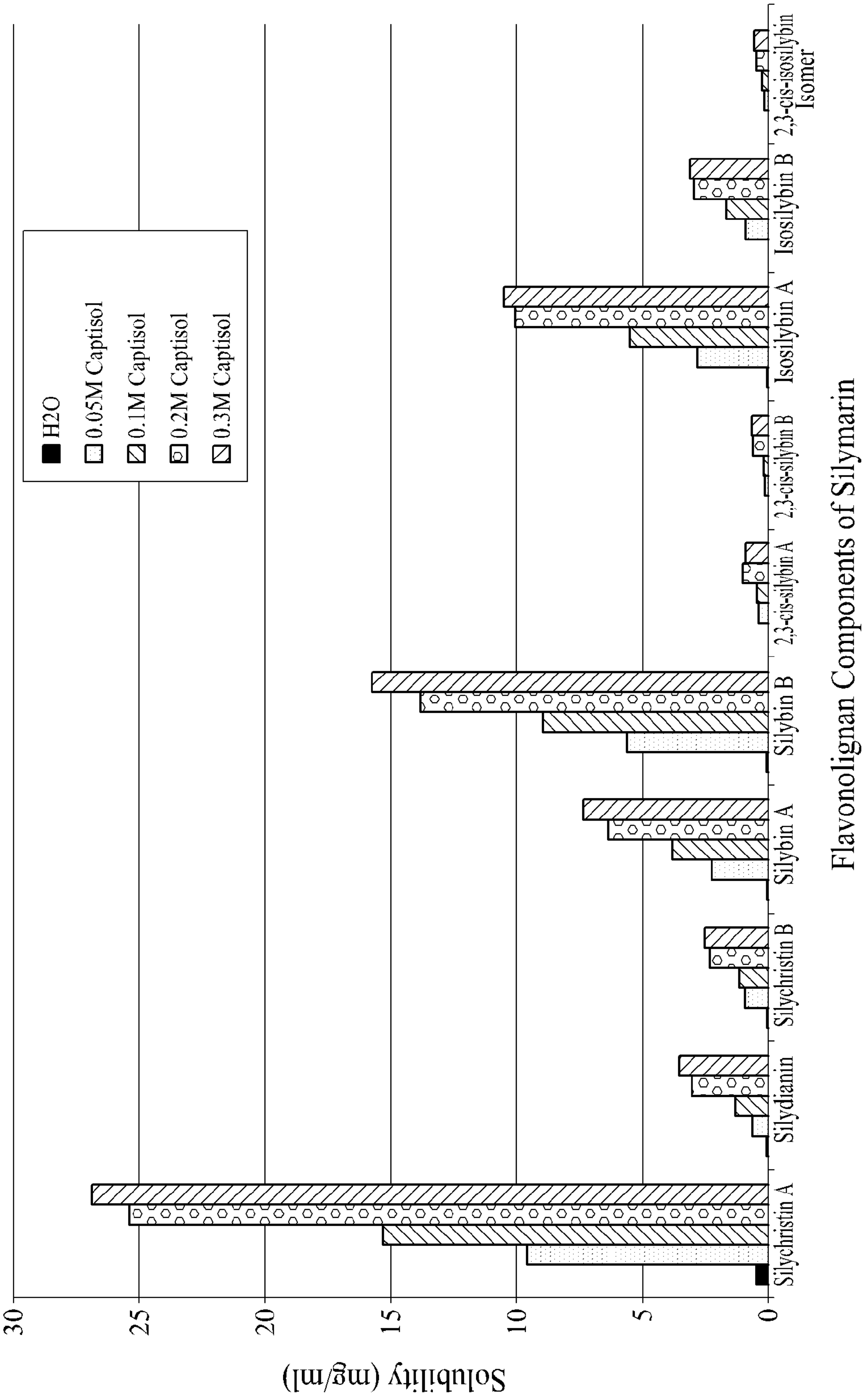
FIG. 2. shows the mutual solubility of various components of silymarin attained upon saturating with excess silymarin in water and 0.05M, 0.1M, 0.2M, and 0.3M solutions of sulfobutylether-β-cyclodextrin.
Figure 3:
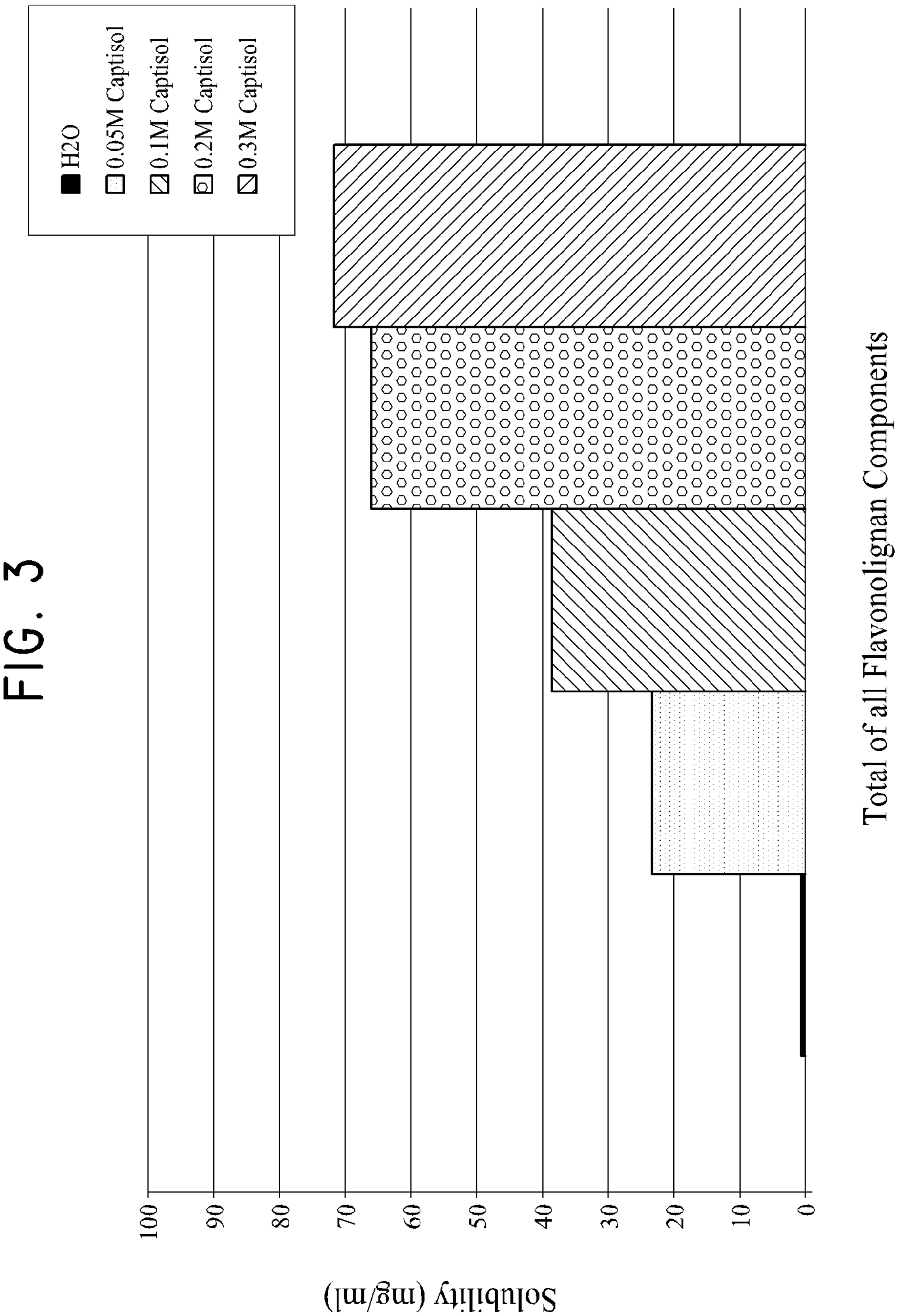
FIG. 3 shows the mutual saturated solubility of the total amount of all flavonolignan components of silymarin in water and 0.05M, 0.1M, 0.2M, and 0.3M solutions of sulfobutylether-β-cyclodextrin.

Table 3 shows the solubility of the various components of silymarin and the total solubility of silymarin in the methanol standard (0.1 mg/ml), and the total solubility of silymarin attained upon saturating with excess silymarin water, 0.05M CAPTISOL®, 0.1M CAPTISOL®, 0.2M CAPTISOL®, and 0.3M CAPTISOL® samples. FIG. 2 plots this data for water, 0.05M CAPTISOL®, 0.1M CAPTISOL®, 0.2M CAPTISOL®, and 0.3M CAPTISOL® and FIG. 3 shows the total solubility of all flavonolignan components upon saturating with excess silymarin in water, 0.05M CAPTISOL®, 0.1M CAPTISOL®, 0.2M CAPTISOL®, and 0.3M CAPTISOL®. The concentration of each flavonolignan component of silymarin was calculated from the peak areas in Tables 1a and 1b and the total concentration of silymarin (0.1 mg/ml) in the reference sample, assuming constant extinction coefficients for each component.

TABLE 3

Solubility (mg/ml) of various flavonolignan components of silymarin in the samples

| | MeOH standard (0.1 mg/ml) | $H_2O$ | CAPTISOL ® (0.05M) | CAPTISOL ® (0.1M) | CAPTISOL ® (0.2M) | CAPTISOL ® (0.3M) |
|---|---|---|---|---|---|---|
| Silychristin A | 0.022 | 0.46 | 9.57 | 15.29 | 25.46 | 26.91 |
| Silydianin | 0.003 | 0.07 | 0.63 | 1.32 | 3.03 | 3.52 |
| Silychristin B | 0.001 | 0.04 | 0.93 | 1.15 | 2.32 | 2.50 |
| Silybin A | 0.025 | 0.02 | 2.23 | 3.80 | 6.37 | 7.33 |
| Silybin B | 0.032 | 0.05 | 5.59 | 8.93 | 13.81 | 15.75 |
| 2,3-cis-silybin A | 0.001 | 0.00 | 0.37 | 0.44 | 1.00 | 0.91 |
| 2,3-cis-silybin B | 0.001 | 0.00 | 0.14 | 0.17 | 0.61 | 0.64 |
| Isosilybin A | 0.011 | 0.04 | 2.80 | 5.52 | 10.06 | 10.52 |
| Isosilybin B | 0.003 | 0.01 | 0.90 | 1.65 | 2.95 | 3.10 |
| 2,3-cis-isosilybin isomer | 0.001 | 0.00 | 0.15 | 0.25 | 0.46 | 0.53 |
| Total | 0.100 | 0.70 | 23.30 | 38.52 | 66.09 | 71.71 |

Example 2

Silymarin Solubility in Water, CAPTISOL Solution and γ-Cyclodextrin Solution The solubility of Silymarin was measured in water, in water with 0.15 mol/L of γ-Cyclodextrin (Cavamax), and in water with 0.2M of CAPTISOL® according to the same procedures described in Example 1. The solutions were centrifuged for 10 min at 13K rpm. An aliquot of the supernatant was diluted 1:5 for Water, 1:25 for γ-Cyclodextrin and 1:100 for both 0.20 M CAPTISOL® and 0.20M HP-B-Cyclodextrin using MeOH as the diluent. The standard reference was prepared by dissolving silymarin in 10 mg/mL of DMSO and then diluted to 0.50 mg/mL using MeOH.

Table 4 shows the normalized HPLC peak areas of various components of silymarin in the methanol (0.5 mg/ml) reference, in water alone, in 0.15M of γ-Cyclodextrin (Cavamax), and in 0.2M CAPTISOL®. The normalized peak areas listed for $H_2O$, 0.15 M of γ-Cyclodextrin (Cavamax), and in 0.2M CAPTISOL® are the average peak areas measured from two samples of each solution. As shown in Table 4, for the sample where the silymarin was dissolved in water without CAPTISOL®, the total of the normalized peak areas is smaller than the samples where the silymarin was dissolved in water with some CAPTISOL® or γ-Cyclodextrin added. In addition, the total of the normalized peak areas for the CAPTISOL® sample is much higher than that of the γ-Cyclodextrin sample.

TABLE 4

Normalized peak area of various components of silymarin in the standard reference, water, 0.15 mole/L of γ-Cyclodextrin (Cavamax) and 0.2M CAPTISOL ®.

| Components | RT | MeOH standard (0.5 mg/ml) | $H_2O$ Average | 0.15M γ-cyclodextrin (Cavamax) Avg. X dil. | 0.2M CAPTISOL ® Avg. X dil. |
|---|---|---|---|---|---|
| Silychristin A | 38 | 2708432 | 10156055 | 117920313 | 530583950 |
| Silydianin | 40.1 | 666560 | 2792773 | 23563088 | 98936750 |
| Silychristin B | 45.2 | 346692 | 1273073 | 12740400 | 71320000 |
| Silybin A | 63.8 | 2378750 | 645292.5 | 5149812.5 | 141684850 |
| Silybin B | 67.7 | 3575975 | 646835 | 1717337.5 | 257833100 |
| 2,3-cis-silybin A | 69.1 | 176809 | 325630 | 2677862.5 | 50826850 |
| 2,3-cis-silybin B | 70.6 | 114422 | 130157.5 | 1275425 | 27642100 |
| Isosilybin A | 77.8 | 1061908 | 957357.5 | 4757112.5 | 196958850 |
| Isosilybin B | 80.2 | 390647 | 292765 | 838437.5 | 71506550 |
| 2,3-cis-isosilybin isomer | 81.5 | 91293 | 77512.5 | 612600 | 16568000 |
| Total | | 11511488 | 17297450 | 171252388 | 1463861000 |

The relative molar amounts of the ten components of silymarin in methanol standard (0.5 mg/ml), water, 0.15 M CAPTISOL® and 0.20 M γ-cyclodextrin samples were calculated by dividing the normalized peak area of each component in the sample by the total normalized peak area of the entire sample. The calculated percentages are listed in Table 5 and plotted in FIG. 4. The change of the saturated solubility of the various components of silymarin in each of the four types of samples can be seen in FIG. 4.

Figure 4:
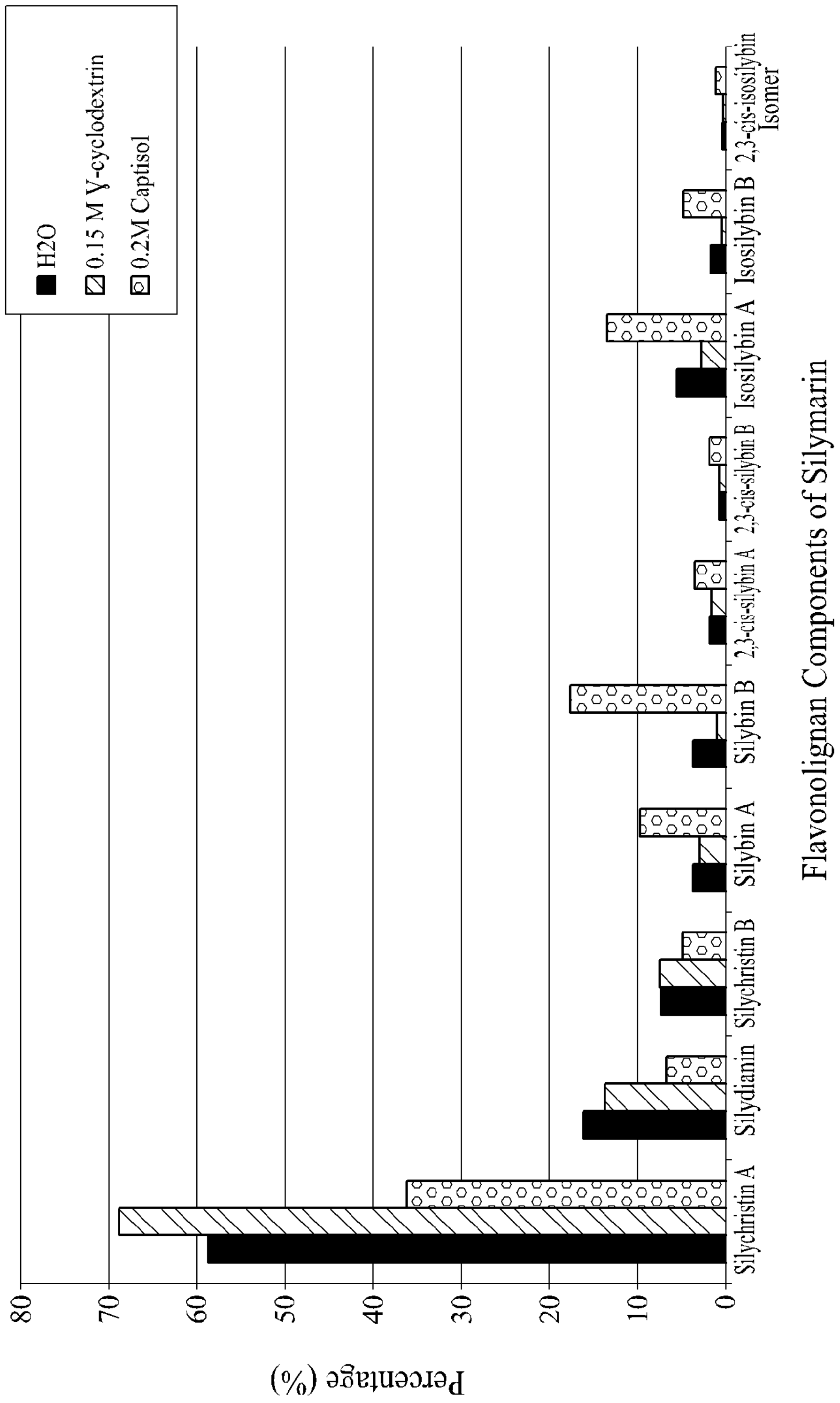
FIG. 4 shows percentages of various flavonolignan components of silymarin dissolved in water, 0.15M sulfobutylether-β-cyclodextrin and 0.20 M γ-cyclodextrin samples upon saturating with excess silymarin.

As shown in Table 5 and FIG. 4, the presence of CAPTISOL® in the samples helped to increase the percentages of some components of silymarin in the composition in comparison to the water only sample and the sample with γ-cyclodextrin added. For example, the percentage of silybin A in water only sample is about 3.73%, which is about the same as the percentage of 3.01% in the sample with γ-cyclodextrin added, and the percentage of silybin A in the sample with CAPTISOL® added is about 9.68%; the percentage of silybin B is about 3.34% in the water only sample and about 1% in the sample with γ-cyclodextrin added, and the percentage of silybin A in the sample with CAPTISOL® added is about 17.61%; the percentage of isosilybin A is about 5.53% in the water only sample and about 2.78% in the sample with γ-cyclodextrin added, and the percentage of silybin A in the sample with CAPTISOL® added is about 13.45%; the percentage of isosilybin B is about 1.69% in the water only sample and about 0.49% in the sample with γ-cyclodextrin added, and the percentage of silybin A in the sample with CAPTISOL® added is about 4.88%. Therefore, the increased percentages of silybin A, silybin B, isosilybin A, and isosilybin B in the samples with CAPTISOL® added show that adding CAPTISOL® helps to enrich these components of silymarin in the compositions, while adding other types of cyclodextrin such as γ-cyclodextrin may lead to the percentages of these components being reduced or maintained at about the same level in comparison as the water only sample.

Adding CAPTISOL® also helped to decrease the percentages of some components of silymarin in the compositions. For example, the percentage of silychristin A is about 58.71% in the water only sample and about 68.86% in the sample with γ-cyclodextrin added, but the percentages of silychristin A in the sample with CAPTISOL® added is about 36.25%; the percentage of silydianin is about 16.15% in the water only sample and about 13.76% in the sample with γ-cyclodextrin added, but the percentages of silydianin in the sample with CAPTISOL® added is about 6.76%. The reduced percentages of silychristin A and silydianin in the sample with CAPTISOL® added show that CAPTISOL® helps to reduce the percentages of these components of silymarin in the compositions, while adding other types of cyclodextrin such as γ-cyclodextrin may lead to the percentages of these components being increased or maintained at about the same level as the water only sample.

TABLE 5

Percentages of various components of silymarin flavonolignan in the samples

| | MeOH standard (0.5 mg/ml) (%) | $H_2O$ (%) | γ-cyclo-dextrin (0.15M) (%) | CAPTISOL ® (0.2M) (%) |
|---|---|---|---|---|
| Silychristin A | 23.53 | 58.71 | 68.86 | 36.25 |
| Silydianin | 5.79 | 16.15 | 13.76 | 6.76 |
| Silychristin B | 3.01 | 7.36 | 7.44 | 4.87 |
| Silybin A | 20.66 | 3.73 | 3.01 | 9.68 |
| Silybin B | 31.06 | 3.74 | 1.00 | 17.61 |
| 2,3-cis-silybin A | 1.54 | 1.88 | 1.56 | 3.47 |
| 2,3-cis-silybin B | 0.99 | 0.75 | 0.74 | 1.89 |
| Isosilybin A | 9.22 | 5.53 | 2.78 | 13.45 |
| Isosilybin B | 3.39 | 1.69 | 0.49 | 4.88 |
| 2,3-cis-isosilybin isomer | 0.79 | 0.45 | 0.36 | 1.13 |
| Total | 100.00 | 100.00 | 100.00 | 100.00 |

Figure 5:
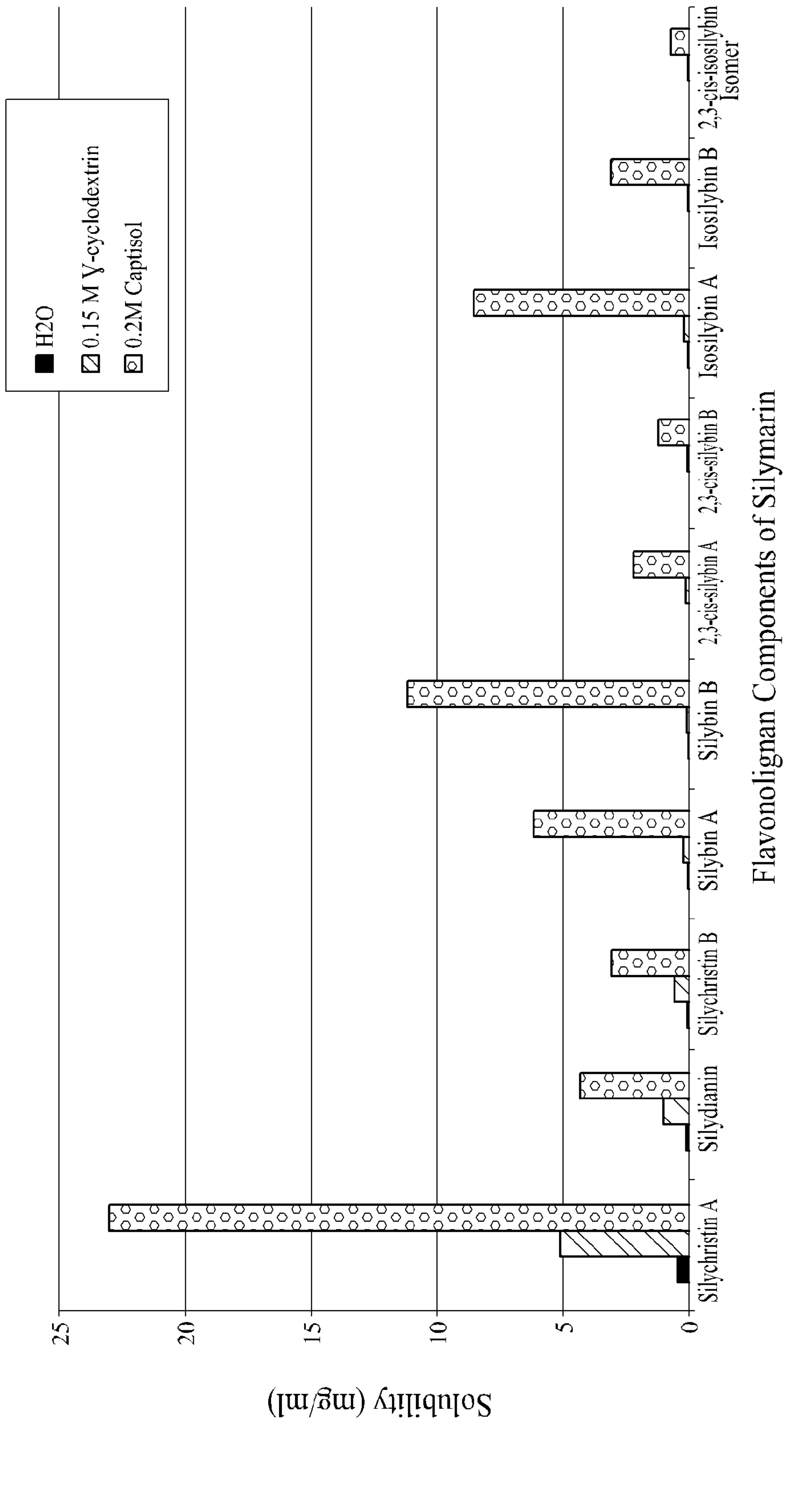
FIG. 5 shows the saturated solubility of various flavonolignan components of silymarin in water, 0.15 M sulfobutylether-β-cyclodextrin and 0.20 M γ-cyclodextrin samples.
Figure 6:
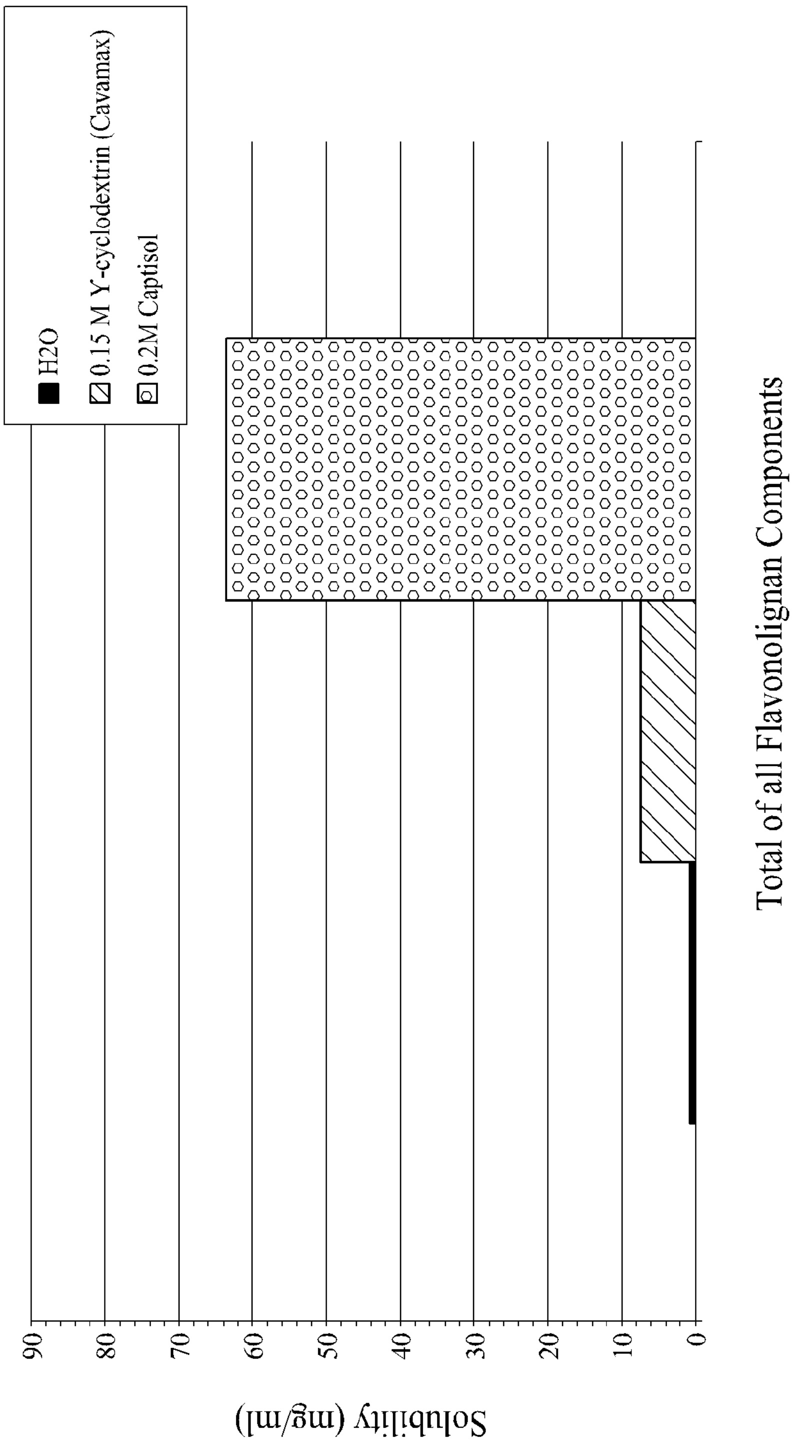
FIG. 6 shows the mutual saturated solubility of the total amount of all flavonolignan components in water, 0.15 M sulfobutylether-β-cyclodextrin and 0.20 M γ-cyclodextrin samples.

Table 6 shows the solubility of the various flavonolignan components of silymarin and the total solubility of flavonolignan in methanol standard (0.5 mg/ml), water, 0.15 M CAPTISOL® and 0.20 M γ-cyclodextrin. The data shown in Table 6 is plotted in FIGS. 5 and 6. The change of the solubility of the various components of silymarin in each of the three samples can be seen in FIG. 5. The total mutual saturated solubility of all flavonolignan components can be seen in FIG. 6. The concentration of each component of silymarin was calculated from the peak areas in Table 4 and the total concentration of silymarin (0.5 mg/ml) in the reference sample, assuming constant extinction coefficients for each component. As shown Table 6 and FIG. 5, the saturated solubility of silymarin in the water only sample is much lower than the samples with γ-cyclodextrin (0.15M) added; and for the samples with γ-cyclodextrin present, the solubility of silymarin is much lower than that of the CAPTISOL® (0.2 M) sample. The various components of silymarin also have increased solubility in the CAPTISOL® (0.2M) sample.

TABLE 6

Solubility (mg/ml) of various components of silymarin in the samples

| | MeOH standard (0.5 mg/ml) | $H_2O$ | γ-cyclo-dextrin (0.15M) | CAPTISOL ® (0.2M) |
|---|---|---|---|---|
| Silychristin A | 0.12 | 0.44 | 5.12 | 23.05 |
| Silydianin | 0.03 | 0.12 | 1.02 | 4.30 |
| Silychristin B | 0.02 | 0.06 | 0.55 | 3.10 |
| Silybin A | 0.10 | 0.03 | 0.22 | 6.15 |
| Silybin B | 0.16 | 0.03 | 0.07 | 11.20 |
| 2,3-cis-silybin A | 0.01 | 0.01 | 0.12 | 2.21 |
| 2,3-cis-silybin B | 0.00 | 0.01 | 0.06 | 1.20 |
| Isosilybin A | 0.05 | 0.04 | 0.21 | 8.55 |
| Isosilybin B | 0.02 | 0.01 | 0.04 | 3.11 |
| 2,3-cis-isosilybin isomer | 0.00 | 0.00 | 0.03 | 0.72 |
| Total | 0.50 | 0.75 | 7.44 | 63.58 |

Example 3

Silymarin Solubility Study

The silymarin reference standard was prepared by dissolving 20.04 mg of silymarin 80% (Indena, Milano, Italy) in 1.00 ml of DMSO and then diluting it to 1.002 mg/ml with 40% methanol to be used in a HPLC analysis. The constituents of silymarin were quantified using the HPLC in accordance with the procedures described in Example 1 and the results are shown in Table 7a below.

TABLE 7a

Components of silymarin in 1.002 mg/ml silymarin standard

| Named Peak | Ret. Time (min) | Peak Area | Area % |
|---|---|---|---|
| Taxifolin | 13.24 | 1567093 | 5.5 |
| Silychristin A | 37.43 | 5467742 | 19.1 |
| Silydianin | 39.8 | 4947374 | 17.2 |
| Silychristin B | 44.62 | 615338 | 2.1 |
| Silybin A | 63.26 | 4532137 | 15.8 |
| Silybin B | 67.25 | 6916522 | 24.1 |
| 2,3-cis-silybin A | 68.78 | 375367 | 1.3 |
| 2,3-cis-silybin B | 70.13 | 117679 | 0.4 |
| Isosilybin A | 77.4 | 2702655 | 9.4 |
| Isosilybin B | 79.79 | 1238023 | 4.3 |
| 2,3-cis-isosilybin isomer | 81.28 | 211124 | 0.7 |
| Total | n/a | 28691054 | 100 |

The peak area % of taxifolin is about 5.5% based on the total peak areas of taxifolin and the ten flavonolignan components of silymarin. The combined peak area of the ten flavonolignan components is about 94.5% of the total peak areas of taxifolin and the ten flavonolignan components of silymarin.

Samples A1 to A5 were prepared either in deionized water or CAPTISOL® solution. The silymarin-water samples were prepared by adding 3.0 ml of deionized water or 3.0 ml of CAPTISOL® solution (0.05 M, 0.10 M, or 0.20 M) to 260 mg silymarin 80% in 5 ml Eppendorf tubes, and the tubes were capped securely and placed in end-over-end mixer for about 6 days at room temperature. The tubes were protected from light while mixing. The solution was then centrifuged for 5 min twice and the supernatant was diluted with 40% methanol for HPLC analysis. The concentrations of taxifolin and the ten flavonolignan components as determined by the HPLC analysis are shown in Table 7b. The toatal anti-oxidant capacity of each sample was determined by phosphomolybdenum method.

TABLE 7b

Solubility of various silymarin components based on HPLC analysis

| Sample | Diluent | Taxifolin (mg/ml) | Ten flavonolignan components (mg/ml) | Total anti-oxidant capacity |
|---|---|---|---|---|
| A1 | $H_2O$ | 0.85 | 0.72 | 2.48 |
| A2 | $H_2O$ | 0.85 | 0.68 | 2.48 |
| A3 | 0.05M CAPTISOL ® | 4.51 | 22.57 | 15.28 |
| A4 | 0.10M CAPTISOL ® | 4.59 | 44.31 | 31.92 |
| A5 | 0.20M CAPTISOL ® | 4.83 | 59.36 | 53.45 |

The solubility of silymarin was also studied at elevated temperatures. The silymarin-water samples were prepared by adding 3.0 ml of deionized water or 3.0 ml of CAPTISOL® solution (0.05 M, 0.10 M, or 0.20 M) to 155 mg silymarin 80% in 5 ml Eppendorf tube, and the tubes were capped securely to minimize evaporation loss and submerged in a water bath at an elevated temperature (60° C. or 75° C.)). CAPTISOL® solutions were prepared by dissolving CAPTISOL® in water. The solution in the tube was stirred for a certain amount of time. The solution was then centrifuged for 5 min twice and the supernatant was diluted with 40% methanol for HPLC analysis. The silymarin CAPTISOL® samples were diluted by adding 10 μL supernatant sample to 990 μL diluent. The silymarin water samples were diluted by adding 100 μL supernatant sample to 900 μL diluent. The diluted samples were then analyzed using HPLC according to the procedures described in Example 1. The concentrations of taxifolin and the ten flavonolignan components are shown in Table 7c.

TABLE 7c

Solubility of various silymarin components at elevated temperatures based on HPLC analysis

| Sample No. | Diluent | Temperature | Stirring time (hr) | Taxifolin (mg/ml) | Ten flavonolignan components (mg/ml) |
|---|---|---|---|---|---|
| B1 | 0.10M CAPTISOL ® | 75° C. | 0.5 | 7.20 | 45.03 |
| B2 | 0.10M CAPTISOL ® | 75° C. | 1 | 7.57 | 45.80 |
| B3 | 0.10M CAPTISOL ® | 75° C. | 2 | 7.49 | 45.06 |
| B4 | 0.10M CAPTISOL ® | 75° C. | 3 | 7.35 | 44.16 |
| B5 | 0.10M CAPTISOL ® | 75° C. | 24 | 7.28 | 43.73 |
| B6 | $H_2O$ | 75° C. | 0.5 | 1.36 | 0.74 |

TABLE 7c-continued

Solubility of various silymarin components at elevated temperatures based on HPLC analysis

| Sample No. | Diluent | Temperature | Stirring time (hr) | Taxifolin (mg/ml) | Ten flavonolignan components (mg/ml) |
|---|---|---|---|---|---|
| B7 | $H_2O$ | 75° C. | 1 | 1.55 | 0.79 |
| B8 | $H_2O$ | 75° C. | 2 | 1.65 | 0.85 |
| B9 | $H_2O$ | 75° C. | 3 | 1.79 | 0.94 |
| B10 | $H_2O$ | 75° C. | 24 | 1.73 | 0.93 |
| B11 | 0.10M CAPTISOL ® | 60° C. | 0.5 | 4.93 | 35.35 |
| B12 | 0.10M CAPTISOL ® | 60° C. | 1 | 5.06 | 37.66 |
| B13 | 0.10M CAPTISOL ® | 60° C. | 2.5 | 5.07 | 38.54 |

Saturated CAPTISOL® silymarin solutions were also prepared by adding 160 mg silymarin to 1 ml of 0.1 M CAPTISOL® solution in a sealed vial under mechanic stirring and the vial was kept in a water bath at 70-75° C. The solution became quickly saturated in about one hour. The solution was then cooled to room temperature and centrifuged, and the supernatant can then be used for preparing various formulations. This procedure increased taxifolin and flavonolignan loadings because the taxifolin was 5-fold higher than in the water silymarin sample and the flavonolignan concentration was about 50 fold higher than the water silymarin sample.

Example 4

Oxygen Radical Antioxidant Capacity (ORAC) Test

The ORAC Activity Assay was based on the oxidation of fluorescein as a fluorescent probe by peroxyl radicals by way of a hydrogen atom transfer (HAT) process. Peroxyl radicals are produced by a free radical initiator (2,2'-Azobis (2-methylpropionamidine) hydrochloride (AAPH)) which quenches the fluorescent probe over time. Antioxidants present in the assay work to block the peroxyl radical oxidation of the fluorescent probe until the antioxidant activity in the sample is depleted. The remaining peroxyl radicals destroy the fluorescence of the fluorescent probe. The sample antioxidant capacity correlated to the fluorescence decay curve, which can be used to quantify the total peroxyl radical antioxidant activity in a sample and be compared to an antioxidant standard curve of the water soluble vitamin E analog Trolox.

The assay was carried out using commercial assay kit (OxiSelect™ Hydrogen Peroxide Assay Kit (Colorimetric) Activity Assay/STA-345, Cell Biolabs, Inc., San Diego, Calif., USA). The hydrophobic protocol of the kit was performed using samples at 0, 2.5, 5, 10, 20, 30, 40, and 50 μM. Results were acquired after one hour of average reading at excitation wave length of 480 nm and emission at 523 nm. The results of the ORAC test are shown in Table 8a.

TABLE 8a

| ORAC values of taxifolin and flavonolignan in the samples | | | | | | | | |
|---|---|---|---|---|---|---|---|---|
| Sample no. | Dilution factor | Trolox equivalent (uMol Trolox) | ORAC Value (uMol Trolox/L) | Number of runs | Average ORAC Value (uMol Trolox/L) | ORAC normalized | Taxifolin (mg · ml) | Ten Flavonolignan components (mg/ml) |
| C1 | 250 | 27.12 | 6779.9 | 2 | 7350 | 1 | 0.40 | 0.46 |
| C2 | 500 | 34.86 | 17432.3 | 2 | 19750 | 3 | n/a | n/a |
| C3 | 1000 | 42.61 | 42609.7 | 1 | 42610 | 6 | 0.96 | 11.60 |
| C4 | 1000 | 42.02 | 42020.4 | 1 | 42020 | 6 | 0.96 | 11.62 |
| C5 | 1000 | 43.70 | 43704.2 | 1 | 43704 | 6 | 0.95 | 11.49 |
| C6 | 1000 | 20.81 | 20805.6 | 1 | 20806 | 3 | 1.65 | 0.85 |
| C7 | 1000 | 21.82 | 21815.8 | 1 | 21816 | 3 | 1.79 | 0.94 |
| C8 | 10000 | 19.37 | 193744.5 | 1 | 193744 | 26 | 4.18 | 39.62 |
| C9 | 10000 | 22.57 | 225735.1 | 1 | 225735 | 31 | 5.25 | 41.14 |
| C10 | 15000 | 19.12 | 286828.4 | 1 | 286828 | 39 | 7.57 | 45.80 |
| C11 | 15000 | 21.98 | 329763.2 | 1 | 329763 | 45 | 7.49 | 45.06 |

The formulations of samples C1 to C11 can be found in Table 8b below. Sample C1 was prepared at room temperature by adding 155 mg silymarin 80% (Indena, Milano, Italy) to 9.845 g of deionized water and stirred overnight. Sample C2 was prepared at room temperature by adding 0.50 g the silymarin Phosphlipids (phytosome) to 9.5 g of water and stirred overnight. Samples C3, C4, and C5 were each independently prepared at room temperature by adding 0.155 g of Silymarin to 9.845 g 0.1 M CAPTISOL® and stirred for at least 48 hrs. Samples C6 and C7 were prepared at 75° C. by adding a large excess of silymarin to 9.845 g of deionized water; C6 sample was stirred in a sealed vial for 2 hr and C7 sample was stirred in a sealed vial for 3 hr. Sample C8 was prepared at room temperature by adding 260 mg silymarin 80% to 9.845 g of 0.1 M CAPTISOL® and equilibrated by stirring for at least 48 hrs, and Sample C9 was prepared at room temperature by adding 360 mg silymarin to 9.845 g of 0.1 M CAPTISOL® and equilibrated by stirring for at least 48 hrs. Samples C10 and C11 were prepared at 75° C. by adding 155 mg silymarin to 9.845 g of 0.1 M CAPTISOL®; C10 sample was stirred for 1 hr and C11 sample was stirred for 2 hr. Samples C6 to C11 all had large excess of undissolved silymarin in the original vial. All of the samples C1 to C11 were centrifuged prior to sampling.

TABLE 8b

| Silymarin formulations for samples C1 to C11. | |
|---|---|
| Sample no. | Formulation Details |
| C1 | Silymarin in water prepared at room temperature with 155 mg silymarin |
| C2 | Silymarin Phosphlipids (phytosome) prepared at room temperature |
| C3 | Silymarin in 0.1M CAPTISOL ® prepared at room temperature with 155 mg silymarin |
| C4 | Silymarin in 0.1M CAPTISOL ® prepared at room temperature with 155 mg silymarin |
| C5 | Silymarin in 0.1M CAPTISOL ® prepared at room temperature with 155 mg silymarin |
| C6 | Silymarin in water prepared at 75° C. and stirred for 2 hr with large excess of silymarin |
| C7 | Silymarin in water prepared at 75° C. and stirred for 3 hr with large excess of silymarin |
| C8 | Silymarin in 0.1M CAPTISOL ® prepared with 260 mg silymarin |
| C9 | Silymarin in 0.1M CAPTISOL ® prepared with 360 mg silymarin |
| C10 | Silymarin in 0.1M CAPTISOL ® prepared at 75° C. and stirred for 1 hr with 155 mg silymarin |

TABLE 8b-continued

| Silymarin formulations for samples C1 to C11. | |
|---|---|
| Sample no. | Formulation Details |
| C11 | Silymarin in 0.1M CAPTISOL ® prepared at 75° C. and stirred for 2 hr with 155 mg silymarin |

Figure 16:
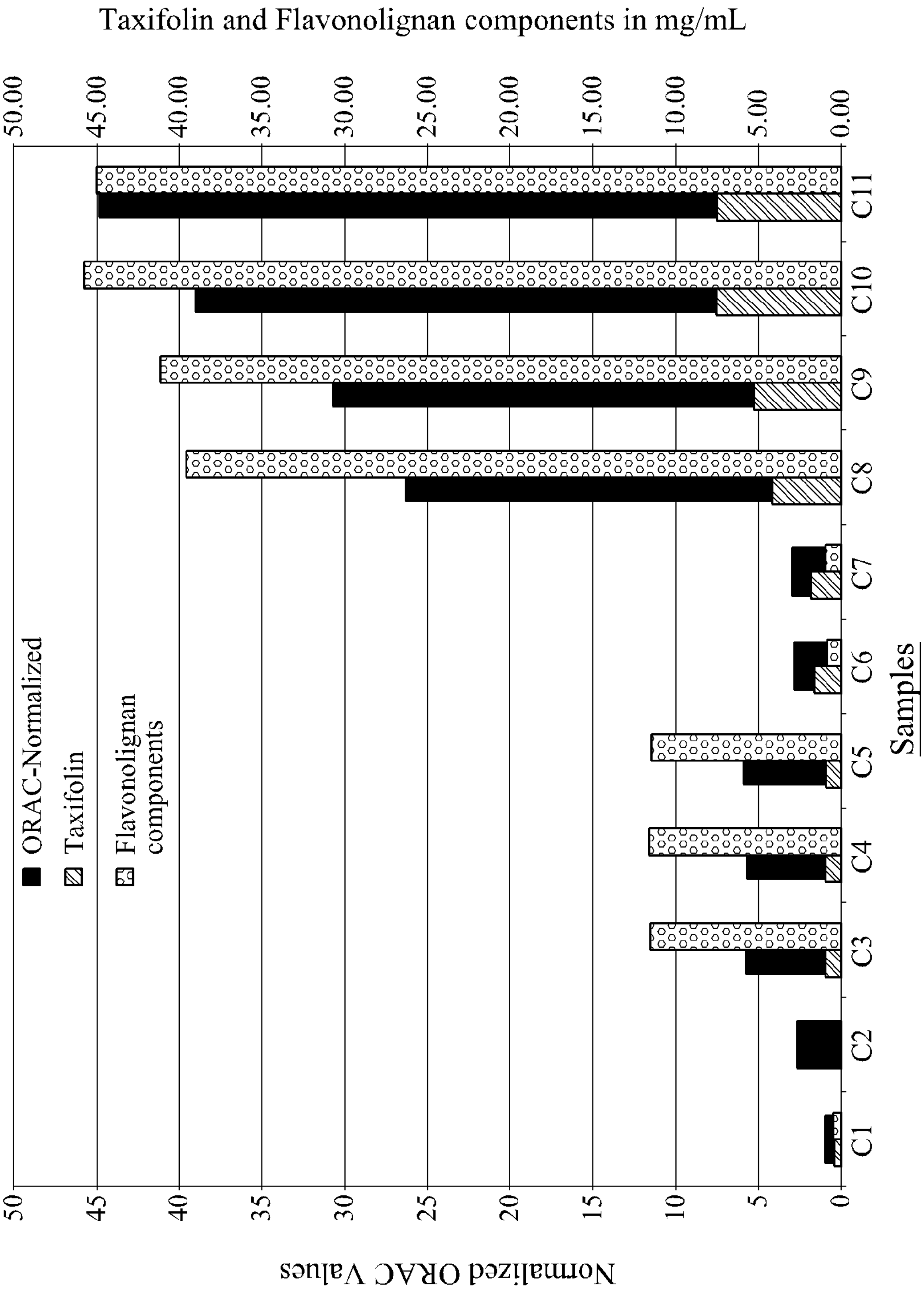
FIG. 16 shows the oxygen radical antioxidant capacity of taxifolin and flavonolignan components in the silymarin samples.

The above prepared solutions were then centrifuged for 5 min. The supernatants were diluted according to the dilution factor in Table 8a with 40% methanol and then used for HPLC and/or ORAC analysis. The ORAC values of the taxifolin and flavonolignan components are also shown in FIG. 16.

Example 5

Anti-inflammatory Activity (IL-8)

The test solutions were prepared from the composition detailed in Table 9a using the following procedure: (i) All of the required excipients for each test solution listed in Table 8a were sequentially weighed into a suitably sized vial; (ii) the solution from Step (i) was then vortexed for 30 s to disperse the Test Item component, through the solution; (iii) the test solutions was homogenized at 10,800 RPM for 2 min in short bursts 10-20 s to avoid foaming using the Silverson homogenizer.

TABLE 9a

| Composition of test solutions | | |
|---|---|---|
| | CAPTISOL ®-Silymarin | Silymarin extract |
| Silymarin | 0.155 g | 0.155 g |
| CAPTISOL ® 50 mM solution | 9.845 g | n/a |
| Vehicle (Water for injection) | n/a | 9.845 g |

The CAPTISOL® 50 mM solution was prepared using the following procedure: (i) CAPTISOL® (1.5166±0.01 g) was weighed into a 20 mL volumetric flask; (ii) the volumetric flask was half filled with water for injection, then vortexed until dissolution was observed; (iii) the volumetric of Step (ii) was made up to volume using water for injection and the solution was stirred until the CAPTISOL® had fully dissolved.

Tissue model: Two types of RHE tissue models were used, psoriasis tissue and healthy full thickness controls. To culture each type of a tissue corresponding serum free maintenance media was required.

On arrival until the tissues were handled using the following procedure:

(i) Tissues where transferred to the fridge stored at 2-8° C. (for a maximum of 48 h) on arrival until the day prior to application of Test Items.

(ii) On the day prior to application of Test Items the wells of a 6-well plate were filled with pre-warmed (37° C.) maintenance media (0.9 mL, supplied with the tissues) using an automatic pipette.

(iii) The tissue was removed from the packaging, cleaned to remove the transport agarose using dry cotton swabs and then inspected visually for signs of damage. Any visually damaged tissues were discarded.

(iv) The tissue was transferred into the growth culture medium and then incubated at 37° C., 5% $CO_2$ for the equilibration period (overnight 16-18 h).

Application of test item and control: All Test Items for the small scale experiments were tested in duplicate using one batch of tissue according to the following method:

(i) At the end of the equilibration period (the media was aspirated from each well of the 6-well plates containing the tissue inserts and a culture stand (used to raise the tissue to the liquid-air interface) was placed into each well of the 6-well plate.

(ii) Into the 6-well plate (step (i)), 5 mL of pre-warmed maintenance medium was added using an automatic pipette and the tissues were then placed on top of the culture stand. Care was taken to avoid trapping any air bubbles between the tissue and the surface of the media.

(iii) The test item was dispensed (100±0.5 μL) onto the top of the RHE tissue, using positive displacement pipette. The Test Item or control (water) was distributed over the surface of the RHE tissue using a glass rod (the glass rod was wiped clean with 70% v/v ethanol in water between each application and allowed to dry).

(vi) The plate lid was replaced and the tissues were returned to the incubator (37° C., 5% CO2) for the required dosing period (6, 24 and 30 h).

Sample collection, preparation, and analysis: For both tissue models employed during the feasibility investigation, the incubation media was collected and analyzed. In addition, the full thickness healthy tissues were lysed and analyzed. Analysis of incubation media was used to determine the extracellular release of markers from the tissues and analysis of tissue lysates for intracellular levels of the markers.

To investigate the intercellular changes in response to treatment with the Test Item tissue lysates were prepared for analysis as described below:

(i) Following treatment with the Test Items the tissues inserts were removed from the assay plate and a biopsy punch was used to taken to harvest the tissue from the insert the plastic insert. Forceps were then used to separate this tissue from the insert.

(ii) The tissue (step (i)) was then transferred into a 1.5 mL centrifuge tube containing 500 μL of cell lysis buffer (R&D systems); the centrifuge tube was the incubated on ice for 30 min to allow cell lysis to occur.

(iii) After lyses (Step (i)) the cell debris was then pelleted by centrifugation (13,000 rpm for 5 min).

(iv) The supernatant was removed from the centrifuge tube (Step (iii)) and stored at −80° C. until required, an aliquot of this sample was removed prior to marker analysis to quantify the protein concentration by bicinchoninic acid assay (BCA assay).

BCA protein assay: This assay was conducted using Pierce® BCA Protein Assay Kit according to the manufactures instructions as follows.

(i) From the supplied bovine serum albumin (BSA) standard, BSA calibration standards were prepared, in which BSA was diluted to final volume using phosphate buffer (50 mM, pH 7.4) as the diluent.

(ii) A BCA working reagent solution was prepared by mixing 50 parts of BCA Reagent A (bicinchoninic acid) with 1 part of BCA Reagent B (4% copper sulphate solution) (50:1, Reagent A:B).

(iii) Into a microwell plate, 25 μL of each standard or test sample was pipetted in duplicate.

(iv) Into the wells containing the samples and controls (Step (iii)), 200 μL of BCA working reagent solution was then added using an automatic pipette.

(v) The plate was covered with a sealing film and incubated at 37° C. for 30 minutes.

(vi) The plate was then cooled to ambient temperature and the absorbance of the solutions was measured at 562 nm using a μQuant spectrophotometer.

ELISA assay: The markers that were analyzed are summarized in Table 9b, all were quantified using commercial kits which were used according to the respective manufactures instructions.

TABLE 9b

Feasibility potential markers studied

| Type of Marker | Marker |
|---|---|
| Inflammatory markers | IL-6 (Invitrogen ELISA: Human IP-6) |
| | IL-8 (Quantikine ELISA: Human CXCL8/IL-8 immmunoassay) |
| | IP-10 ((Invitrogen ELISA: Human IP-10) |
| Skin Structure Markers | Procollagen (DuoSet ELISA: Human Procollagen Iα1-COLIA1) |
| | Fibronectin (Biovision ELISA: human firbonectin) |
| Anti-oxidant effects | Superoxide dismutase activity (OxiSelect Superoxide dismutase activity assay) |

The anti-inflammatory activity of SAE-CD/silymarin compositions were tested using a psoriasis tissue model (MatTek Corporation, Ashland, Mass., USA). These tissues have elevated release of inflammatory cytokines related to psoriasis including interleukin 8 (IL-8). The effects of the CAPTISOL®-silymarin composition were tested for their potency in reducing the expression of these cytokines in the in vitro model. The test solutions and tissues were prepared using the procedures described above.

The psoriasis tissue model was dosed with a CAPTISOL®-silymarin composition in water solution, and then incubated at 37° C. for 6 h, 24 h, and 30 h. For the control, the psoriasis tissue model was treated with water only as a control group and was incubated at 37° C. for 6 h, 24 h, and 30 h. The tissue model was analyzed and the IL-8 levels were determined using the procedures described above.

Figure 7:
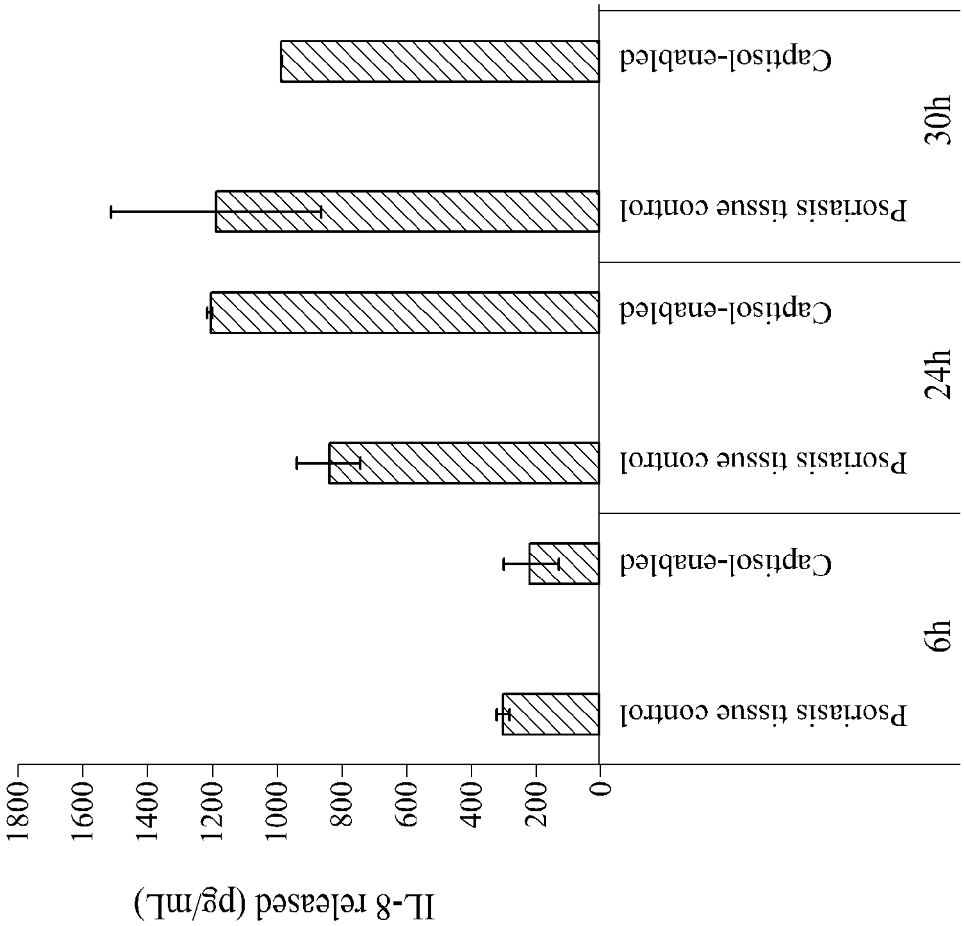
FIG. 7 shows the effect of a sulfobutylether-β-cyclodextrin/silymarin composition on the level of IL-8 marker as tested in Example 3.

Levels of IL-8 for the control and test composition are shown in FIG. 7. The IL-8 level in the sample treated with the CAPTISOL®-silymarin composition was lower at 6 h, 24 h, and 30 h when compared with the control.

Example 6

Intracellular Levels of ROS/RNS

Figure 8A:
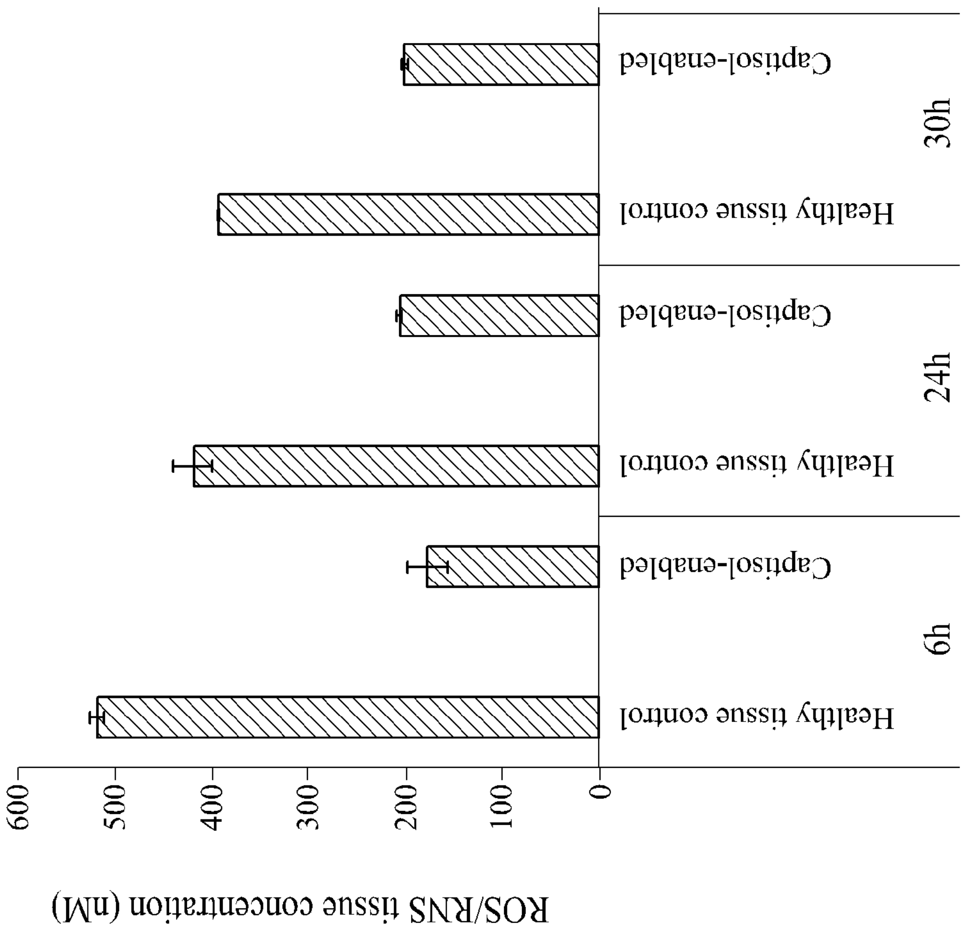
FIG. 8A shows the effect of a sulfobutylether-β-cyclodextrin/silymarin composition on the intracellular levels of ROS/RNS as tested in Example 4.
Figure 8B:
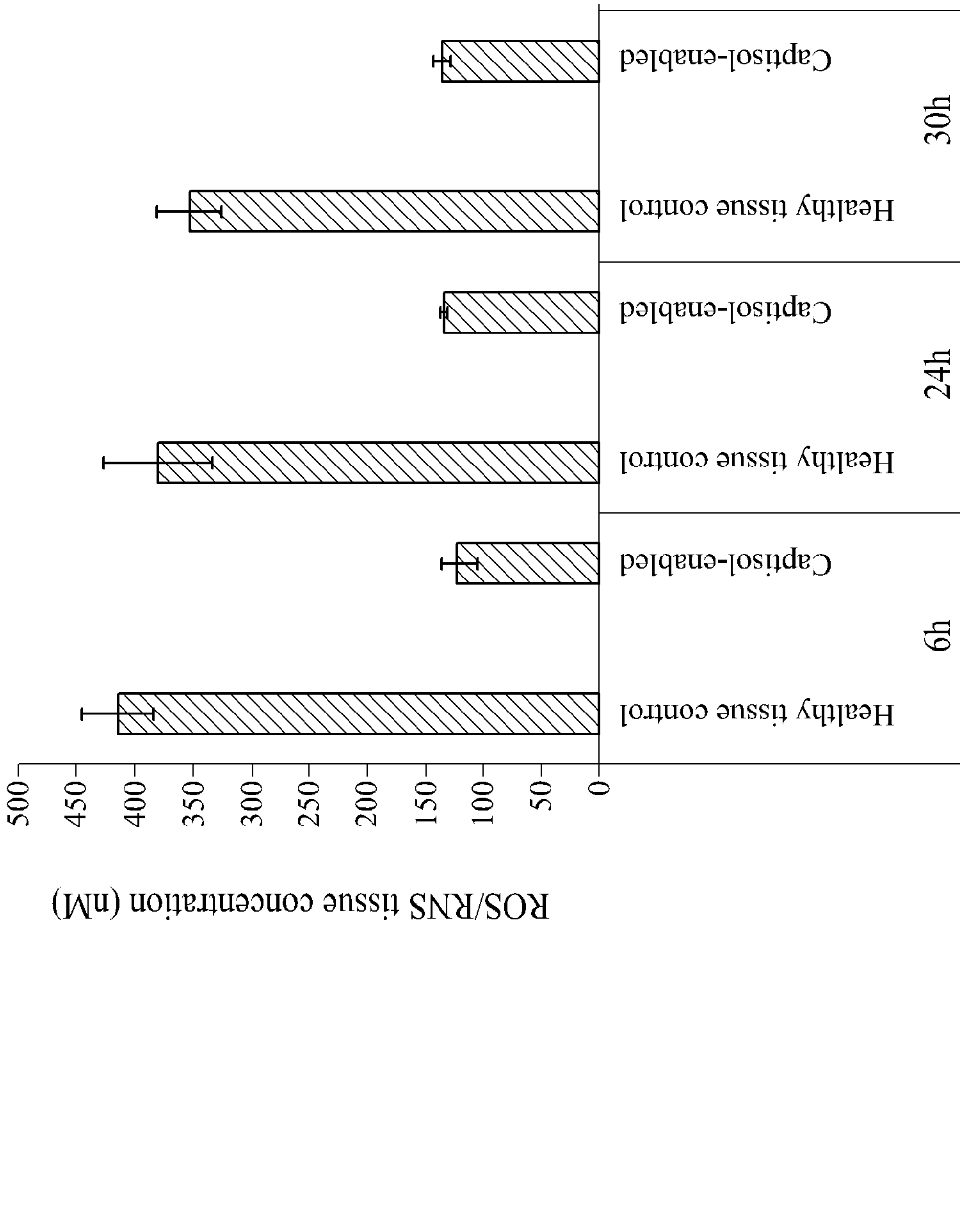
FIG. 8B shows the intracellular levels of ROS/RNS after normalized for protein content.

The sample solutions were prepared and test was performed according to the procedures described in Example 5. The effects of CAPTISOL®-silymarin compositions on intracellular levels of ROS/RNS were tested using a healthy full thickness tissue model. A water-only control sample was used. At 6 h, 24 h, and 30 h time points, the tissues were lysed and analyzed for intracellular levels of ROS/RNS. As shown in FIG. 8A, the sample treated with the CAPTISOL®-silymarin composition showed reduced levels of ROS/RNS at each of the three time points when compared with the healthy tissue control sample. This result demonstrates the anti-oxidant properties of the CAPTISOL®-silymarin composition. FIG. 8B shows the results when normalized for protein content. As shown in FIG. 8B, the sample treated with the CAPTISOL®-silymarin composition showed reduced levels of ROS/RNS at each of the three time points 6 h, 24 h, and 30 h, when compared with the control sample Example 7

Anti-Inflammatory Activity (IL-6 and IL-10)

The sample solutions were prepared and test was performed according to the procedures described in Example 5. The anti-inflammatory activity of a CAPTISOL®-silymarin composition was tested using a psoriasis tissue model (MatTek Corporation, Ashland, Mass., USA). These tissues have elevated release of the inflammatory cytokines interleukin 6 (IL-6) and interferon gamma-induced protein 10 (IP-10). The CAPTISOL®-silymarin composition was tested for its potency in reducing the expression of these cytokines in the in vitro model.

The psoriasis tissue model was dosed with CAPTISOL®-silymarin composition in water, and then incubated at 37° C. for 48 h, 96 h, and 144 h. For the control, the psoriasis tissue model was treated with water only and was incubated at 37° C. for 48 h, 96 h, and 144 h.

Figure 9:
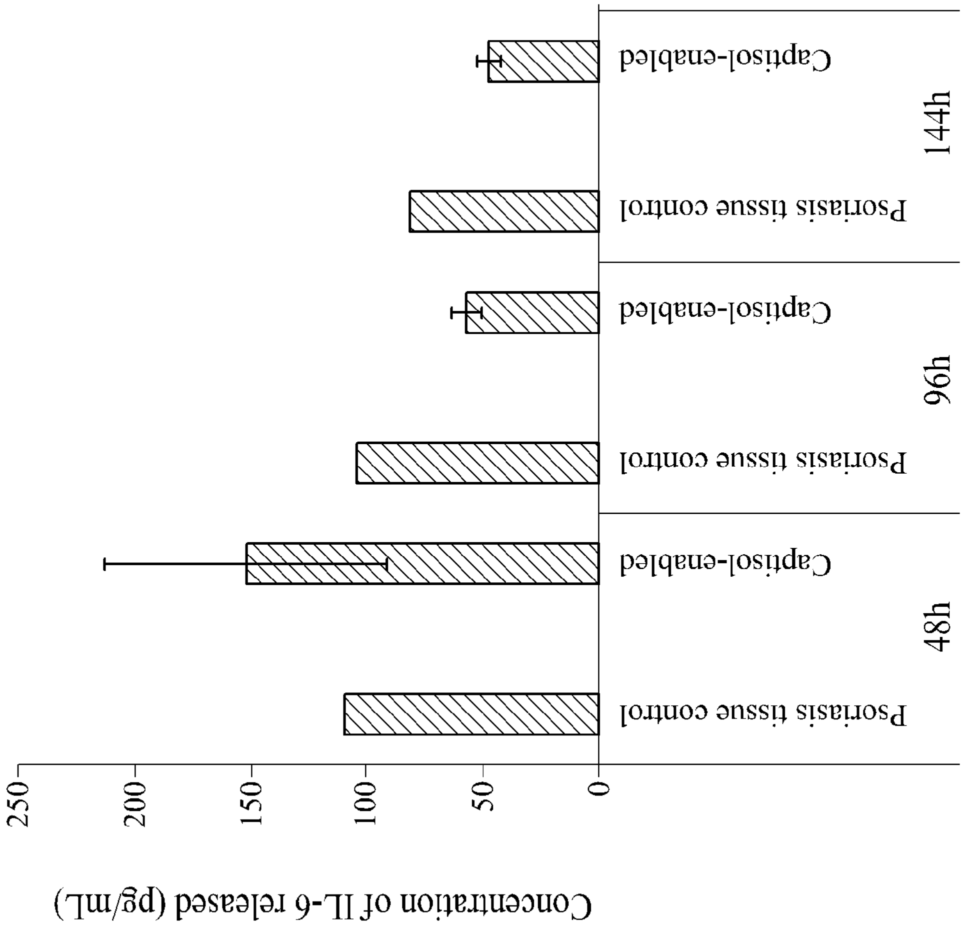
FIG. 9 shows the effect of asulfobutylether-β-cyclodextrin/silymarin composition on the intracellular level of IL-6 as tested in Example 5.

Levels of IL-6 for the control and test composition are shown in FIG. 9. The IL-6 level in the sample treated with the CAPTISOL®-silymarin composition was lower at each of the three time points when compared with the control.

Figure 10:
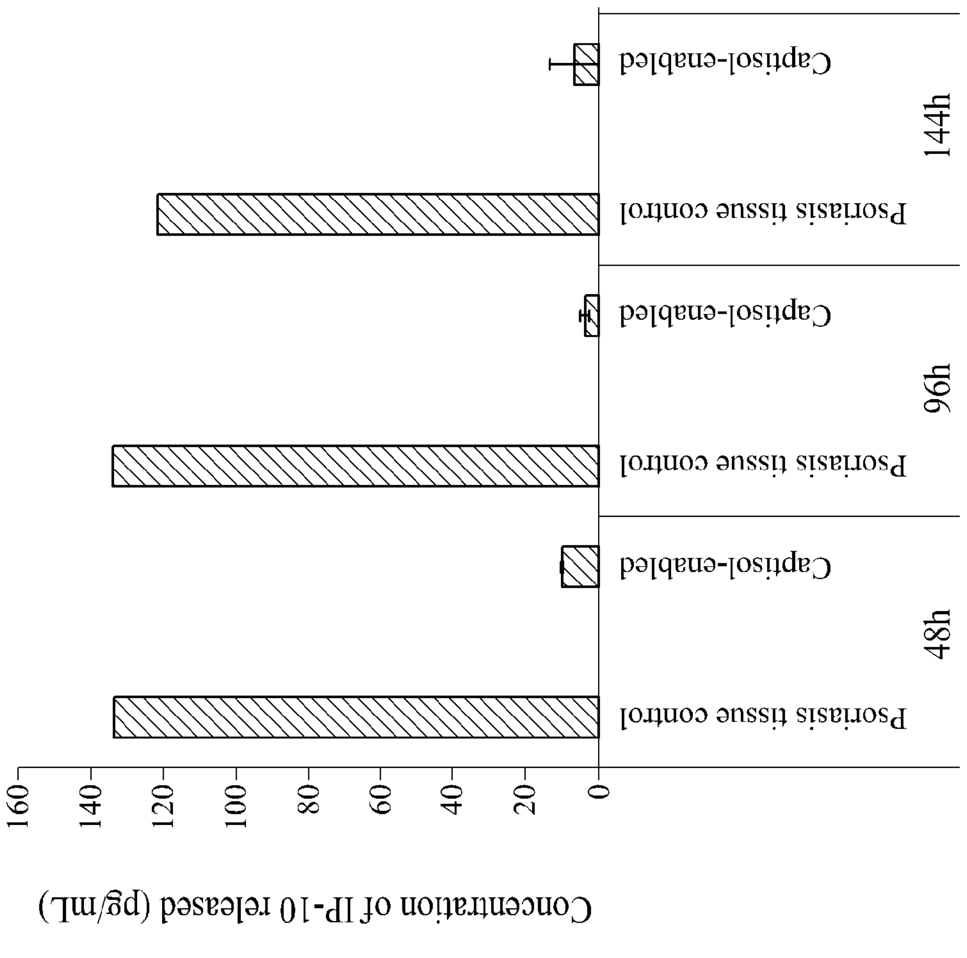
FIG. 10 shows the effect of a sulfobutylether-β-cyclodextrin/silymarin composition on the intracellular level of IP-10 as tested in Example 5.

Levels of IP-10 for the control and test composition are shown in FIG. 10. The IP-10 level in the sample treated with the CAPTISOL®-silymarin composition was lower at each of the three time points when compared with the control group.

Example 8

Effect on Fibronectin and Procollagen

Figure 11:
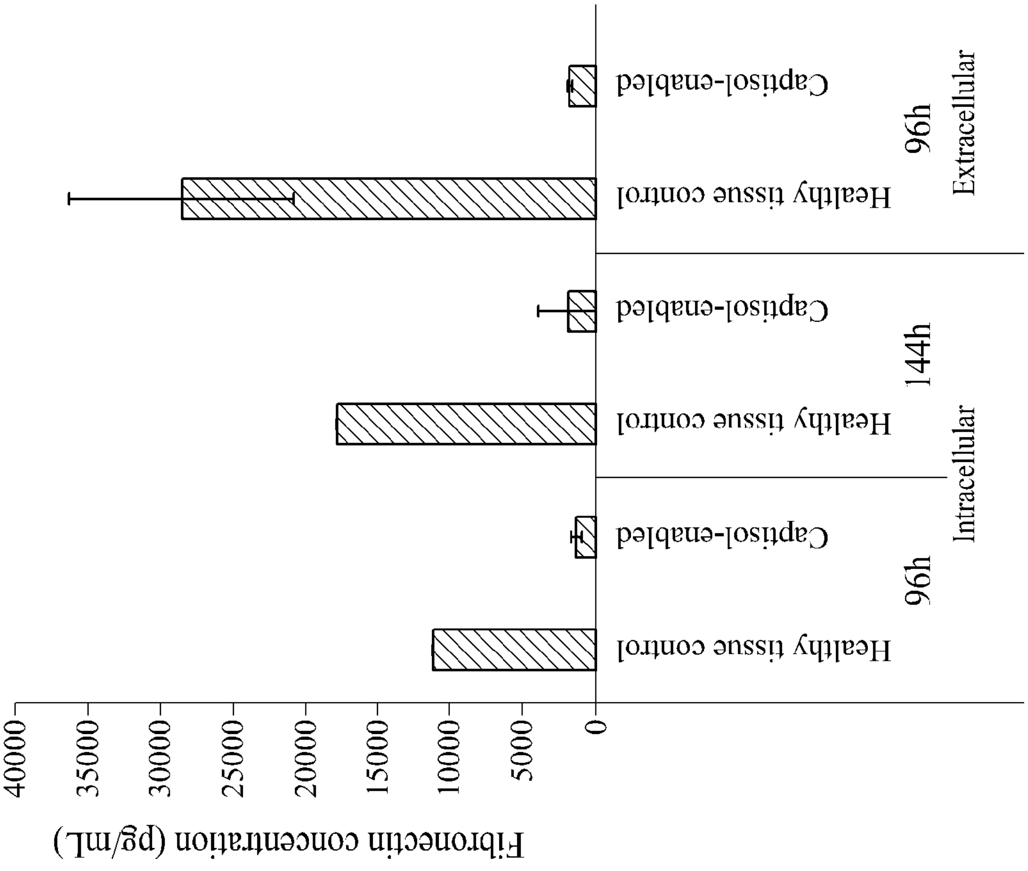
FIG. 11 shows the effect of a sulfobutylether-β-cyclodextrin/silymarin composition on fibronectin concentration as tested in Example 6.
Figure 12:
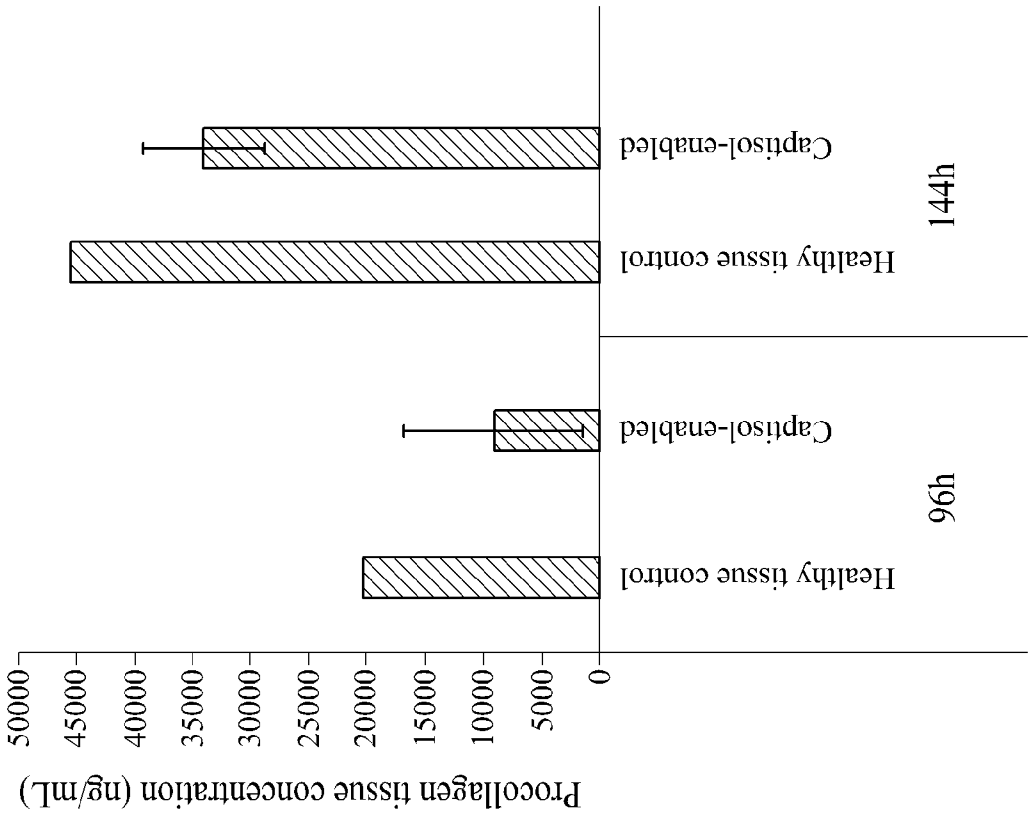
FIG. 12 shows the effect of a sulfobutylether-β-cyclodextrin/silymarin composition on procollagen concentration as tested in Example 6.

The effect of CAPTISOL®-silymarin on the structural markers fibronectin and pro-collagen were tested using a healthy full thickness tissue model. Intracellular fibronectin and pro-collagen levels were measured at 96 h and 144 h. For the control, the tissue model was treated with water only. The resulting fibronectin levels are shown in FIG. 11. Fibronectin concentration in the tissues was reduced by the CAPTISOL®-silymarin composition at both time points when compared with the control. The resulting pro-collagen levels are shown in FIG. 12. The intracellular level of pro-collagen was also reduced by the CAPTISOL®-silymarin composition at both time points. In addition, the control and the CAPTISOL®-silymarin composition samples at 96 h were assayed in the conditioned medium to determine the extracellular release of fibronectin. The results are shown in FIG. 11 and demonstrated that the extracellular level of fibronection was reduced by the CAPTISOL®-silymarin composition as compared to the control.

These results support that CAPTISOL®-silymarin can help to accelerate wound healing and preventing scar formation.

Example 9

Gel Formulation

The solubility of silymarin was determined in various solvents as shown in Table 10a below. The solubility of Silymarin in the selected excipients was assessed using the following procedure:

(i) A known weight of Silymarin (Table 12) each excipient was weighed into a 20 mL glass vial.

(ii) Approximately 1.0 g of each of the excipients was added to the individual glass vials from Step (i).

(iii) The Silymarin and excipient were stirred for >16 h (once saturation was observed). The solutions were stirred in a pre-calibrated water bath at 25° C.

(iv) During stirring the solutions were visually inspected hourly (where possible) to observe if the Silymarin had dissolved in the excipients.

(v) If the Silymarin was observed to completely dissolve, then an additional quantity of Silymarin was added to the vial, where the Silymarin was insoluble additional excipients was added in suitable increments (250-1000 mg) dependent on the visual assessment of the solubility of Silymarin.

TABLE 10a

Solubility of Silymarin in excipient (% w/w/) demined by visual assessment

| Excipient | Solubility of Silymarin in excipient (% w/w) |
|---|---|
| Ethanol | 11.17 |
| Isopropanol (Isopropyl alcohol) | 3.39 |
| Benzyl alcohol | 6.86 |
| Deionised water | <0.39 |
| Phenoxyethanol | 7.71 |
| PEG 400 | 5.96 |
| Dimethyl Isosorbide (SR Arlasolve DMI) | 10.19 |
| Propylene glycol | 5.14 |
| Transcutol P | 9.96 |
| Diisopropyl adipate | <1.99 |
| Glycerin (Glycerol) | <0.30 |

Based on the solubility experiments described above, suitable solvent systems were developed to form the basis of a gel formulation. A solvent system was developed to incorporate the silymarin into a gel formulation as shown in Table 10b. The solubility of Silymarin in the solvent systems was determined as follows:

(i) Each solvent system was prepared by the sequential weighing of the required solvents in Table 10b to prepare a 10 g batch of the solvent system (ii) The solvent systems were thoroughly stirred until visually homogeneous and the solubility of the Silymarin was determined. The solubility of Silymarin in the solvents systems was difficult to assess visually, with two distinct trends observed in the solvent systems. The Silymarin was insoluble at 0.34-0.35% w/w (SS2, SS5 and SS6) with distinguishable clumping of solid Silymarin in the system. In the remaining systems (SS1, SS3 and SS4) Silymarin dispersed in the system and appeared to be in suspension. These systems (SS1, SS3 and SS4) were then further assessed to determine the solubility of Silymarin down to 0.08% w/w where there was still evidence of Silymarin in suspension suggesting that the solubility of Silymarin is lower than 0.08% in all 3 systems.

TABLE 10b

Compositions of excipients in the developed solvent systems (% w/w) and the observations of Silymarin solubility.

| | Compositions of excipients % w/w (of excipients in each system) | | | | | |
|---|---|---|---|---|---|---|
| Solvent systems | SS1 | SS2 | SS3 | SS4 | SS5 | SS6 |
| Phenoxyethanol | — | 1 | 1 | 1 | 1 | 1 |
| Ethanol | — | 10 | 10 | 10 | 10 | 5 |
| PEG 400 | — | — | 20 | — | — | 10 |
| Transcutol P | — | — | — | 15 | — | — |
| Dimethyl Isosorbide | — | — | — | — | 15 | — |
| 100 mM CAPTISOL ® | 100 | 89 | 69 | 74 | 74 | 84 |
| Total | 100 | 100 | 100 | 100 | 100 | 100 |
| Silymarin loading (% w/w) | 0.43 | 0.34 | 0.40 | 0.39 | 0.35 | 0.34 |
| Observations | Silymarin dispersed through the solvent system | Clumps of Silymarin visible | Silymarin dispersed through the solvent system | Silymarin dispersed through the solvent system | Clumps of Silymarin visible | Clumps of Silymarin visible |

Based on the results of the solubility experiments, it was determined that in order to achieve the highest loading of Silymarin in the gel formulations, the 3 solvents systems that had the highest solubility for Silymarin (SS1, SS3 and SS4) were saturated with Silymarin. This was done by addition of 1 w/w of Silymarin to each solvent system (SS1, SS3 and SS4) and stirring for 24 h to achieve maximum solubility. The resulting suspensions were then centrifuged to remove the insoluble Silymarin, and the solutions were visually assessed for the degree of yellow coloration to determine the Silymarin concentration in solution. The solvent system with the highest loading was determined to be SS3. As a result SS3 was used to prepare a gel formulation by diluting the saturated solvent system (SS3) by 10% with the SS3 solvent system to prevent physical instability of the final formulation. The 90% saturated solvent system and the corresponding placebo (SS3 solvent system alone without silymarin) were then made into gel formulations by adding 1% w/w polymer (HPC or HEC). Table 11 summarizes the results of the gel formulation tests, showing that the hydroxypropyl cellulose (HPC) in combination with SS3 produced a good gel formulation.

TABLE 11

Polymers selected for forming gel formulation.

| Final formulation name | Solvent System | Polymers | Macroscopic appearance | Micro-scopic | pH |
|---|---|---|---|---|---|
| CAPTISOL ® vehicle gel | SS3 (without silymarin) | Hydroxy-propyl cellulose (HPC) | Transparent fully hydrated gel | No evidence of drug crystal-lization | 6.63 |
| n/a | SS3 (without silymarin) | Hydroxy-ethyl cellulose (HEC) | Polymer did not hydrate | n/a | n/a |
| CAPTISOL ®-silymarin gel | SS3 (90% silymarin saturation) | Hydroxy-propyl cellulose (HPC) | Yellow transparent fully hydrated gel | No evidence of drug crystal-lization | 5.48 |
| n/a | SS3 (90% silymarin saturation) | Hydroxy-ethyl cellulose (HEC) | Polymer did not hydrate | n/a | n/a |

To this end the procedure below was followed to prepare the final gel formulations:

(i) Silymarin was weighed (150 mg) into a 20 mL glass vial.
(ii) Approximately 1.0 g of each solvent system (SS1, SS3 and SS4; Table 13) was added to the individual glass vials from Step (i).
(iii) After 1 h, an additional aliquot of each solvent system was added to each individual vial to a total of 14.85 g to produce a 1% solution of the Silymarin.
(iv) The Silymarin and solvent systems were stirred for >24 h in a pre-calibrated water bath at 25° C.
(v) The saturated solvent systems were then centrifuged at 4000 rpm for 10 min to remove any undissolved Silymarin.
(vi) The saturated solvent systems were then assessed visually to determine the highest level of Silymarin in solution based on solution colour and quantity of undissolved Silymarin.

(vii) The selected saturated solvent system (Step (vi), SS3) was then diluted with SS3 by 10% to avoid Silymarin precipitation when the formulations were prepared.

(viii) This solvent system was then used to prepare gels using two HPC at 1% w/w in the solvent system.

(ix) The active formulations were assessed for macroscopic appearance, absence of crystallization/microscopic appearance, and pH.

Example 8

Anti-Inflammatory Activity

A full scale test was undertaken to determine the effect of CAPTISOL®-silymarin gel formulation on inflammation by measuring the release of IL-6 from the in vitro psoriasis tissue model. The full scale dosing and sampling plan detailing the number of samples collected and analyzed are shown in Table 12.

TABLE 12

Full scale dosing and sampling details.

| Tissue Type | Treatment | Number of tissues to be treated | Time points 48 h | 96 h |
|---|---|---|---|---|
| Psoriasis tissues (24 tissue) | CAPTISOL ®-Silymarin gel | 6 | — | 6 |
| | Silymarin extract | 6 | — | 6 |
| | water treated | 6 | — | 6 |
| | CAPTISOL ® gel | 6 | — | 6 |
| | Total | 24 | 0 | 24 |
| Healthy full thickness controls (24 tissue) | CAPTISOL ®-Silymarin gel | 6 | 6 | — |
| | Silymarin extract | 6 | 6 | — |
| | Water treated | 6 | 6 | — |

Figure 13:
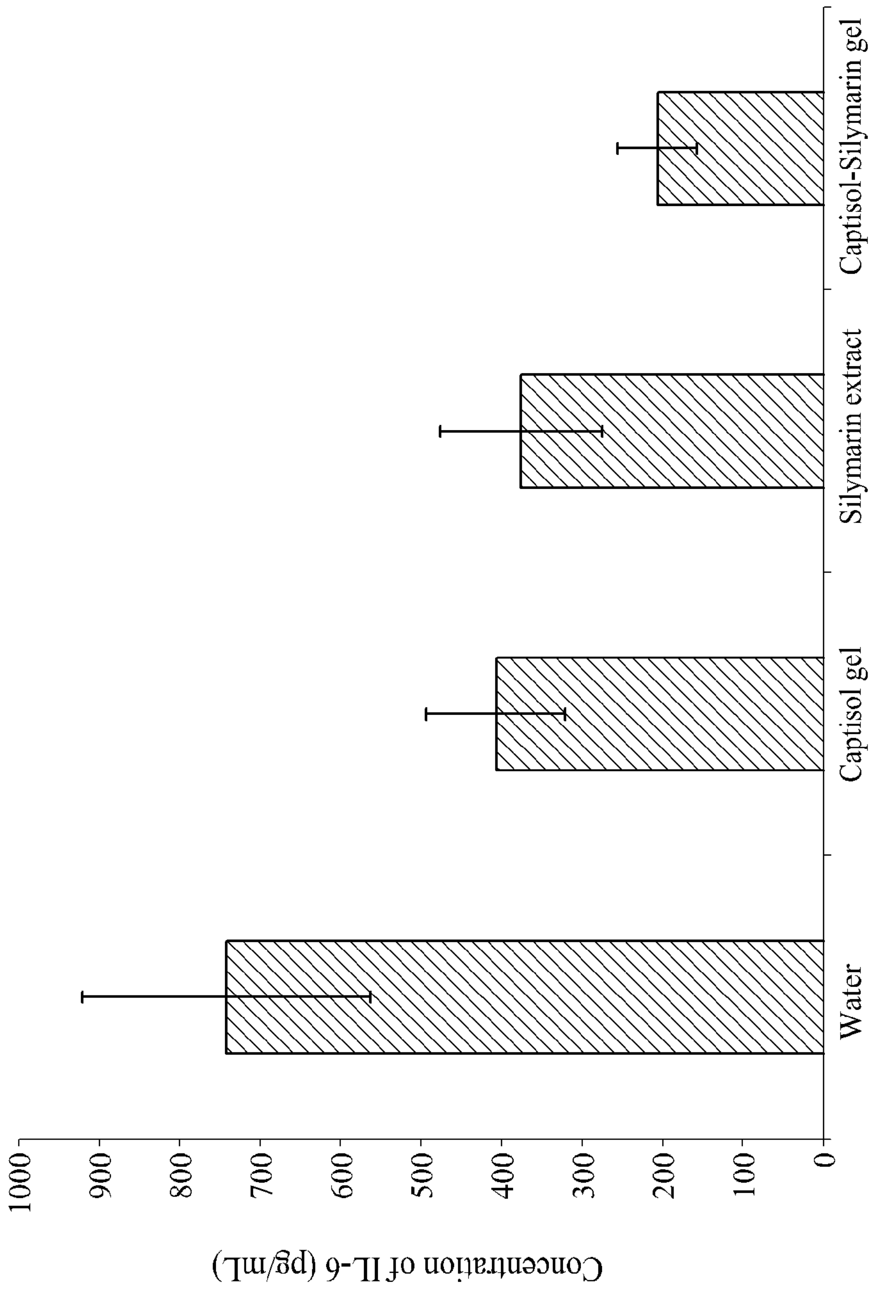
FIG. 13 shows the effect of a sulfobutylether-β-cyclodextrin/silymarin composition on the intracellular level of IL-6 in a psoriasis tissue model.

The psoriasis tissues were treated for 96 h with CAPTISOL®-silymarin gel, Silymarin extract, water treated and CAPTISOL® vehicle gel. The release of IL-6 was then quantified by ELISA and the results are summarized in FIG. 13. The IL-6 level was the lowest in the CAPTISOL®-silymarin gel treatment group when compared with the water control group, CAPTISOL® vehicle gel group, and silymarin extract group. Compared with the water treated group, the other three groups showed a significant reduction of IL-6 level ($p<0.001$). The largest reduction was observed in the CAPTISOL®-silymarin gel group (72% reduction compared to the water treated tissue), confirming its anti-inflammatory properties. When compared to the experiment performed in Example 5 which did not use gel formulation, the reduction in IL-6 with the gel formulation was greater (Example 5 reduction in IL-6 49%). The test results suggest that the gel formulation has improved the anti-inflammatory activity of CAPTISOL®-Silymarin composition.

Example 9

Intracellular Levels of ROS/RNS

Figure 14:
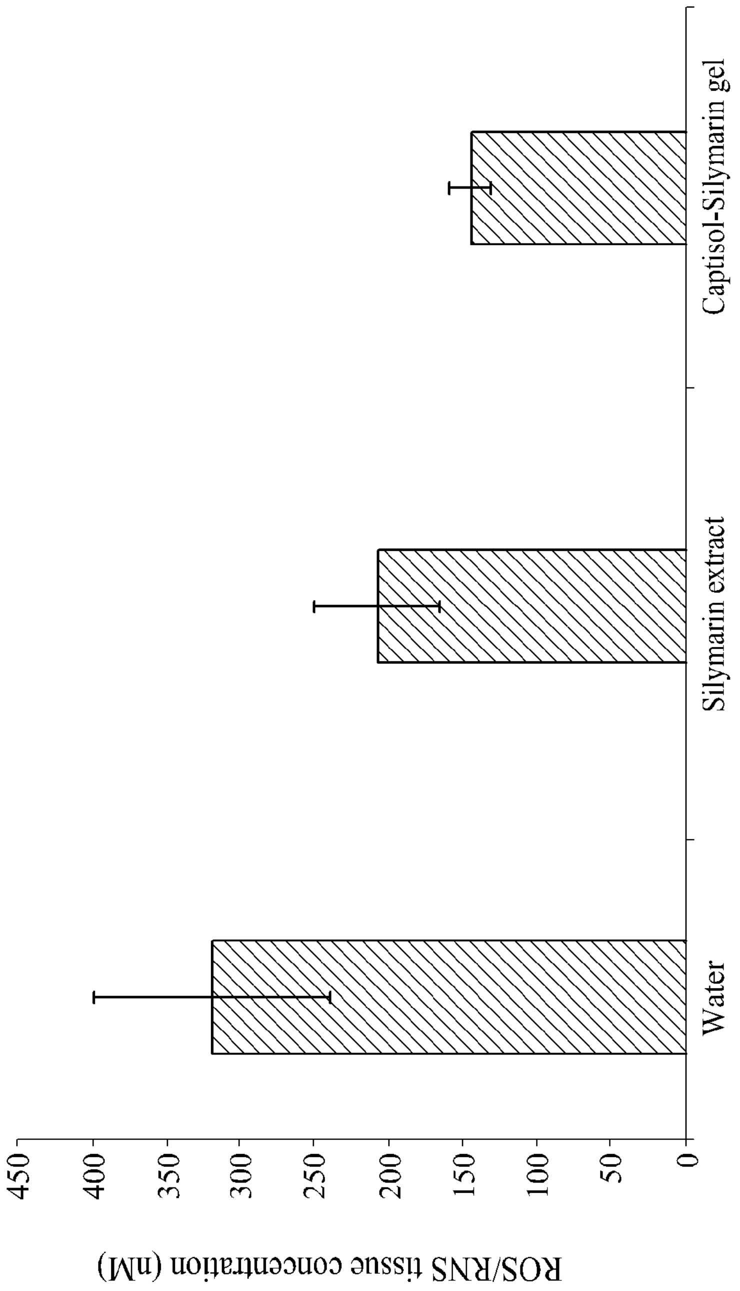
FIG. 14 shows the effect of a sulfobutylether-β-cyclodextrin/silymarin composition on the intracellular level of ROS/RNS in a healthy fullness control model.

The effect of CAPTISOL®-silymarin gel formulation on the levels of ROS/RNS in an in vitro healthy full thickness skin model was also tested to determine the antioxidant potential of the CAPTISOL®-silymarin gel. The healthy full thickness control model tissues were treated for 48 h with CAPTISOL®-silymarin gel, Silymarin extract, and water. Tissue lysates were then prepared, and the lysates were analyzed for intracellular levels of ROS/RNS. As shown in FIG. 14, the group treated with CAPTISOL®-silymarin gel formulation showed 54% reduction in ROS/RNS level ($p<0.005$) when compared with the group treated with the water. The CAPTISOL®-silymarin gel treatment group also showed lower ROS/RNS level than the group treated with the silymarin extract. The test results demonstrated that the anti-oxidant properties of CAPTISOL®-silymarin gel formulation have improved the anti-inflammatory activity of CAPTISOL®-Silymarin composition.

Example 10

Physiochemical Properties of Silymarin

Figure 17:
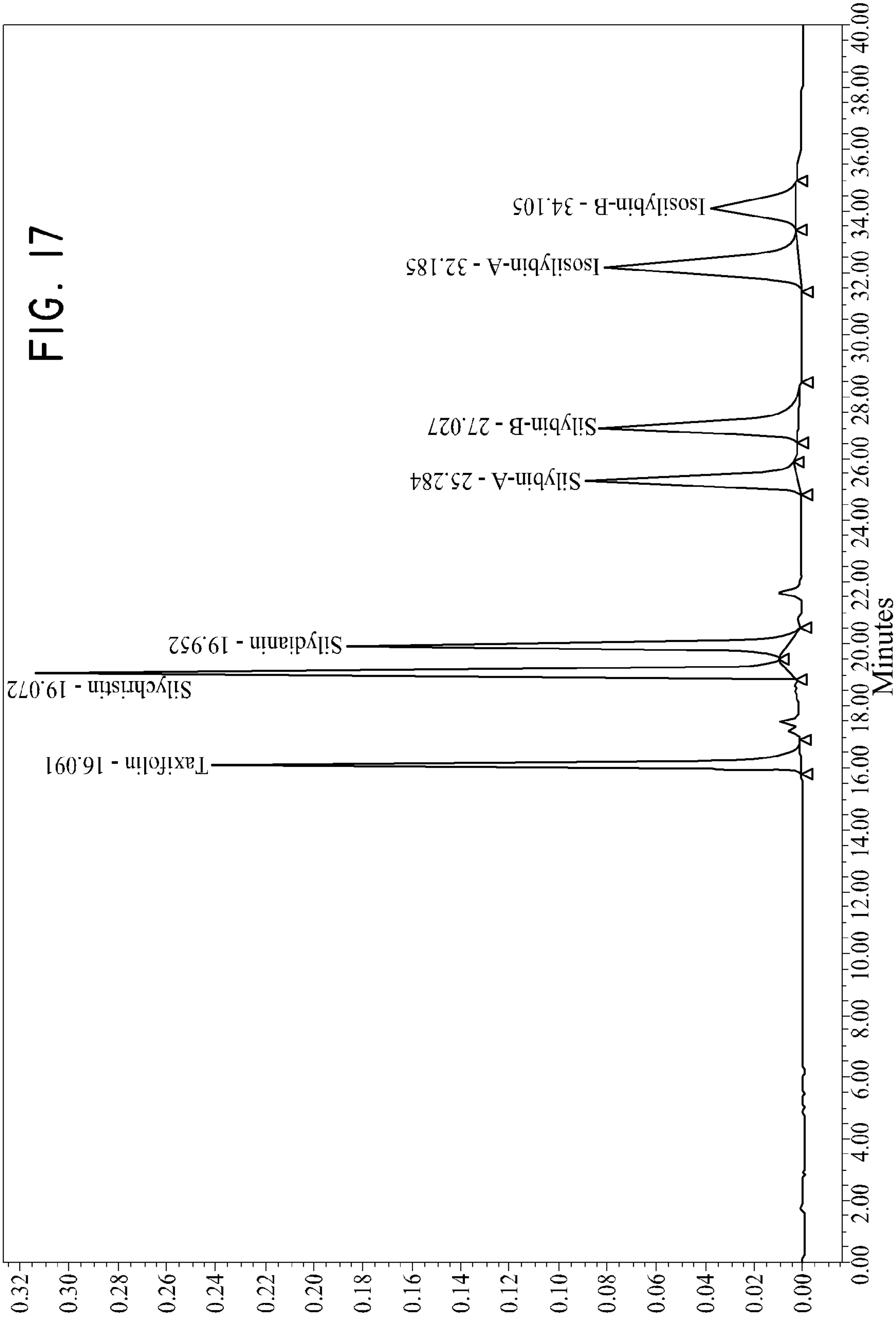
FIG. 17 shows the HPLC chromatogram of silymarin components measured in Example 10.

Silymarin components including taxifolin, silydianin, silychristin, silybin A, silybin B, isosilybin A, and isosilybin B were tested for their solubility in water and also for their Log D value. The silymarin extract was obtained from Indena® (Indena Code: 9065110). The HPLC system consisted of Waters system equipped with performance PLUS inline degasser along dual λ absorbance detector set at 288 nm. The chromatographic separation of silymarin constituents was achieved on a Symmetry Shield RP18 column (150×4.6 mm, 5 μm); which was maintained at ambient room temperature conditions. The binary mobile phase system consisted of reservoir A (methanol: 10 mM ammonium acetate pH 5 [65:35 v/v]) and reservoir B (10 mM ammonium acetate, pH 5) were run as per gradient program (0-1.9 min: 25% A and 75% B; 2.0-14.9 min: 80% A and 20% B and 15-37.9 min: 80% A and 20% B and 38-40 min: 25% A and 75% B). The flow rate was 1 mL/min throughout the analytical run. The HPLC chromatogram of silymarin components is shown in FIG. 17.

To determine the Log D of silymarin components, the silymarin extract (2 mg) was dissolved in 100% DMSO and then used for the experiment. Different buffers between pH ranges of 1.0 to 12 were prepared by using universal buffer stock containing 25 mM hydrochloric acid, 25 mM citric acid, 25 mM phosphoric acid, 30 mM boric acid and 20 mM sodium chloride. About 45 mL of universal buffer was titrated with Sodium hydroxide (5M) to obtain desired pH. A 10 μL of silymarin stock solution was spiked into Eppendorf tube containing 500 μL each of a buffer and presaturated octanol. This mixture was vortexed for 5 minutes and kept for shaking at room temperature. After 16 h, the mixture was centrifuged at 10,000 RPM for 30 minutes. After centrifugation buffer and octanol phases were separated, both phases were diluted with acetonitrile (1:1) and subject to HPLC analysis for quantitation of individual components of silymarin. The Log D values of each compound at a pH was determined by Log D (pH)=Log [Organic (peak area)/Aqueous (peak area)].

The measured solubility and log D (pH 7.4) values are shown in Table 13 below.

TABLE 13

Solubility and Log D of various silymarin component ts

| Silymarin Components | Solubility in water (μg/mL) | Log D (7.4 pH) |
|---|---|---|
| Taxifolin | 550 | 1.35 |
| Silydianin | 232 | 1.64 |

TABLE 13-continued

| Solubility and Log D of various silymarin component ts | | |
|---|---|---|
| Silymarin Components | Solubility in water (μg/mL) | Log D (7.4 pH) |
| Silychristin | 170 | 0.53 |
| Silybin A | 7.71 | 2.26 |
| Silybin B | 21.9 | 1.99 |
| Isosilybin A | 18.8 | 2.47 |
| Isosilybin B | 6.36 | 2.53 |

Example 11

Mutual Phase Solubility Study of Silymarin—CAPTISOL® Complex

Two methods, method A and method B, were used to prepare the silymarin-CAPTISOL® complexes and the phase solubility of the various components in the complexes were measured and compared. The silymarin extract was obtained from Indena® (Indena Code: 9065110).

In method A, the Silymarin-CAPTISOL® complex was prepared through a hot extraction method. The steps of method A included: 1) preparing CAPTISOL® solutions at 10, 20, 40, 60, 70, and 100 mM by mixing CAPTISOL® with water; 2) combining an excess amount of silymarin with each CAPTISOL® solution in a sealed serum vial with a stir bar enclosed; 3) submerging the vial in a water bath at 70-75° C. on hot plate magnetic stirrer and stirring the suspension via the stir bar for 60 minutes; 4) cooling the solution to room temp by immersing in a room temperature water bath; and 5) centrifuging at 10,000 RPM and filtering using Millipore (0.22 μm) syringe filter. The filtrates were analyzed using HPLC for Taxifolin, Silychristin, Silydianin, Silybin A, Silybin B, Isosilybin A and Isosilybin B after appropriate dilution.

In method B, the Silymarin-CAPTISOL® complex was prepared by combining the CAPTISOL® and silymarin at ambient temperature: 120 mg of the extract was incorporated in 0 10, 20, 40, 60, 80 and 100 mM concentrations of CAPTISOL® solution in water. These samples were shook at room temperature for 3 days. At equilibrium, samples were centrifuged at 10,000 RPM and filtered using Millipore (0.22 μm) syringe filter. The filtrates were analyzed using HPLC for Taxifolin, Silychristin, Silydianin, Silybin A, Silybin B, Isosilybin A and Isosilybin B after appropriate dilution.

Figure 18B:
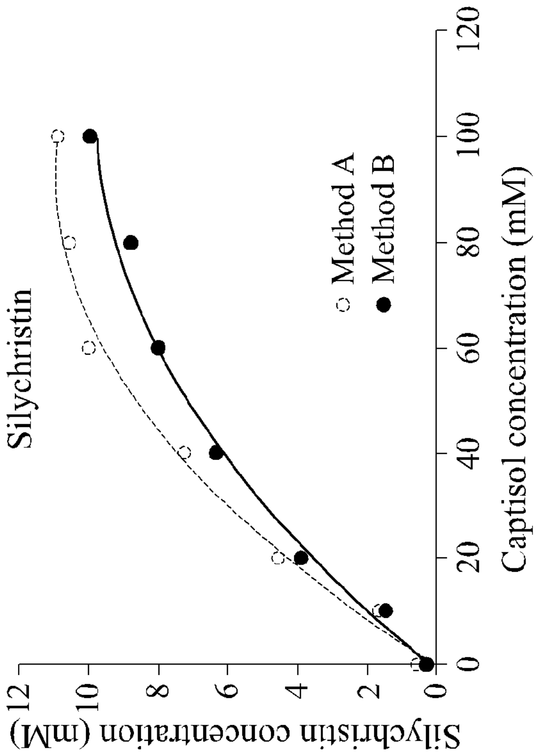
FIG. 18B shows the mutual phase solubility curve of silychristin in the silymarin-CAPTISOL® complex.
Figure 18A:
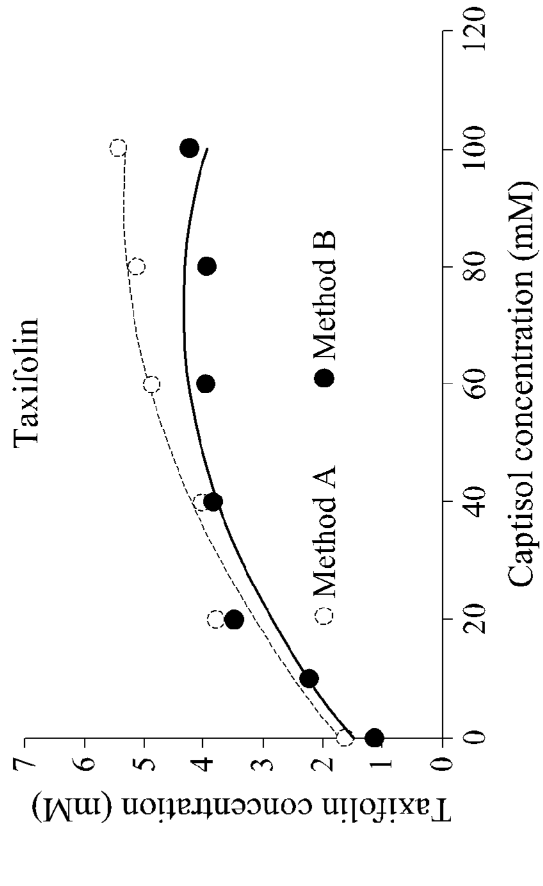
FIG. 18A shows the mutual phase solubility curve of taxifolin in the silymarin-CAPTISOL® complex.
Figure 18C:
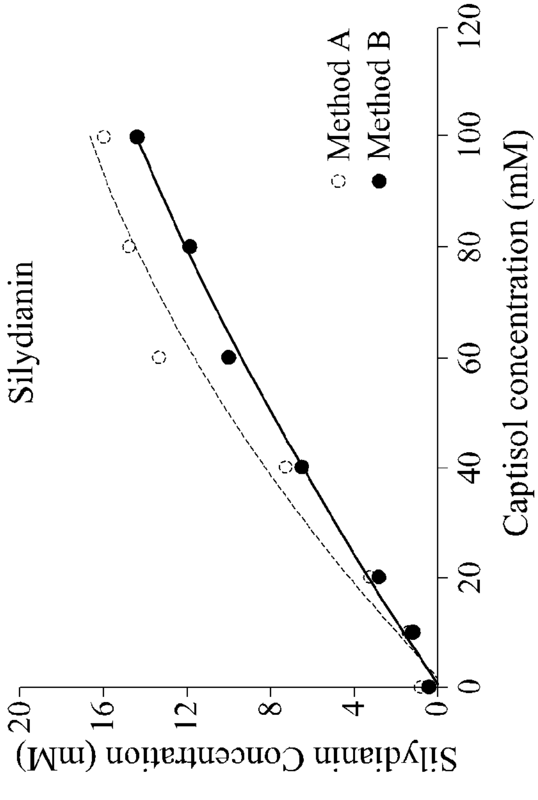
FIG. 18C shows the mutual phase solubility curve of silydianin in the silymarin-CAPTISOL® complex.
Figure 18D:
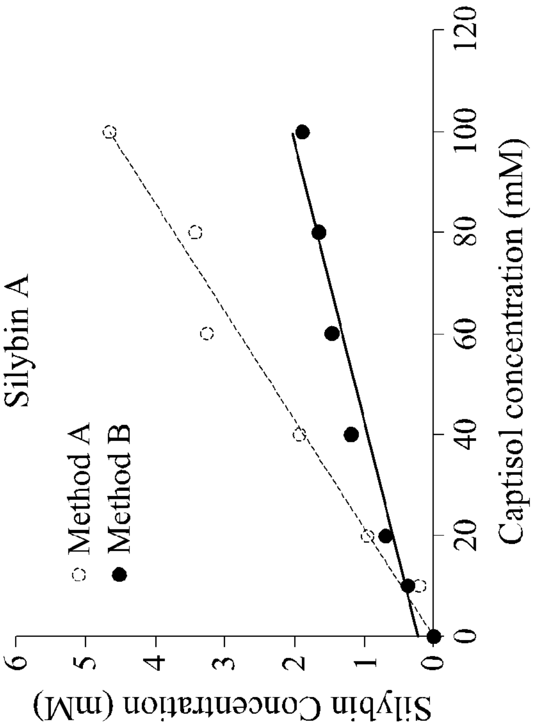
FIG. 18D shows the mutual phase solubility curve of silybin A in the silymarin-CAPTISOL® complex.
Figure 18E:
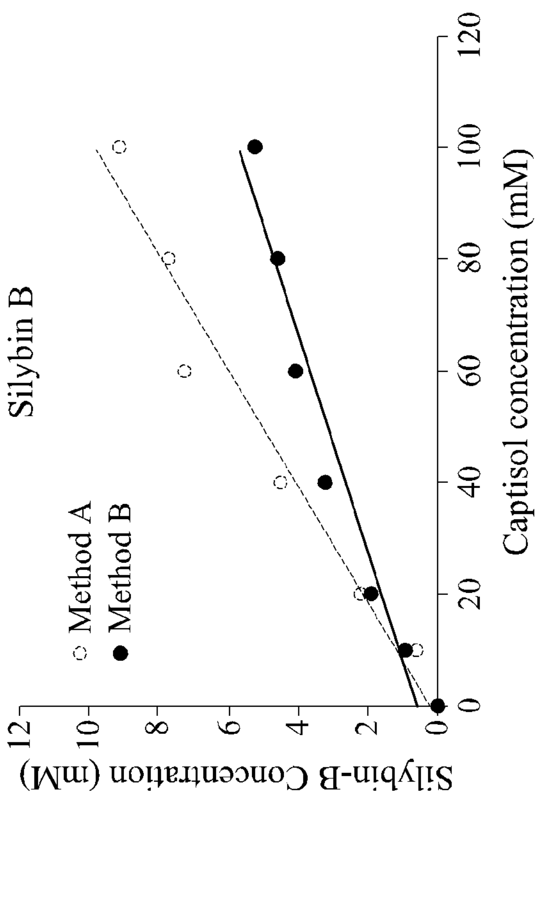
FIG. 18E shows the mutual phase solubility curve of silybin B in the silymarin-CAPTISOL® complex.
Figure 18F:
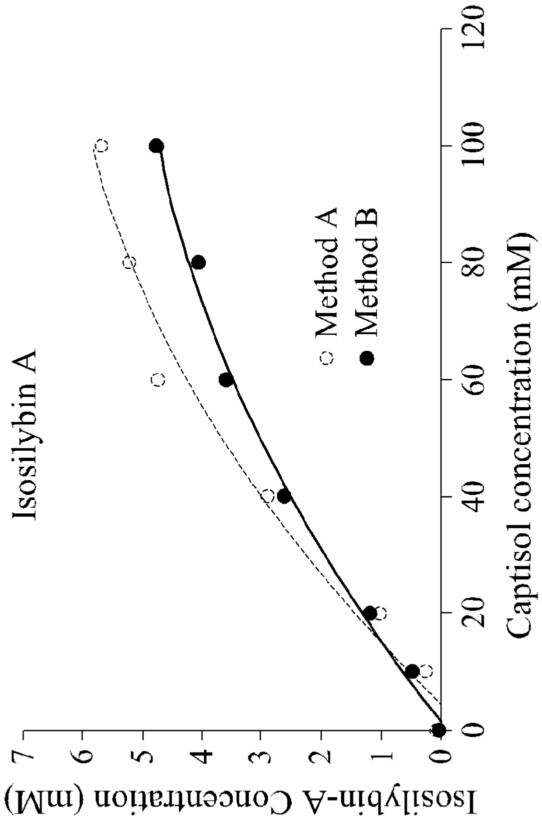
FIG. 18F shows the mutual phase solubility curve of isosilybin A in the silymarin-CAPTISOL® complex.
Figure 18G:
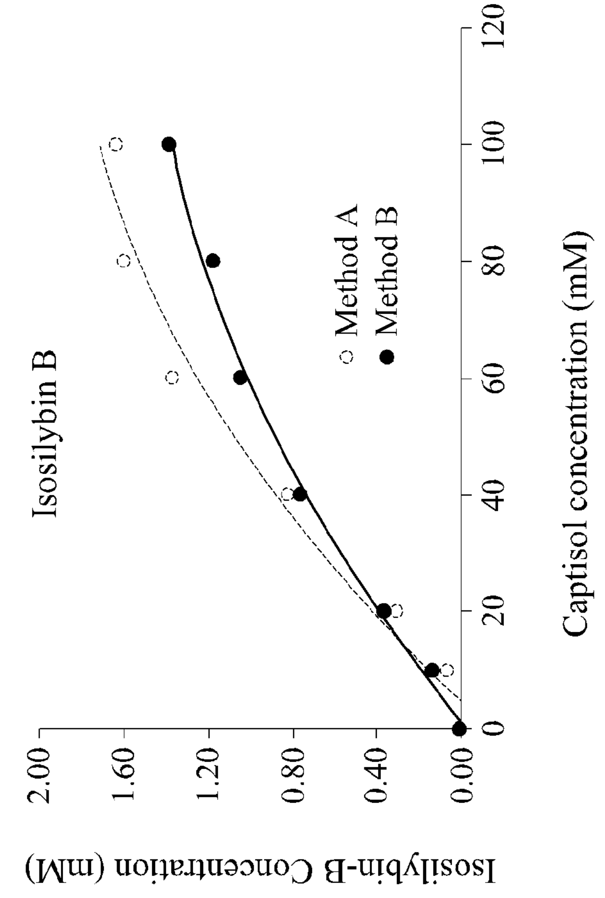
FIG. 18G shows the mutual phase solubility curve of isosilybin B in the silymarin-CAPTISOL® complex.

The solubility of the Silymarin-CAPTISOL® complexes prepared using method A and method B were measured. For each of the seven silymarin components, the Silymarin-CAPTISOL® complex prepared using method A generally showed higher solubility than the Silymarin-CAPTISOL® complex prepared using method B. The silymarin solubility differences in the two complexes became even greater at higher CAPTISOL® concentrations. FIG. 18A shows the mutual phase solubility curve of taxifolin in the silymarin-CAPTISOL® complex; FIG. 18B shows the mutual phase solubility curve of silychristin in the silymarin-CAPTISOL® complex; FIG. 18C shows the mutual phase solubility curve of silydianin in the silymarin-CAPTISOL® complex; FIG. 18D shows the mutual phase solubility curve of silybin A in the silymarin-CAPTISOL® complex; FIG. 18E shows the mutual phase solubility curve of silybin B in the silymarin-CAPTISOL® complex; FIG. 18F shows the mutual phase solubility curve of isosilybin A in the silymarin-CAPTISOL® complex; and FIG. 18G shows the mutual phase solubility curve of isosilybin B in the silymarin-CAPTISOL® complex. Tables 14A and 14B show the solubility increases of Silymarin-CAPTISOL® complex prepared using method A compared with the Silymarin-CAPTISOL® complex prepared using method B.

TABLE 14A

| The number of fold increase in Taxifolin, Silychristin, and Silydianin solubility | | | | | | |
|---|---|---|---|---|---|---|
| CAPTISOL ® | Taxifolin | | Silychristin | | Silydianin | |
| Concentration (mM) | Method A | Method B | Method A | Method B | Method A | Method B |
| 10 | 1.95 | 1.97 | 4.74 | 4.52 | 2.88 | 2.61 |
| 20 | 3.32 | 3.06 | 12.9 | 11.0 | 6.75 | 5.84 |
| 40 | 3.54 | 3.39 | 20.6 | 18.1 | 15.1 | 13.6 |
| 60 | 4.26 | 3.48 | 28.3 | 22.8 | 27.8 | 20.9 |
| 80 | 4.51 | 3.47 | 29.9 | 25.0 | 30.8 | 24.6 |
| 100 | 4.77 | 3.72 | 30.9 | 28.4 | 33.3 | 29.9 |

TABLE 14B

| The number of fold increase in Silybin A, Silybin B, Isosilybin A, and Isosilybin B solubility. | | | | | | | | |
|---|---|---|---|---|---|---|---|---|
| CAPTISOL ® | Silybin A | | Silybin B | | Isosilybin A | | Isosilybin B | |
| Conc (mM) | Method A | Method B | Method A | Method B | Method A | Method B | Method A | Method B |
| 10 | 13.4 | 22.3 | 13.4 | 20.6 | 6.74 | 12.3 | 4.94 | 10.5 |
| 20 | 58.7 | 42.6 | 48.5 | 42.6 | 26.7 | 31.1 | 23.3 | 27.9 |
| 40 | 121 | 73.8 | 99.3 | 71.1 | 74.1 | 67.8 | 62.4 | 58.4 |
| 60 | 204 | 91.6 | 160 | 90.4 | 122 | 92.6 | 104 | 79.4 |
| 80 | 214 | 103 | 171 | 102 | 134 | 105 | 122 | 89.5 |
| 100 | 291 | 117 | 201 | 116 | 146 | 122 | 125 | 106 |

Example 12

Permeation Across the Porcine Intestine

The Silymarin-CAPTISOL® complex was tested for its permeability in the GI tract using the porcine intestine and the silymarin solution without CAPTISOL® as a control sample. Freshly excised porcine intestine was cleaned and sandwiched between the two chambers of a Franz diffusion cell with an active diffusion area of 0.64 $cm^2$. The donor chamber was filled with 0.5 ml of CAPTISOL® enabled silymarin solution (prepared using ligand method) or pure silymarin in Phosphate buffered saline (PBS): Ethanol (80:20) used as a positive control. Receiver chamber was filled with 5 ml of PBS, pH 7.4, which is stirred at 600 rpm with a 3 mm magnetic stir bar at 37° C. temperature maintained with a circulating water bath. 200 μL of buffer from receiver side was withdrawn at different time intervals (0, 1, 2, 4, 6 and 8 h) and equal volume was replaced with fresh PBS buffer. Above samples were transferred into vials and subjected to HPLC analysis.

The control sample was prepared by adding excess of the silymarin extract to Phosphate buffered saline (PBS): Ethanol (80:20). These samples were shook at room temperature for 24 hr, and at equilibrium the samples were centrifuged at 10,000 RPM and filtered using Millipore (0.22 μm) syringe filter. The filtrates were analyzed using HPLC for Taxifolin, Silychristin, Silydianin, Silybin A, Silybin B, Isosilybin A and Isosilybin B after appropriate dilution.

The apparent permeability coefficient of silymarin $P_{app} \times 10^{-3}$ was calculated using $P_{app}=(dQ/dt)/(C_0 \times A)$, wherein dQ/dt is the rate of permeation across the porcine intestine, $C_0$ is the donor compartment concentration at 0 min, and A is the Area of porcine intestine. The apparent permeability coefficient of silymarin $P_{app} \times 10^{-3}$ as measured is listed in Table 15.

TABLE 15

Apparent permeability coefficient $P_{app} \times 10^{-3}$ of silymarin

| Silymarin components | Silymarin CAPTISOL ® complex | Silymarin in Ethanol:PBS (20:80) |
|---|---|---|
| Taxifolin | 9.46 | 1.12 |
| Silychristin | 7.90 | 0.35 |
| Silydianin | 5.54 | 0.52 |
| Silybin-A | 8.88 | 0.33 |
| Silybin-B | 88.9 | 0.27 |
| Isosilybin-A | 7.71 | 0.25 |
| Isosilybin-B | 8.18 | 0.22 |

Figure 19:
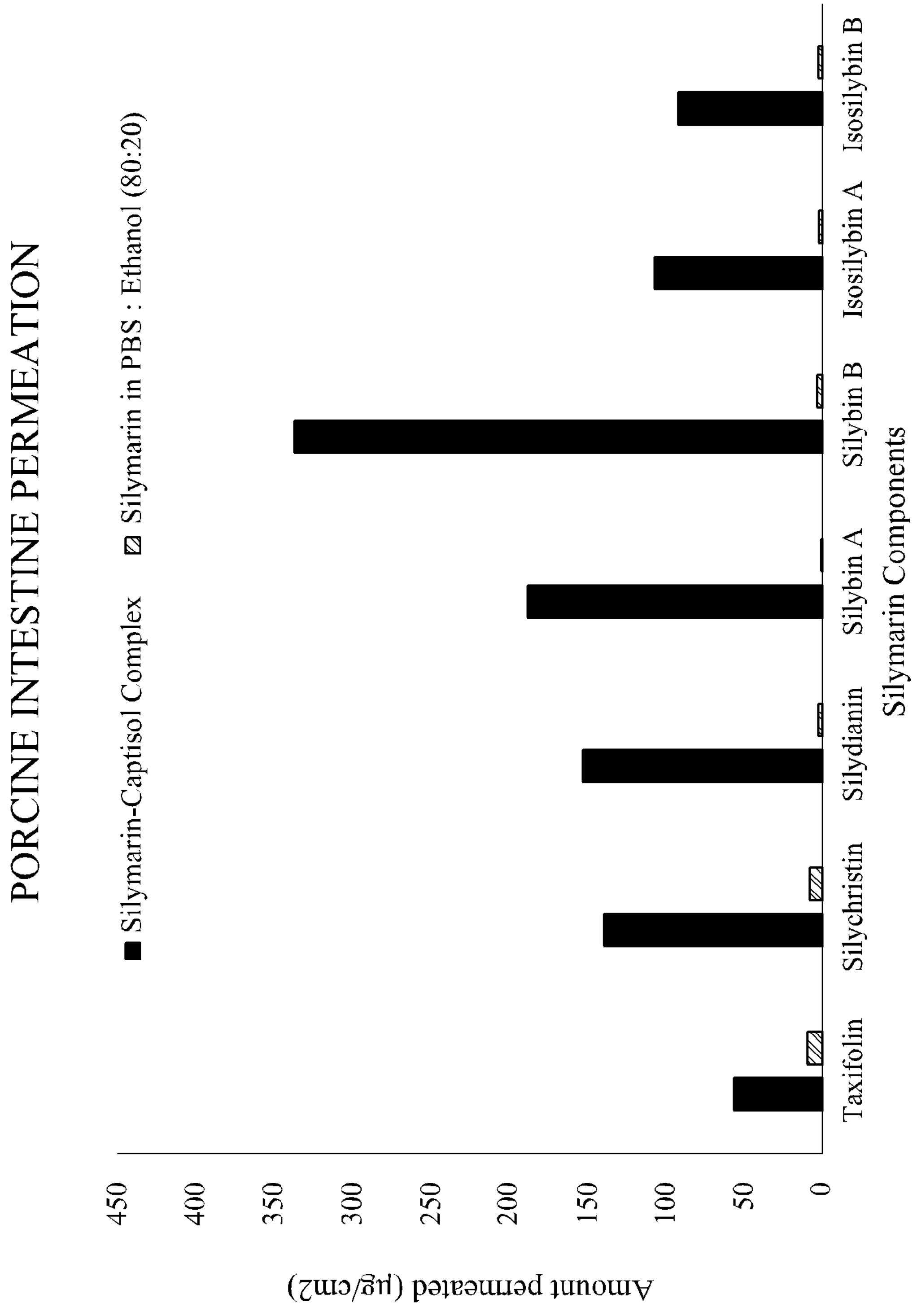
FIG. 19 shows the amount of silymarin components permeated through the porcine intestine in the control sample and in the Silymarin CAPTISOL® complex measured in Example 12.
Figure 20A:
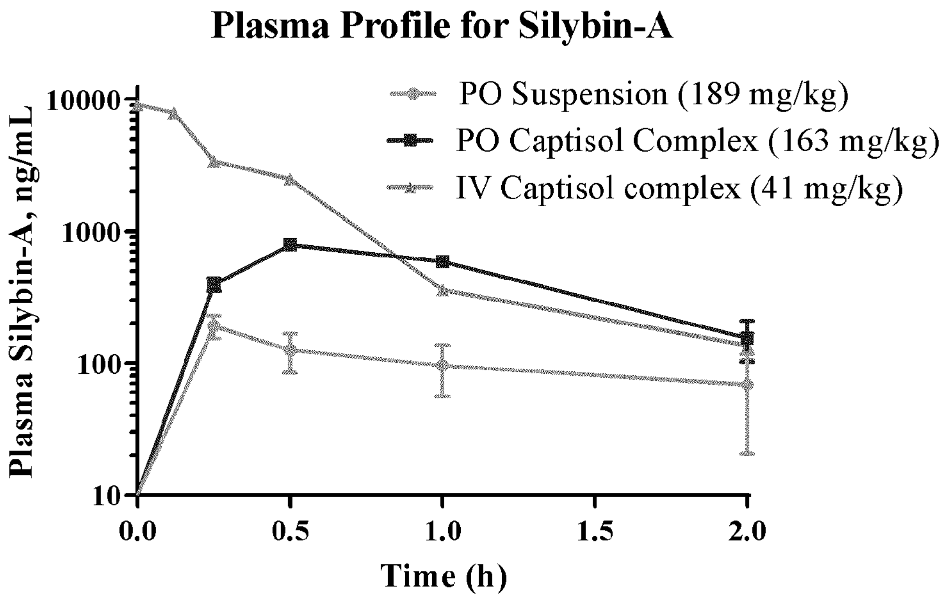
FIG. 20A shows shows the plasma concentration-time curve of silybin A.
Figure 20B:
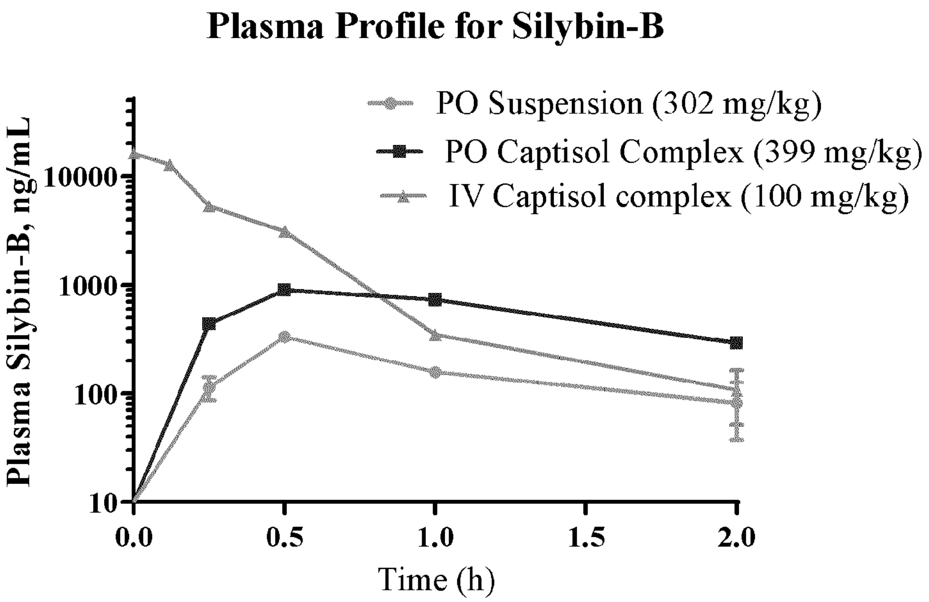
FIG. 20B shows the plasma concentration-time curve of silybin B.
Figure 20C:
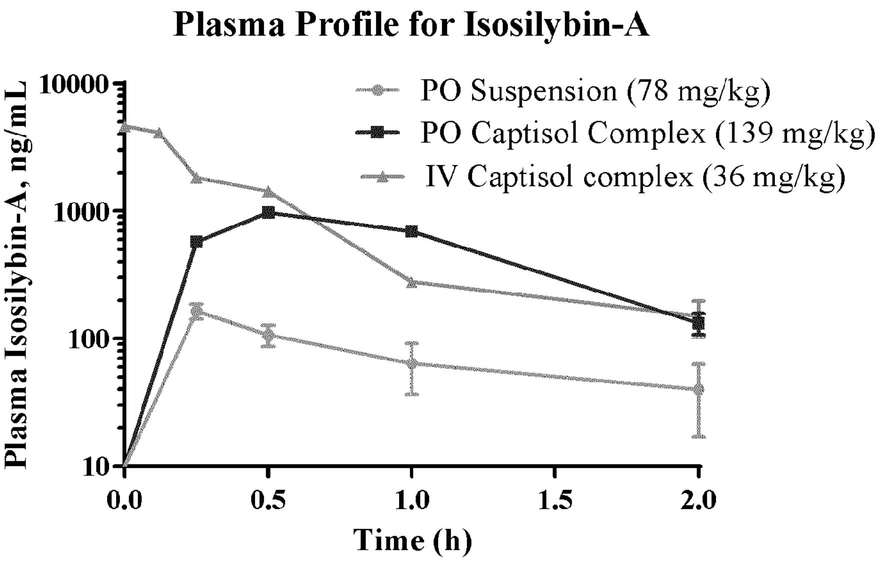
FIG. 20C shows the plasma concentration-time curve of isosilybin A.
Figure 20D:
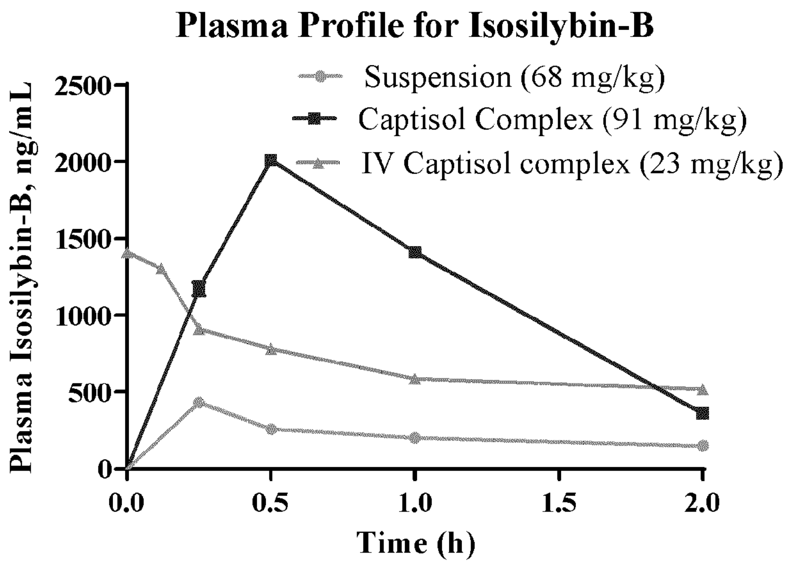
FIG. 20D shows the plasma concentration-time curve of isosilybin B.

Each of the silymarin components was measured for the amount that permeated across the porcine intestine. For all seven silymarin components, the Silymarin-CAPTISOL® complex showed better permeability than the control sample. The amount of silymarin component permeated across the porcine intestine also increased with time at a much faster rate than the control sample. FIG. 19 shows the amount of silymarin components permeated through the porcine intestine in the control sample and the Silymarin CAPTISOL® complex after 8 hours of permeation test. As shown in FIG. 18, for each silymarin component, the permeated amount is much greater in the Silymarin-CAPTISOL® sample than in the silymarin control sample. As shown in Table 15, the permeability coefficients for the seven silymarin components in the silymarin-CAPTISOL® complex are many folds greater than the silymarin alone sample, indicating an increased permeability using for silymarin-CAPTISOL® complex.

Example 13

Pharmacokinetic Study

The Silymarin-CAPTISOL® complex was administered to rat to test its pharmacokinetic properties.

On arrival rats were housed individually in cages at animal care facility in a temperature and humidity controlled room with a 12 h:12 h (light:dark) cycles. The rats were provided with free access to food and water for one week before using for experimental purpose. The 12 rats were equally divided into three groups—Group I: silymarin-CAPTISOL® complex with a CAPTISOL® concentration of 100 mM for oral administration; Group II: silymarin suspension (Control); and Group III: silymarin complex with a CAPTISOL® concentration of 100 mM for intravenous administration. The animals were fasted overnight with free access to water. On the day of experiment, the rat was removed from animal care facility and brought to the procedure lab. The animal was weighed and appropriate dosing volume was determined. For oral administration, rat's head was held in place by gently extending the head back and supporting the lower body. The gavage tube was placed in the mouth and advanced along the lower palate till the esophagus, and the silymarin was administered through the tube. For intravenous administration, the silymarin-CAPTISOL® complex was administered by slow bolus intravenous injection into the tail vein. Approximately 200 μL blood was drawn into heparin coated tubes at pre dose, 0.15, 0.5, 1, 2, 4, 8, 10 and 24 h for oral group II and for intravenous group III. The sampling time points were pre-dose, 0.12, 0.25, 0.5, 1, 2, 4, 8 and 24 h through the jugular vein catheter. Plasma was harvested by centrifuging the blood at 4000 RPM for 5 min and stored frozen at −80±10° C. until analysis.

Stored plasma was thawed just before performing the silymarin components analysis. 200 μL of acetonitrile containing 0.1% of ammonia was added to 50 μL of plasma, and this mixture was vortexed for 5 min and centrifuged at 4° C. for 5 min at 10,000 RPM. After centrifugation, the supernatant was separated and injected into HPLC for analysis of silymarin constituents taxifolin, silydianin, silychristin, silybin A, silybin B, isosilybin A and isosilybin B.

Figure 21A:
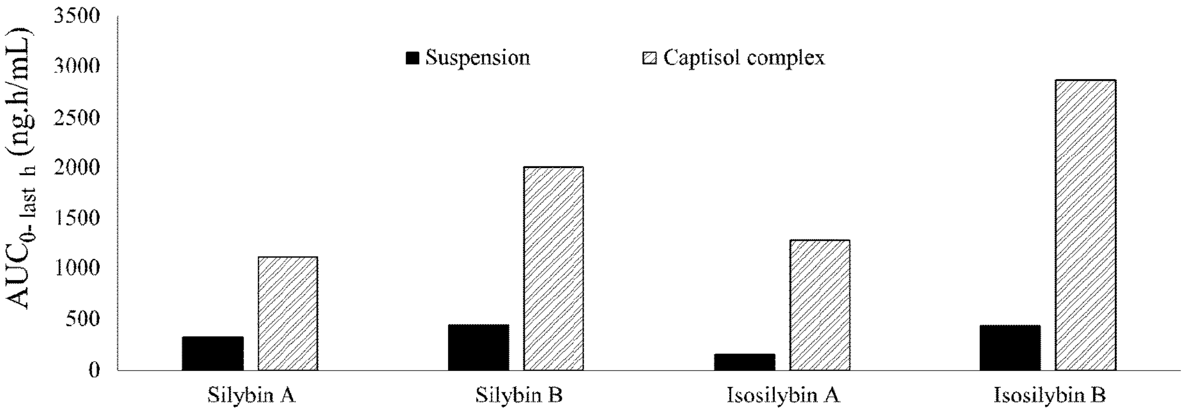
FIG. 21A shows the $AUC_{(0\text{-}inf)}$ comparison of the silymarin CAPTISOL® complex and the control sample for silybin A, silybin A, isosilybin A, and isosilybin B.
Figure 21B:
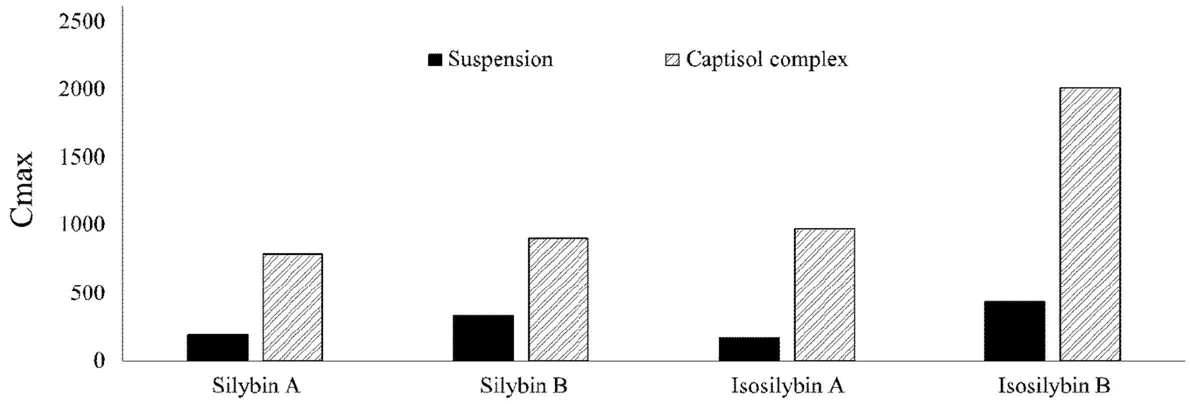
FIG. 21B shows the $C_{max}$ comparison of the silymarin CAPTISOL® complex and the control sample for silybin A, silybin A, isosilybin A, and isosilybin B.

The plasma concentration-time curves of silybin A, silybin B, isosilybin A, and isosilybin B in the Silymarin-CAPTISOL® sample of Group I and the control sample (silymarin suspension) are respectively shown in FIGS. 20A to 20D. FIG. 21A shows the AUC comparison of the silymarin CAPTISOL® complex and the control sample for silybin A, silybin A, isosilybin A, and isosilybin B; and FIG. 21B shows the $C_{max}$ comparison of the silymarin CAPTISOL® complex and the control sample for silybin A, silybin A, isosilybin A, and isosilybin B. The results of the pharmacokinetic study using the Silymarin-CAPTISOL® samples and the control sample are also summarized below in Table 16. % $F_{abs}$ is calculated using the formula below:

$$F_{abs} = 100 \cdot \frac{AUC_{po} \cdot D_{iv}}{AUC_{iv} \cdot D_{po}}$$

TABLE 16

| | Parameters | Oral Silymarin suspension (n = 3) | Oral Silymarin-CAPTISOL ® complex (n = 4) | IV Silymarin-CAPTISOL ® complex (n = 4) |
|---|---|---|---|---|
| Pharmacokinetic study results of Silymarin components | | | | |
| | | Formulation | | |
| Silybin A | Dose (mg/kg) | 189 | 163 | 40.8 |
| | $AUC_{(0\text{-}2\ h)}$ (ng · h/mL) | 271 | 1067 | 3445 |
| | $T_{max}$ (h) | 0.50 | 0.50 | 0.12 |
| | $C_{max}$ (ng/mL) | 191 | 787 | 7907 |
| | % $F_{abs}$ | 1.67 | 7.60 | N/A |
| Silybin B | Dose (mg/kg) | 302 | 399 | 100 |
| | $AUC_{(0\text{-}2\ h)}$ (ng · h/mL) | 395 | 1432 | 5074 |
| | $T_{max}$ (h) | 0.50 | 0.63 | 0.12 |
| | $C_{max}$ (ng/mL) | 333 | 907 | 12737 |
| | % $F_{abs}$ | 2.58 | 7.07 | N/A |
| Isosilybin A | Dose (mg/kg) | 78.0 | 139 | 35 |
| | $AUC_{(0\text{-}2\ h)}$ (ng · h/mL) | 150 | 1230 | 1971 |
| | $T_{max}$ (h) | 0.50 | 0.50 | 0.07 |
| | $C_{max}$ (ng/mL) | 165 | 976 | 4162 |
| | % $F_{abs}$ | 2.56 | 11.8 | N/A |

| | | Formulation | | |
|---|---|---|---|---|
| | Parameters | Oral Silymarin suspension (n = 3) | Oral Silymarin-CAPTISOL ® ® complex (n = 4) | IV Silymarin-CAPTISOL ® complex (n = 4) |
| Isosilybin B | Dose (mg/kg) | 67.5 | 91 | 23 |
| | $AUC_{(0\text{-}2\ h)}$ (ng · h/mL) | 433 | 2647 | 1417 |
| | $T_{max}$ (h) | 0.50 | 0.50 | 0.12 |
| | $C_{max}$ (ng/mL) | 432 | 2011 | 1308 |
| | % $F_{abs}$ | 10.3 | 46.7 | N/A |

As shown in the FIGS. 21A and 21B and also in Table 16, the Silymarin-CAPTISOL® complex had better pharmacokinetic properties, including higher AUC for taxifolin, silybin A, silybin A, isosilybin A, and isosilybin B, and higher $C_{max}$ than the control sample for silybin A, silybin A, isosilybin A, and isosilybin B. In addition, the silymarin-CAPTISOL® complex also showed higher % $F_{abs}$ and thus better oral bioavailability for silybin A, silybin A, isosilybin A, and isosilybin B than silymarin alone. Therefore, the complex formed between sulfoalkyl ether cyclodextrin and silymarin or silymarin components clearly shows better pharmacokinetic properties and oral bioavailability than silymarin or silymarin components alone.

Although the invention has been described with reference to embodiments and examples, it should be understood that numerous and various modifications can be made without departing from the spirit of the invention. Accordingly, the invention is limited only by the claims.

What is claimed is:

1. A composition, comprising:

silybin A;

isosilybin A; and sulfoalkyl ether cyclodextrin; wherein the molar ratio between silybin A and isosilybin A is (0.4-0.6):(0.5-0.9).

2. The composition of claim 1, wherein the sulfoalkyl ether cyclodextrin is a compound, or a mixture thereof, of Formula I:

Formula 1

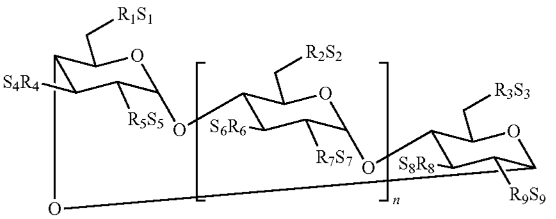

wherein:

n is 4, 5, or 6;

$R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group, wherein at least one of $R_1$ to $R_9$ is independently a —O—($C_2$-$C_6$ alkylene)-$SO_3^-$ group, a —O—$(CH_2)_m$ $SO_3^-$ group wherein m is 2 to 6, —$OCH_2CH_2CH_2SO_3^-$, or —$OCH_2CH_2CH_2CH_2SO_3^-$; and $S_1$, $S_2$, $S_3$, $S_4$, $S_5$, $S_6$, $S_7$, $S_8$, and $S_9$, are each, independently, a pharmaceutically acceptable cation.

3. The composition of claim 1, wherein the sulfoalkyl ether cyclodextrin is a compound, or a mixture thereof, of Formula II Formula (II)

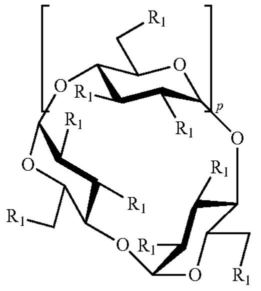

or a pharmaceutically acceptable salt thereof, wherein:

p is 4, 5, or 6, and each $R_1$ is independently —O—($C_1$-$C_8$ alkylene)-$SO_3T$ or —OH, and;

each T is independently hydrogen or pharmaceutically acceptable cation, provided that at least one $R_1$ is —OH.

4. The composition of claim 1, wherein the molar percentage of silybin A is in the range of about 3% to about 12% based on the total moles of all flavonolignan components.

5. The composition of claim 1, comprising silybin B, and wherein the molar percentage of silybin B is in the range of about 5% to about 25% based on the total mole of all flavonolignan components.

6. The composition of claim 1, wherein the molar percentage of isosilybin A is in the range of about 5% to about 16% based on the total moles of all flavonolignan components.

7. The composition of claim 1, comprising isosilybin B, and wherein the molar percentage of isosilybin B is in the range of about 1% to about 5% based on the total moles of all flavonolignan components.

8. The composition of claim 1, wherein the molar ratio of silybin A to silybin B to isosilybin A to isosilybin B is about 10:22:14:4.

9. The composition of claim 1, further comprising one or more anti-oxidants.

10. A composition for topical application, comprising the composition of claim 1 in the form of a gel.

11. The composition of claim 10, further comprising phenoxyethanol, ethanol, PEG 400, and hydroxypropyl cellulose.

12. The composition of claim 11, wherein the amount of the phenoxyethanol is in the range of about 0.1% to 10% by weight, based on the total weight of the composition; wherein the amount of ethanol is in the range of about 1% to 30% by weight, based on the total weight of the composition; wherein the amount of PEG 400 is in the range of about 1% to 50% by weight, based on the total weight of the composition; wherein the amount of sulfoalkyl ether cyclodextrin is in the range of about 1% to 90% by weight, based on the total weight of the composition; and wherein the amount of hydroxypropyl cellulose is in the range of about 0.1% to 10% by weight, based on the total weight of the composition.

13. The composition of claim 1, comprising silybin A, silybin B, isosilybin B, wherein the molar ratio of silybin A to silybin B to isosilybin A to isosilybin B is in the range of (0.4-0.6):(0.9-1.5):(0.5-0.9):(0.1-0.3).

* * * * *